(12) United States Patent
Kim et al.

(10) Patent No.: US 11,081,653 B2
(45) Date of Patent: Aug. 3, 2021

(54) HETEROCYCLIC COMPOUND AND ORGANIC LIGHT EMITTING ELEMENT USING SAME

(71) Applicant: LT MATERIALS CO., LTD., Yongin (KR)

(72) Inventors: Mi-Jin Kim, Ulsan (KR); Won-Jang Jeong, Hwaseong-si (KR); Jin-Seok Choi, Suwon-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 199 days.

(21) Appl. No.: 15/773,657

(22) PCT Filed: Nov. 8, 2016

(86) PCT No.: PCT/KR2016/012794
§ 371 (c)(1),
(2) Date: May 4, 2018

(87) PCT Pub. No.: WO2017/086643
PCT Pub. Date: May 26, 2017

(65) Prior Publication Data
US 2018/0323379 A1  Nov. 8, 2018

(30) Foreign Application Priority Data
Nov. 6, 2015 (KR) .......... 10-2015-0156174

(51) Int. Cl.
*H01L 51/00* (2006.01)
*H01L 51/50* (2006.01)
(Continued)

(52) U.S. Cl.
CPC ........ *H01L 51/0072* (2013.01); *C07D 471/04* (2013.01); *C07D 519/00* (2013.01);
(Continued)

(58) Field of Classification Search
CPC ............... H01L 51/5088; H01L 51/507; H01L 51/0067; H01L 51/5012; H01L 51/5092;
(Continued)

(56) References Cited

U.S. PATENT DOCUMENTS

2011/0049494 A1    3/2011   Kim et al.

FOREIGN PATENT DOCUMENTS

KR    10-2011-0023090 A    3/2011
KR    10-2014-0093163 A    7/2014
(Continued)

OTHER PUBLICATIONS

International Search Report for PCT/KR2016/012794 (PCT/ISA/210) dated Feb. 17, 2017.
(Continued)

*Primary Examiner* — Golam Mowla
(74) *Attorney, Agent, or Firm* — Birch, Stewart, Kolasch & Birch, LLP

(57) ABSTRACT

The present application provides a hetero-cyclic compound which may significantly improve the service life, efficiency, electrochemical stability, and thermal stability of an organic light emitting device, and an organic light emitting device in which the hetero-cyclic compound is contained in an organic compound layer.

6 Claims, 18 Drawing Sheets

(51) Int. Cl.
*C07D 471/04* (2006.01)
*C09K 11/06* (2006.01)
*C07D 519/00* (2006.01)

(52) U.S. Cl.
CPC .......... *C09K 11/06* (2013.01); *H01L 51/0058* (2013.01); *H01L 51/0067* (2013.01); *C09K 2211/1018* (2013.01); *C09K 2211/1044* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC .............. H01L 51/5096; H01L 51/0058; H01L 51/5016; H01L 51/0072; H01L 51/5056
See application file for complete search history.

(56) References Cited

FOREIGN PATENT DOCUMENTS

| | | |
|---|---|---|
| KR | 10-2015-0028173 A | 3/2015 |
| KR | 10-2015-0076602 A | 7/2015 |
| TW | 201434820 A | 9/2014 |
| TW | 201509940 A | 3/2015 |

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials", Advanced Materials, 1994, vol. 6, No. 9, pp. 677-679.

[Figure 1]
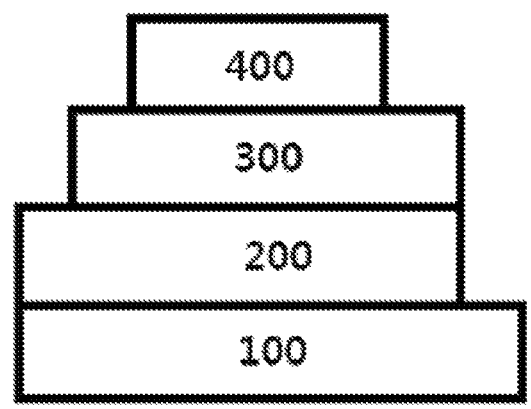
[Figure 2]
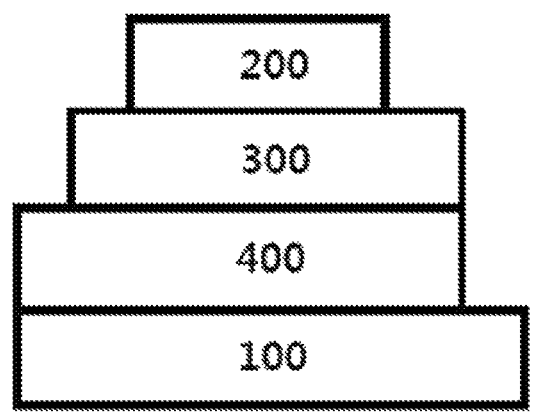

[Figure 3]
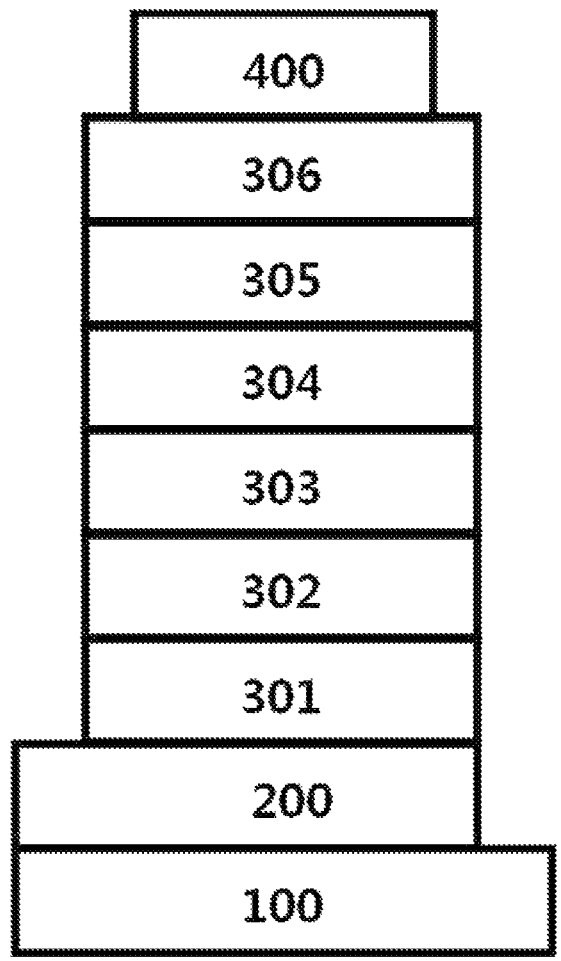

[Figure 4]
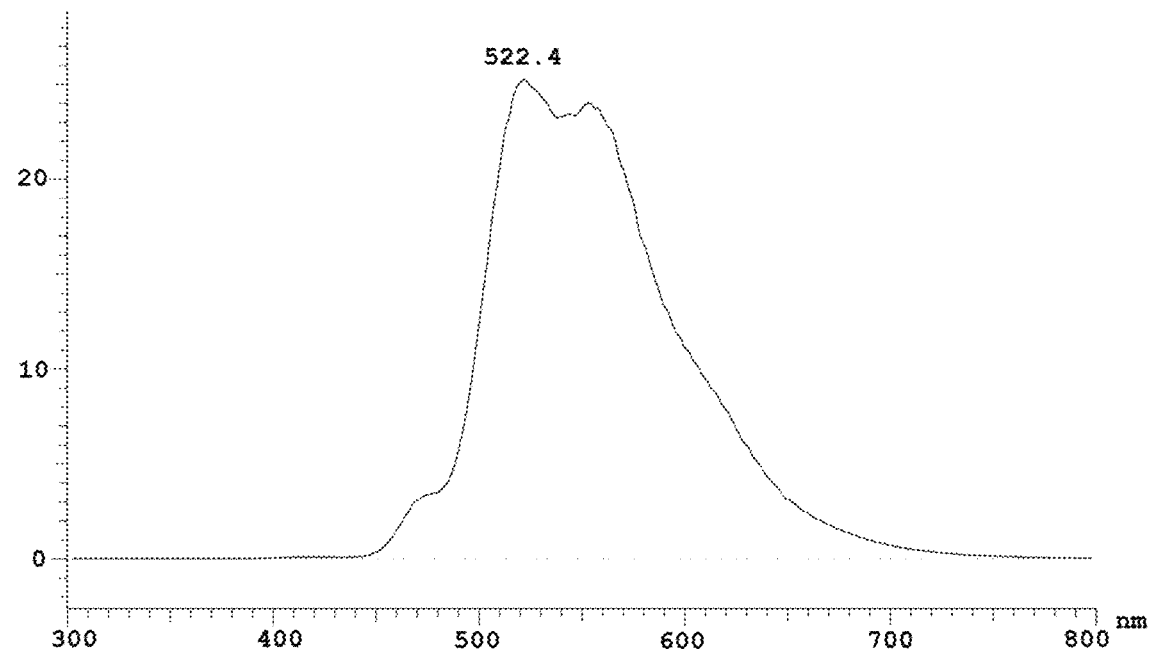
[Figure 5]
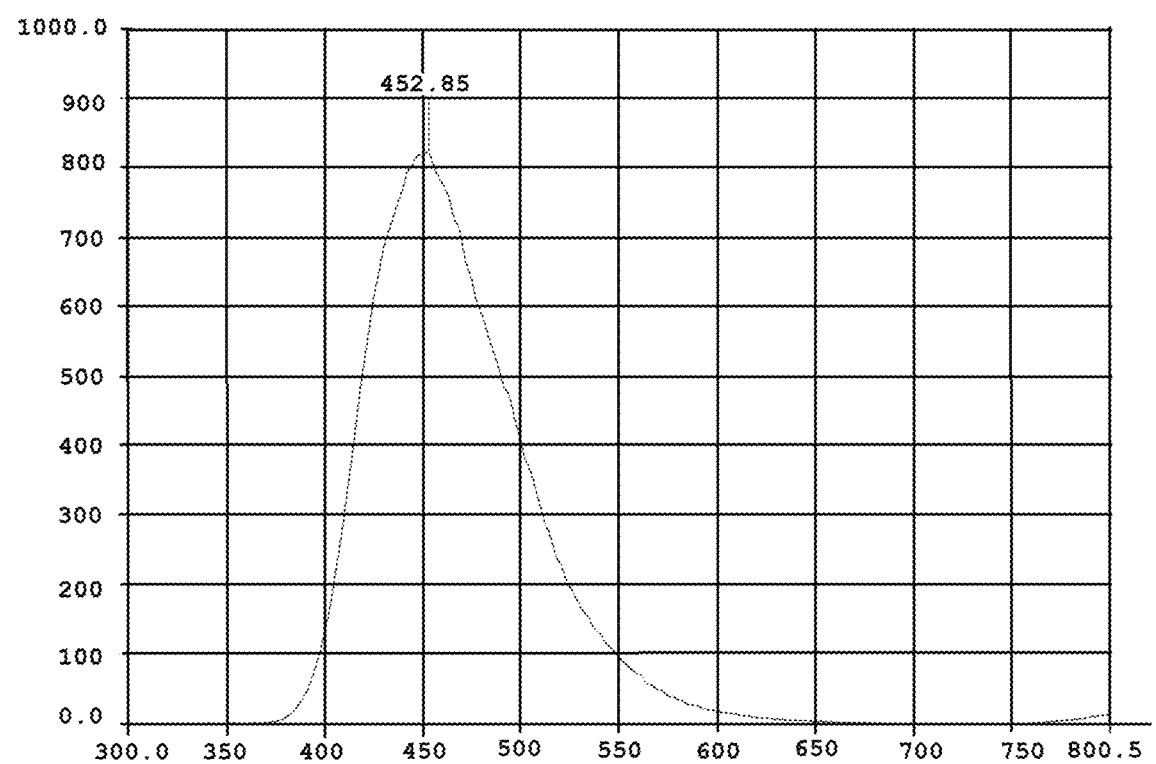

[Figure 6]
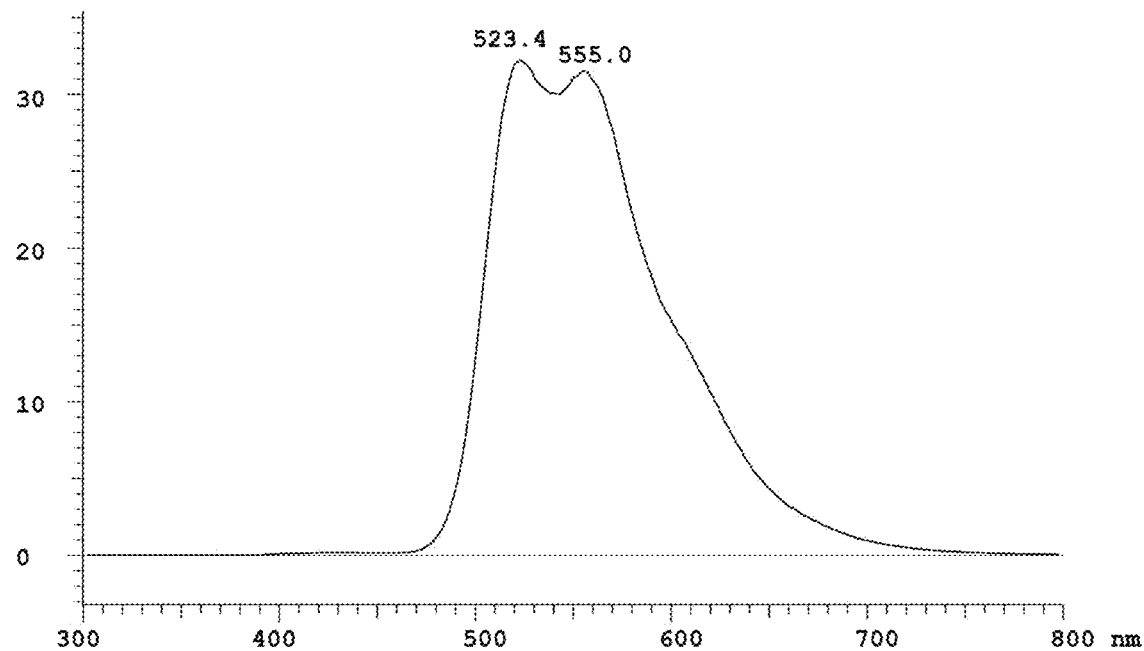
[Figure 7]
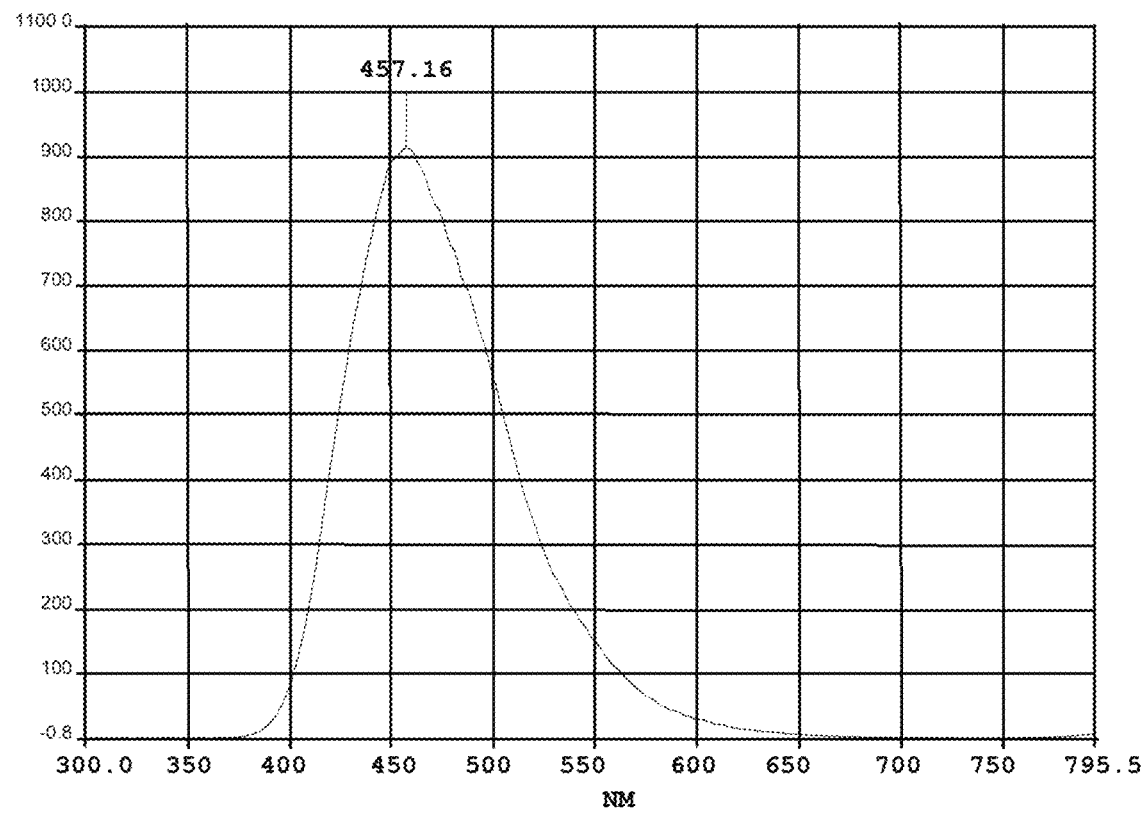

[Figure 8]
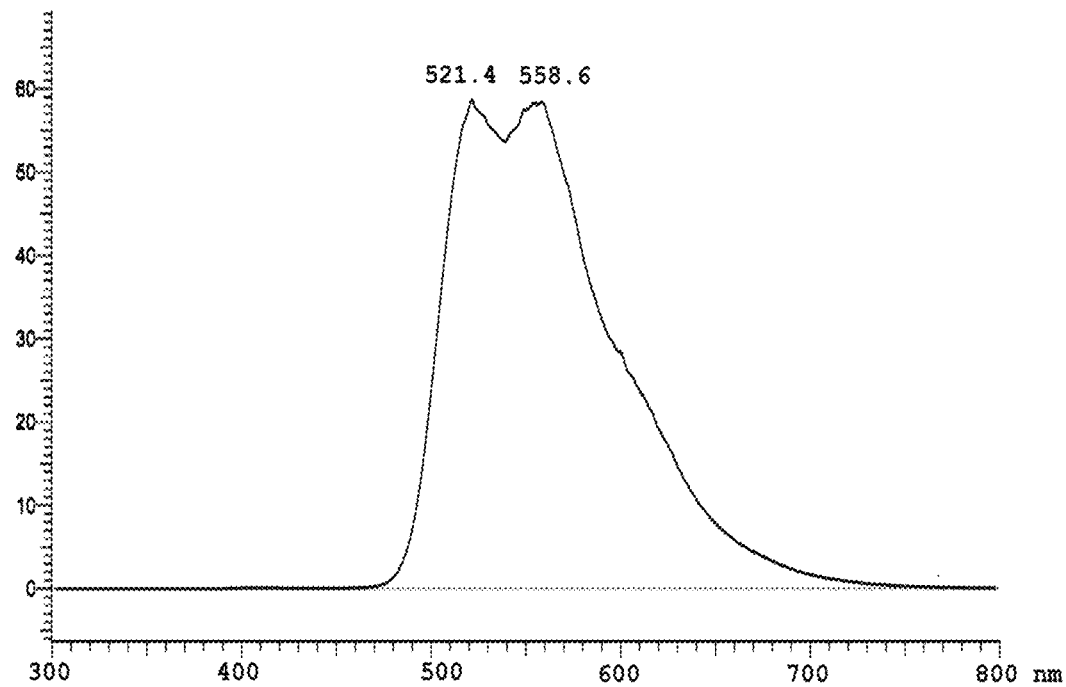
[Figure 9]
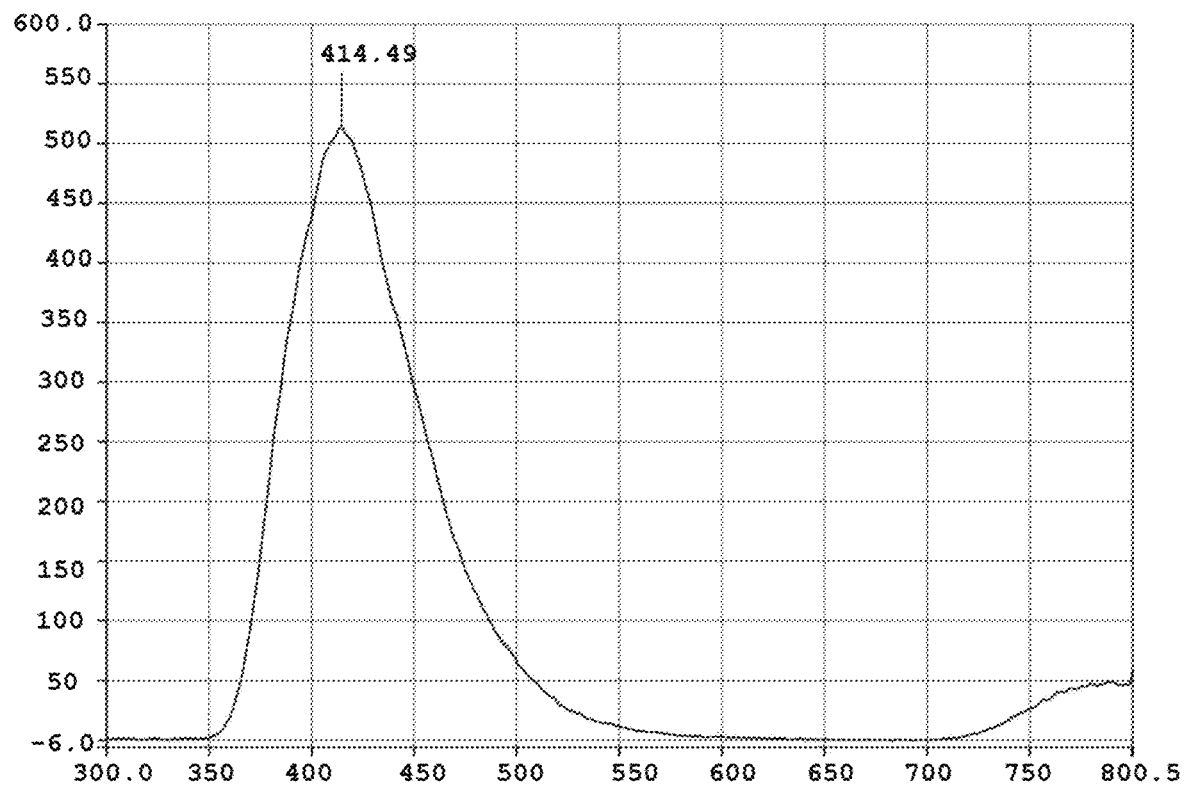

[Figure 10]
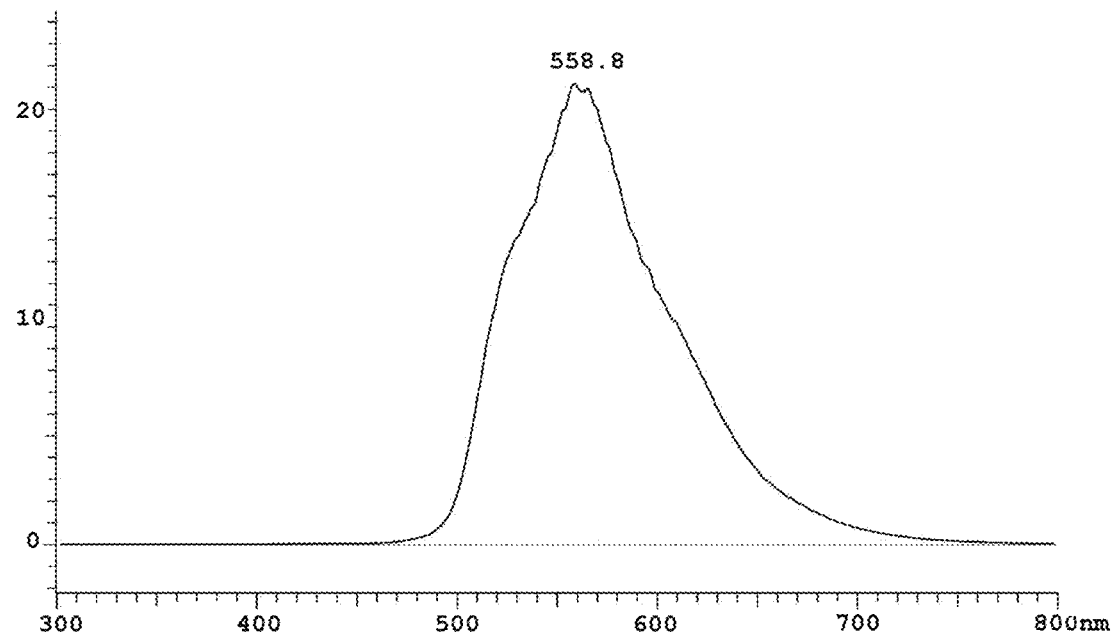
[Figure 11]
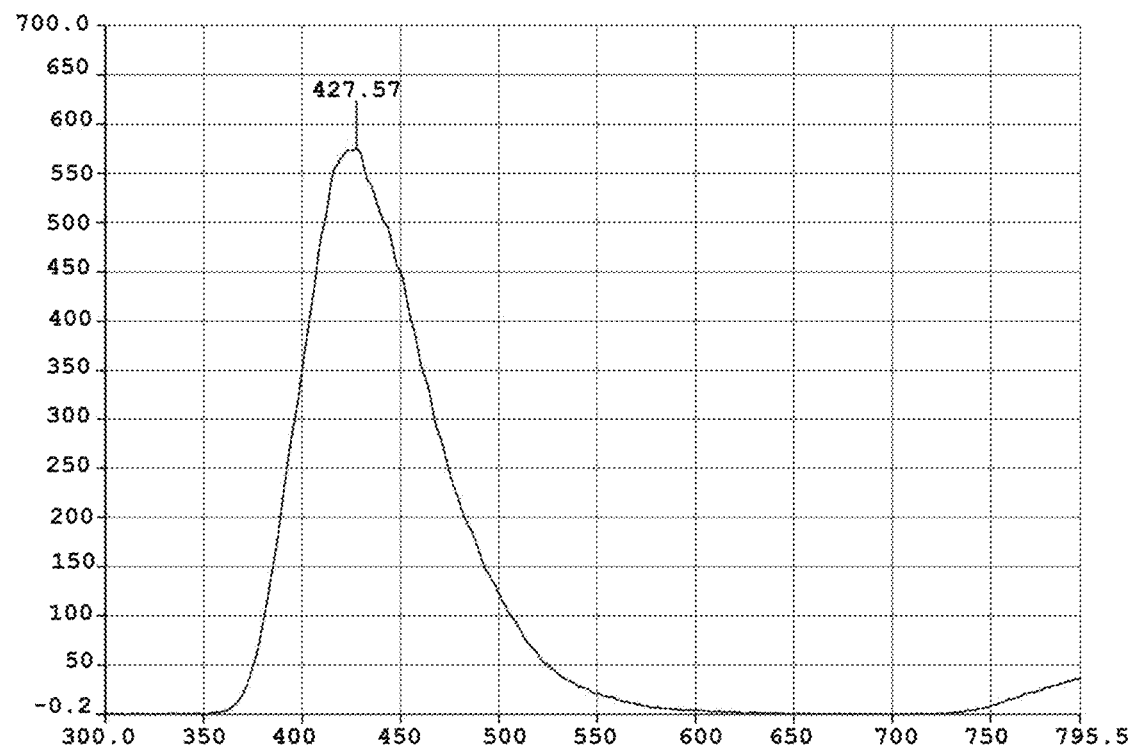

[Figure 12]
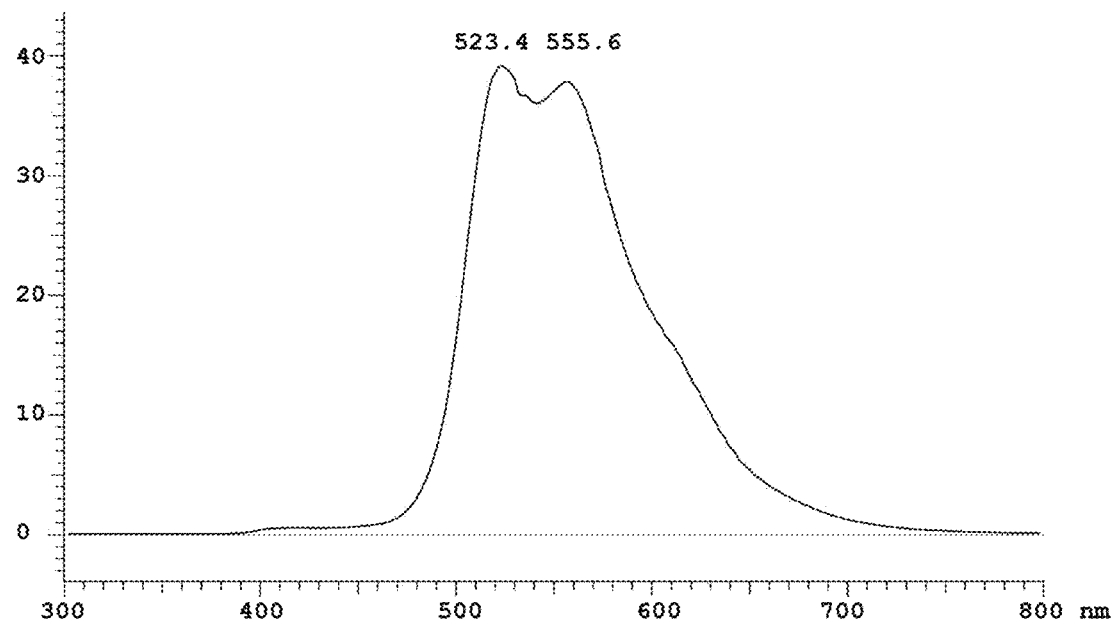
[Figure 13]
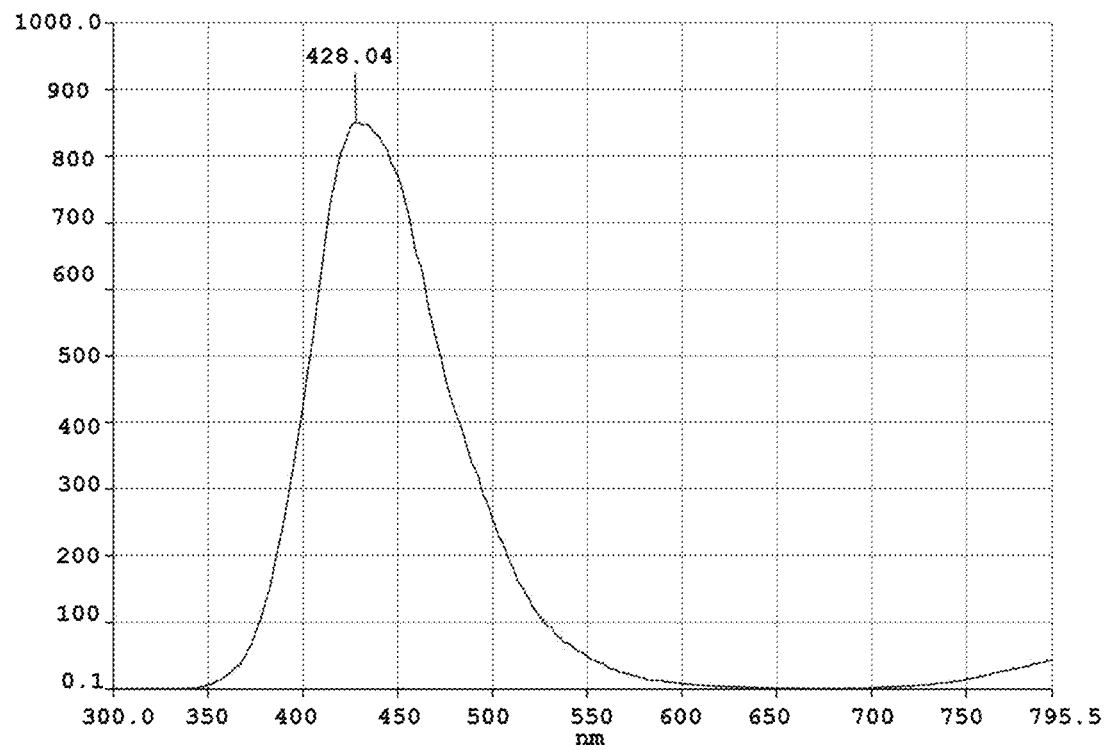

[Figure 14]
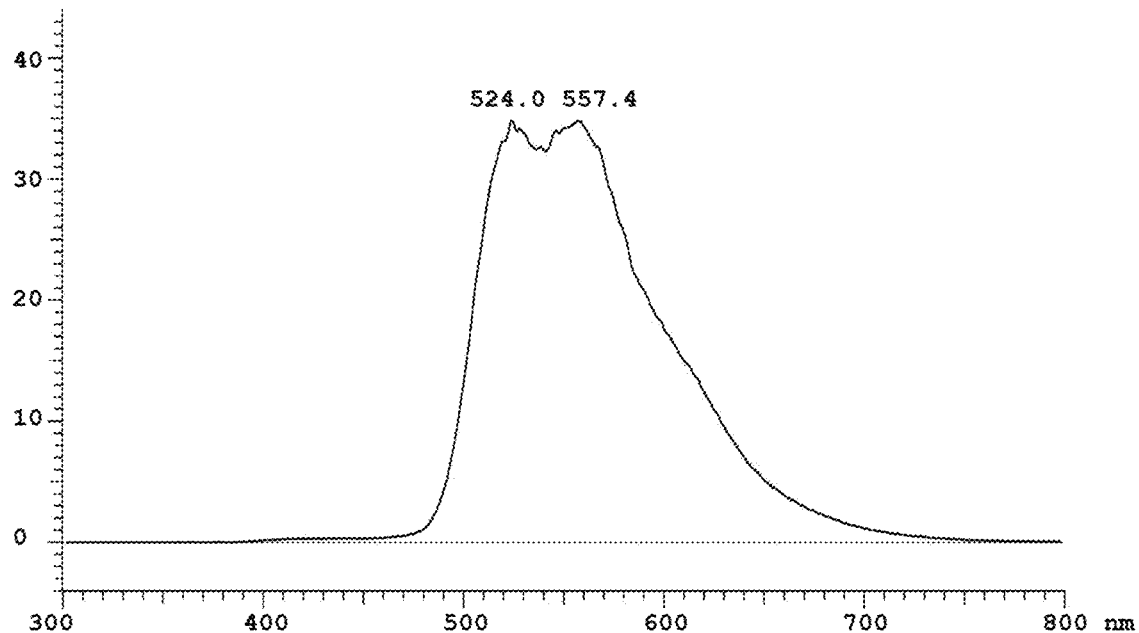
[Figure 15]
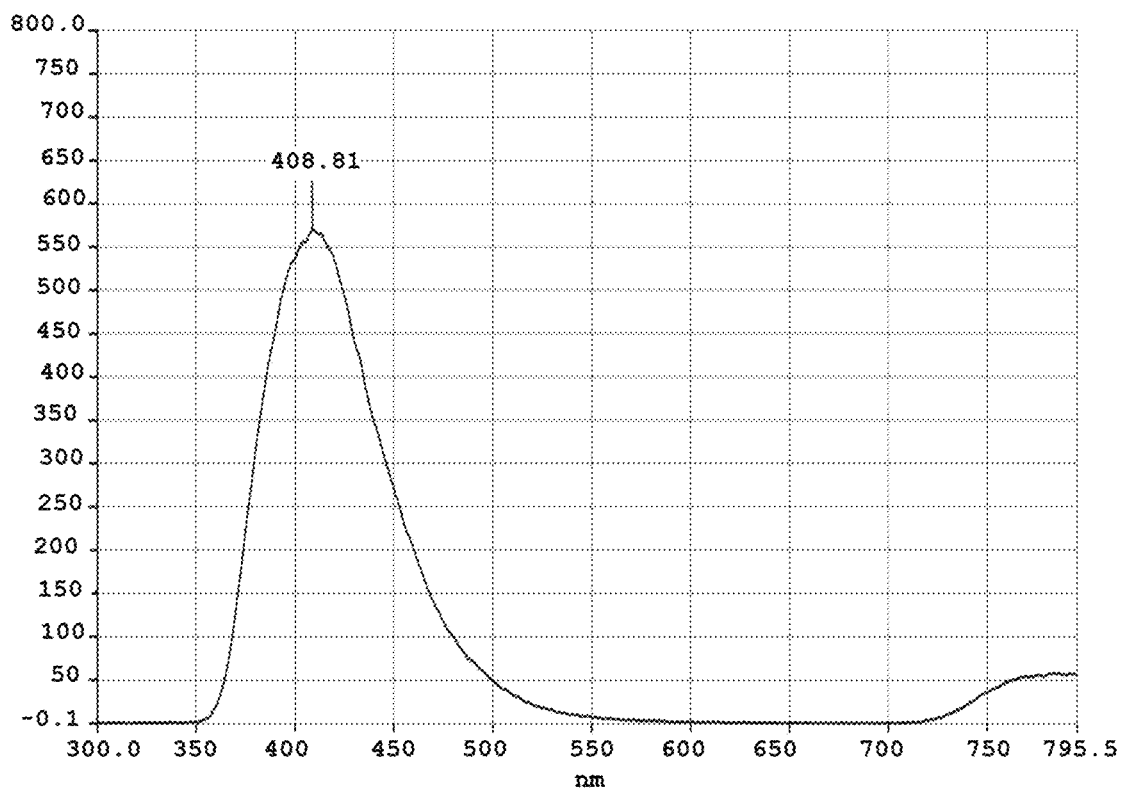

[Figure 16]
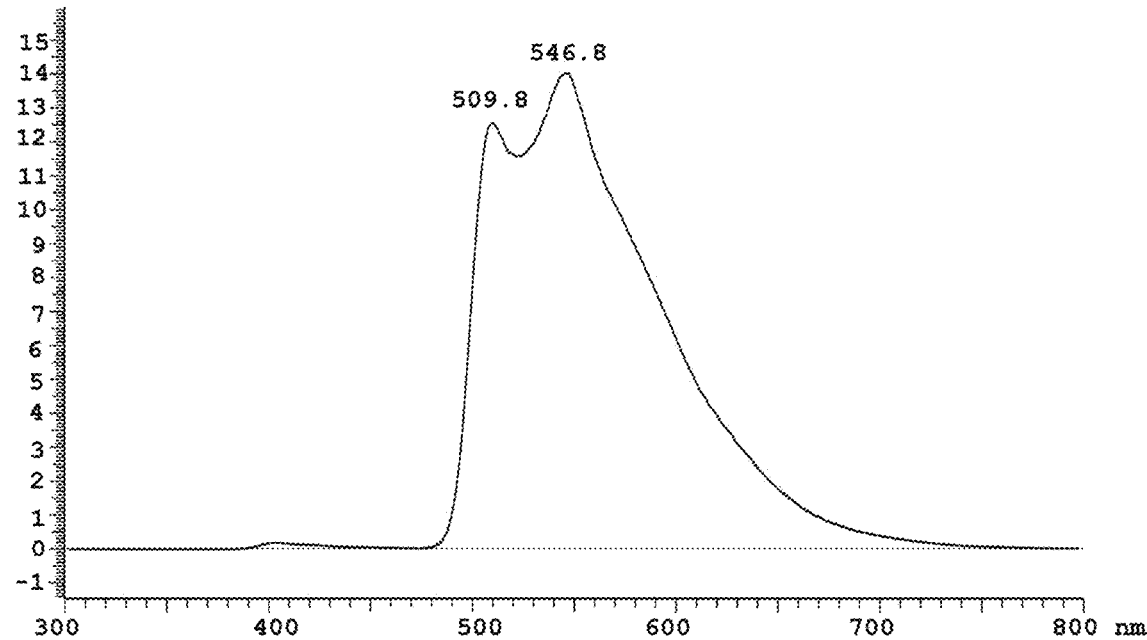
[Figure 17]
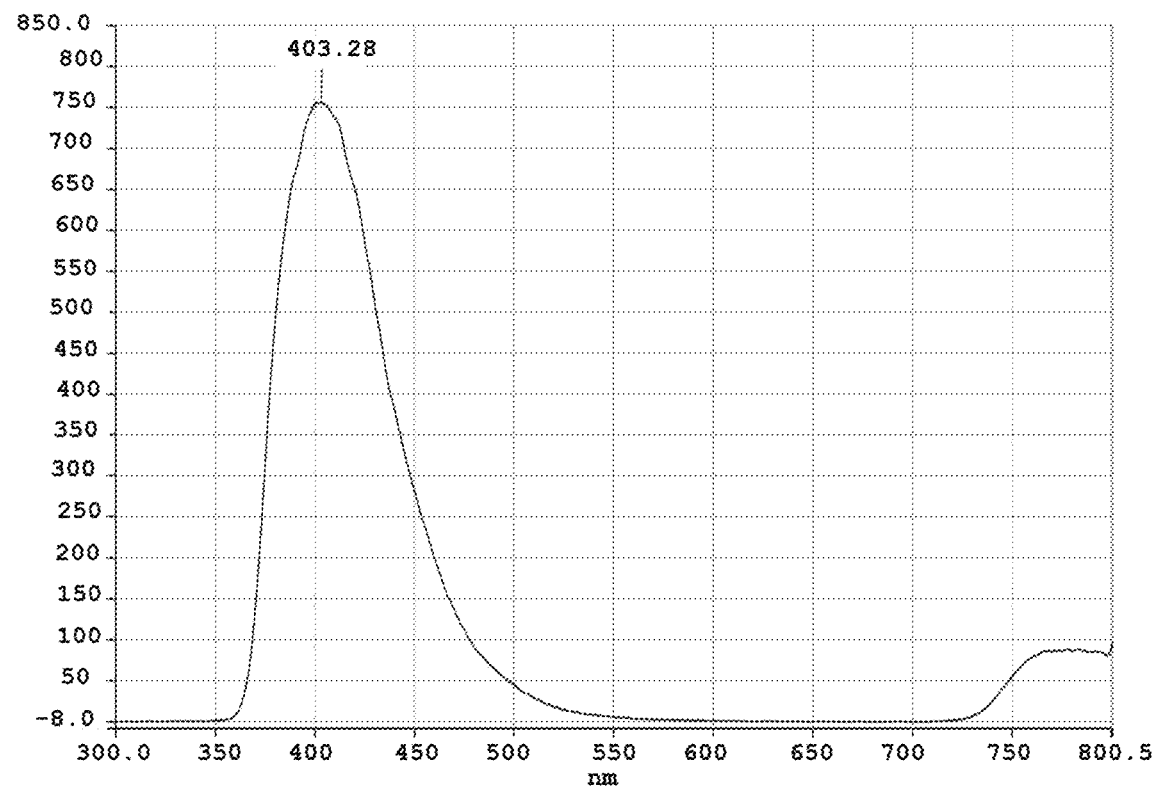

[Figure 18]
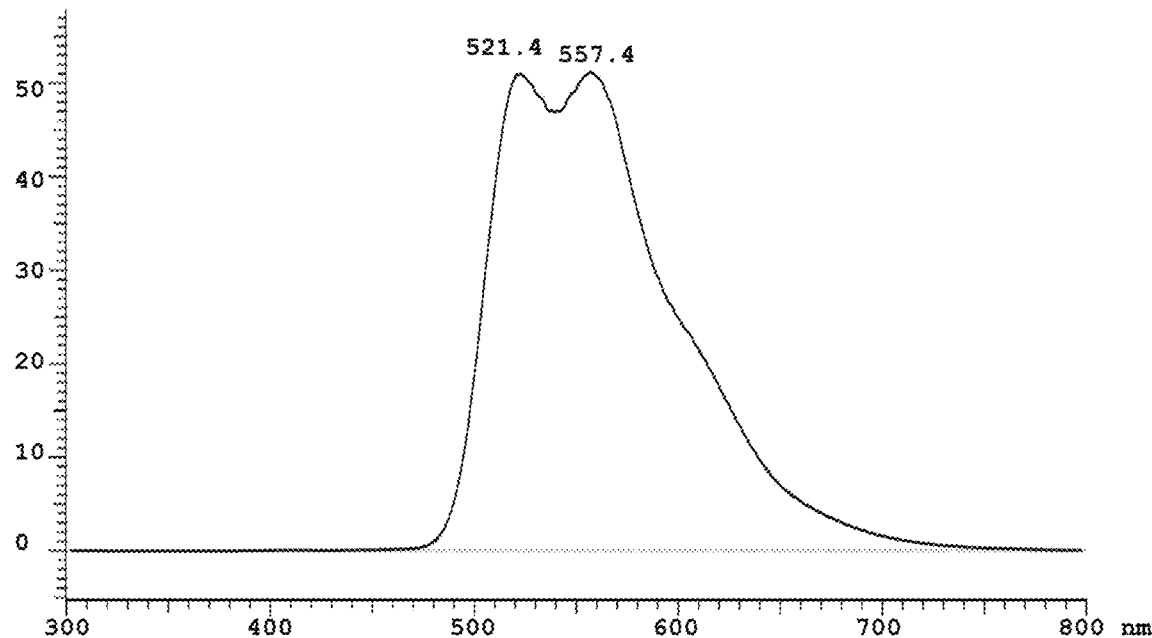
[Figure 19]
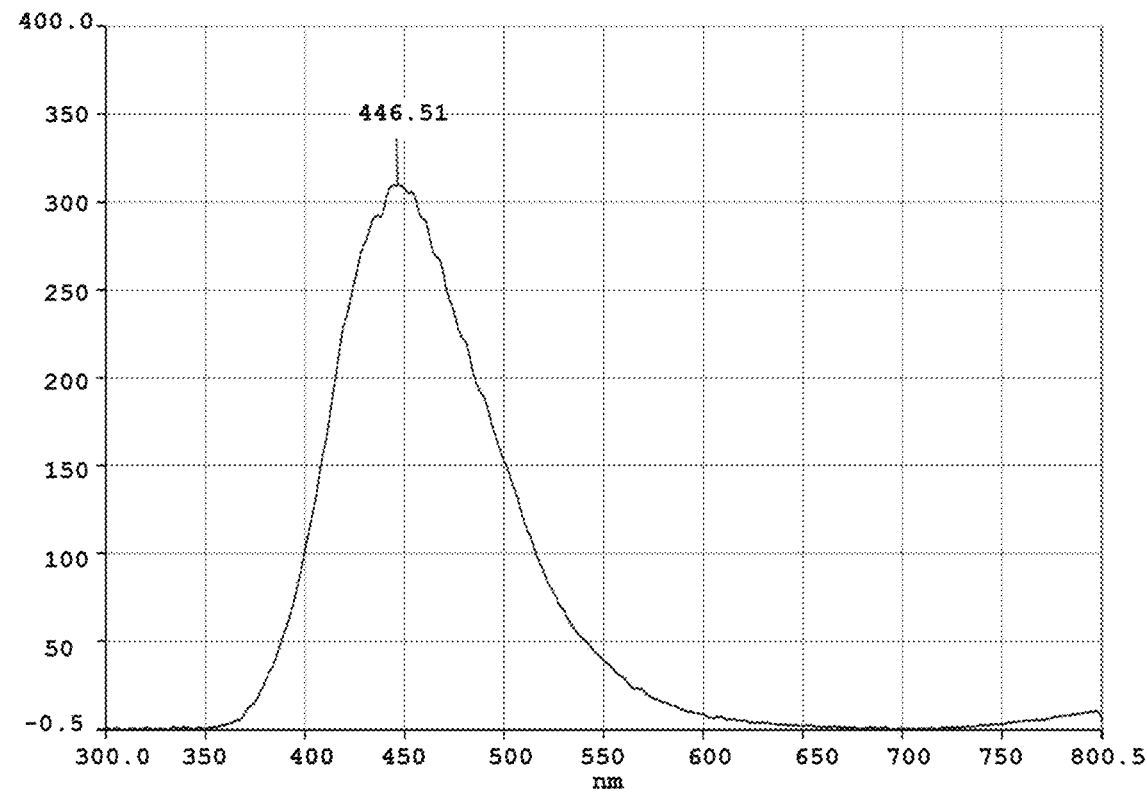

[Figure 20]
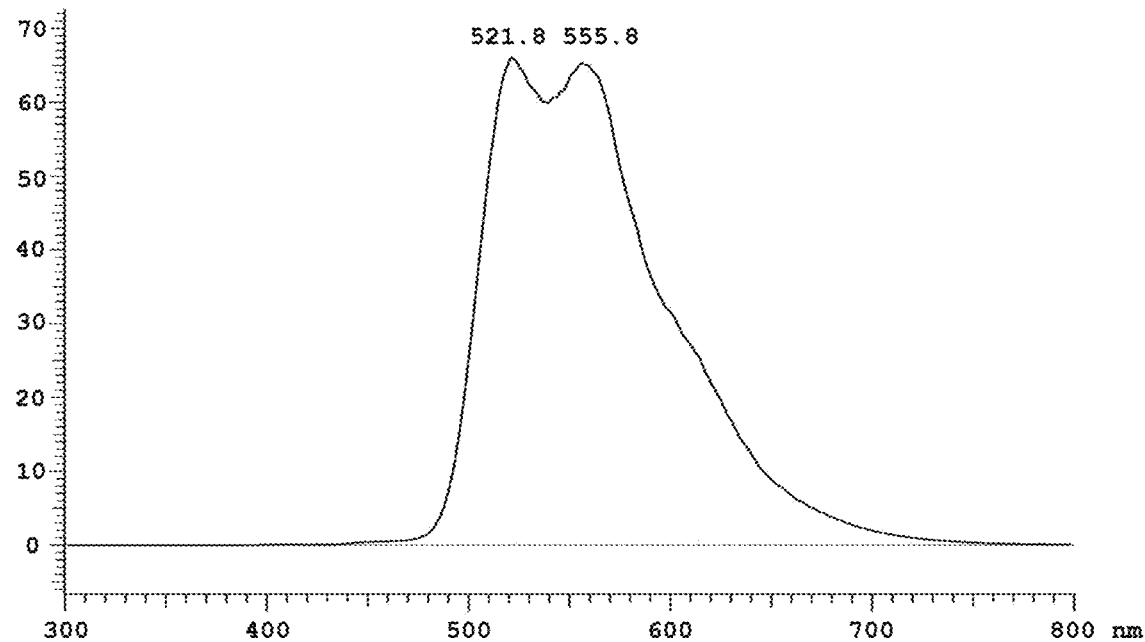
[Figure 21]
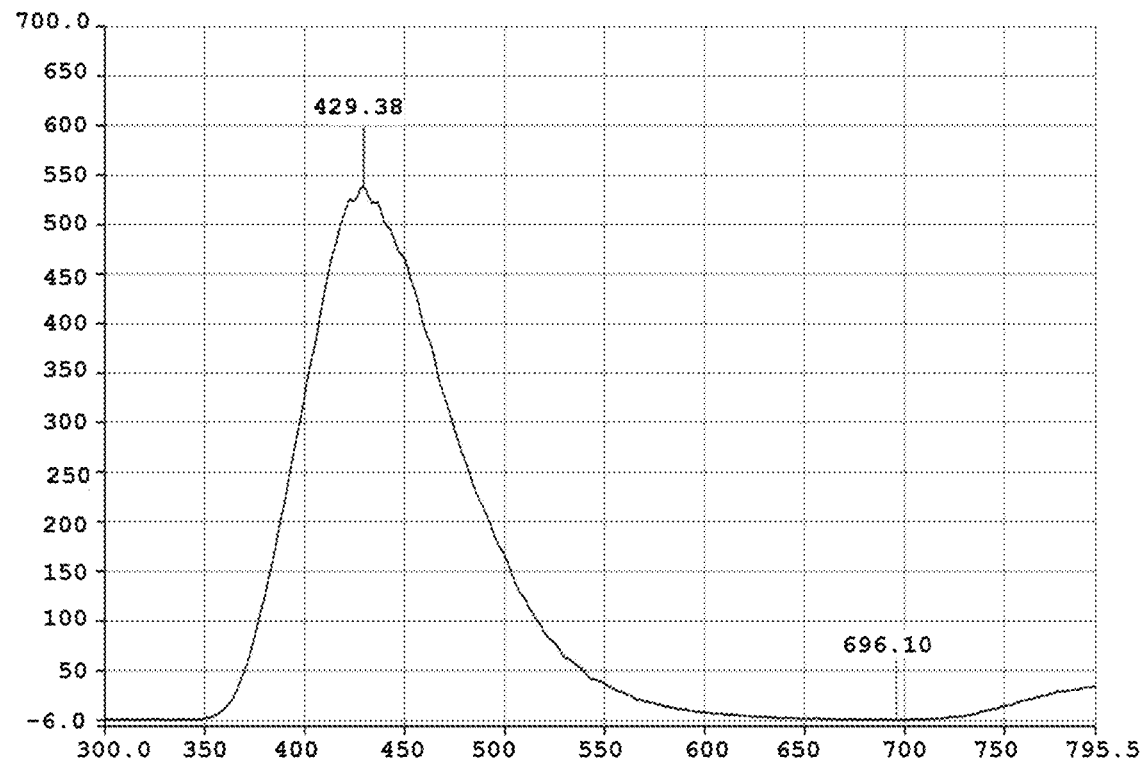

[Figure 22]
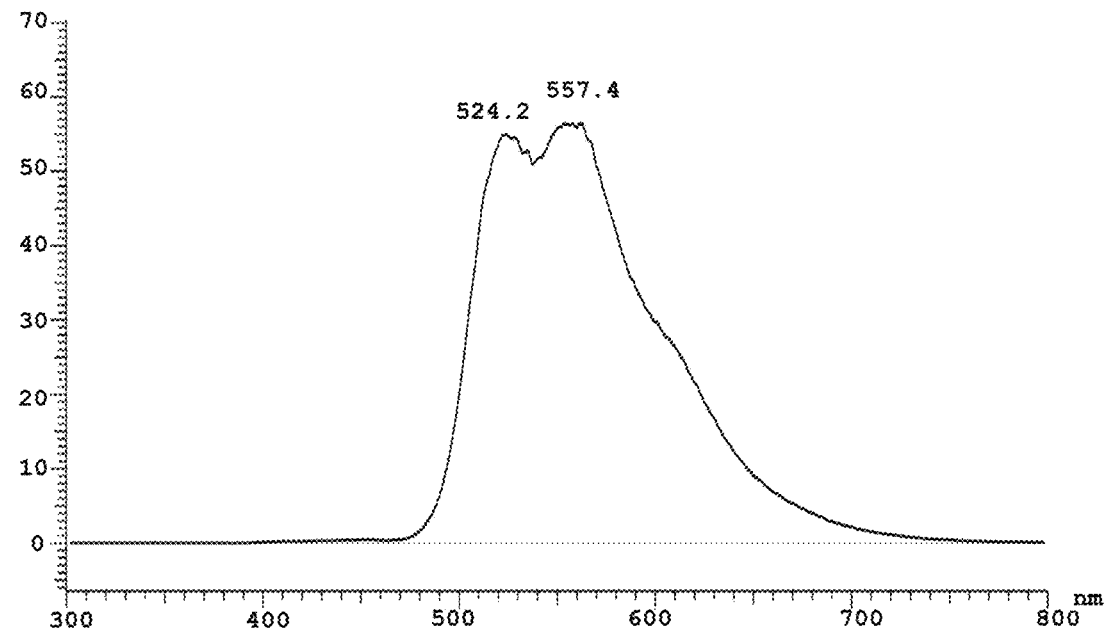
[Figure 23]
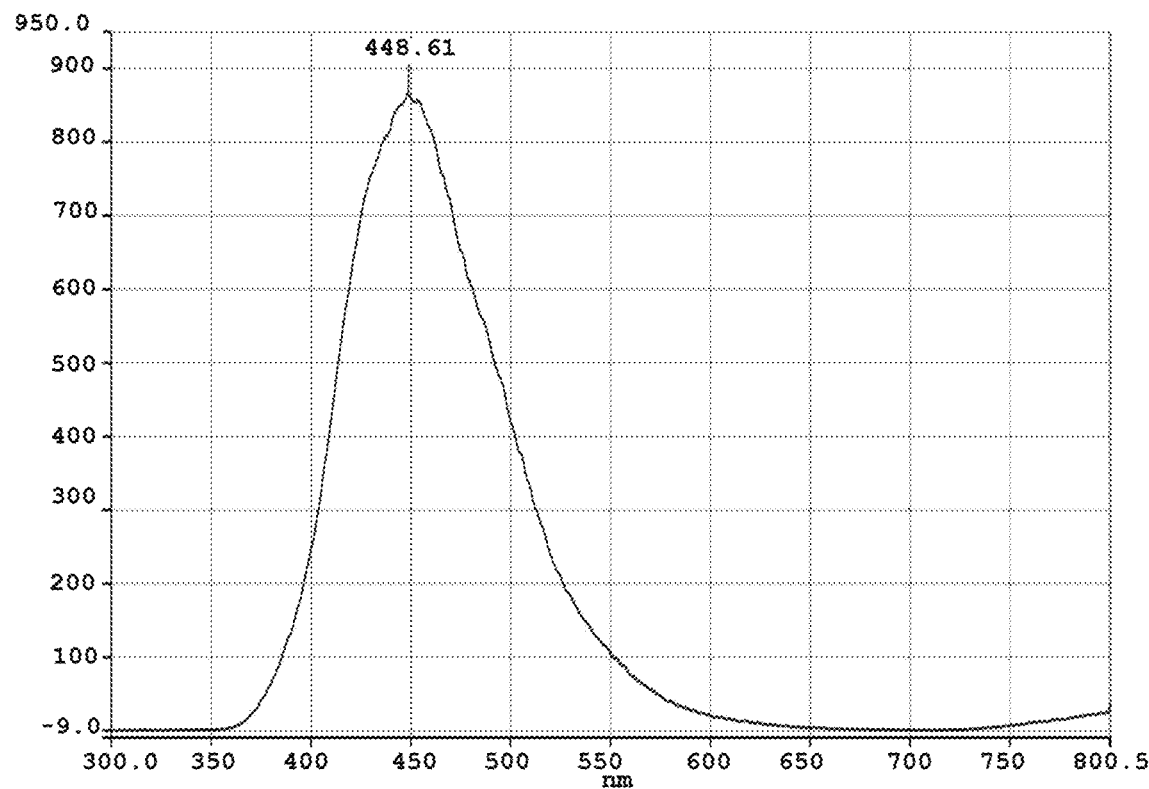

[Figure 24]
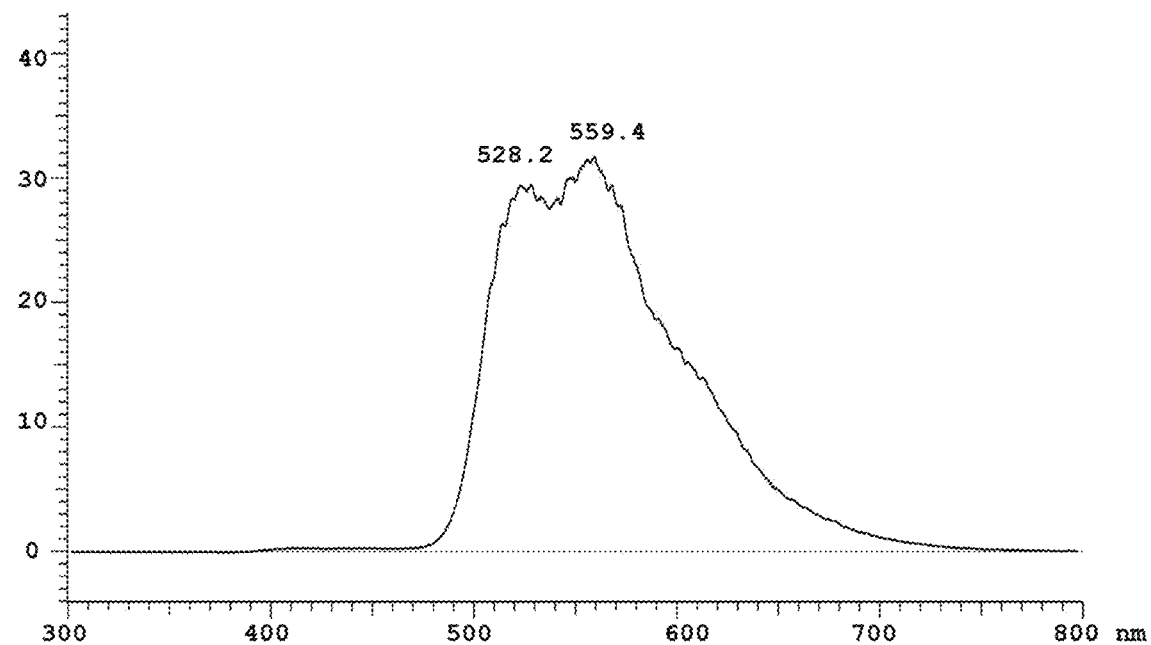
[Figure 25]
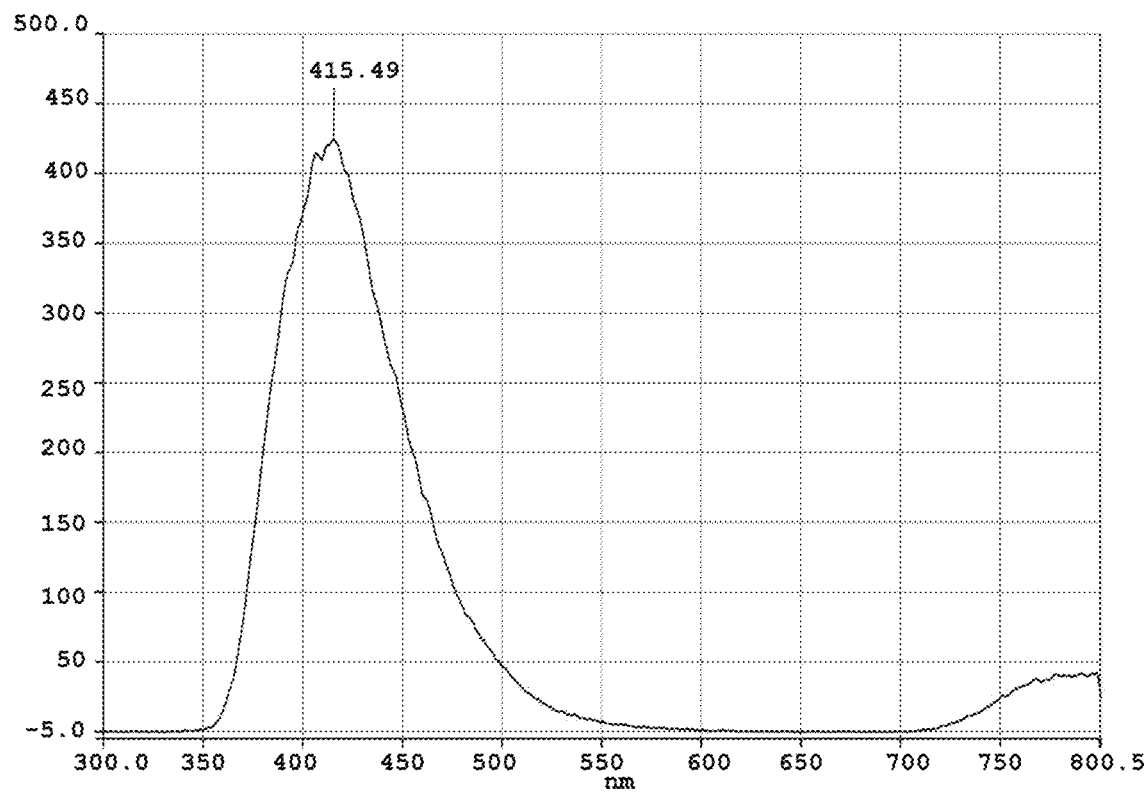

[Figure 26]
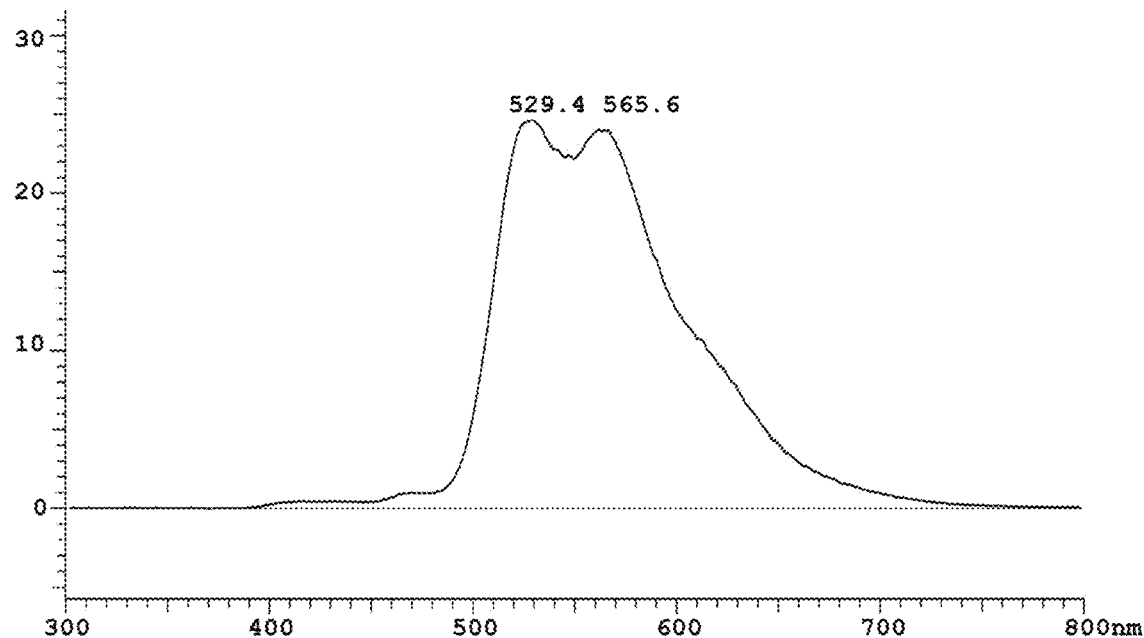
[Figure 27]
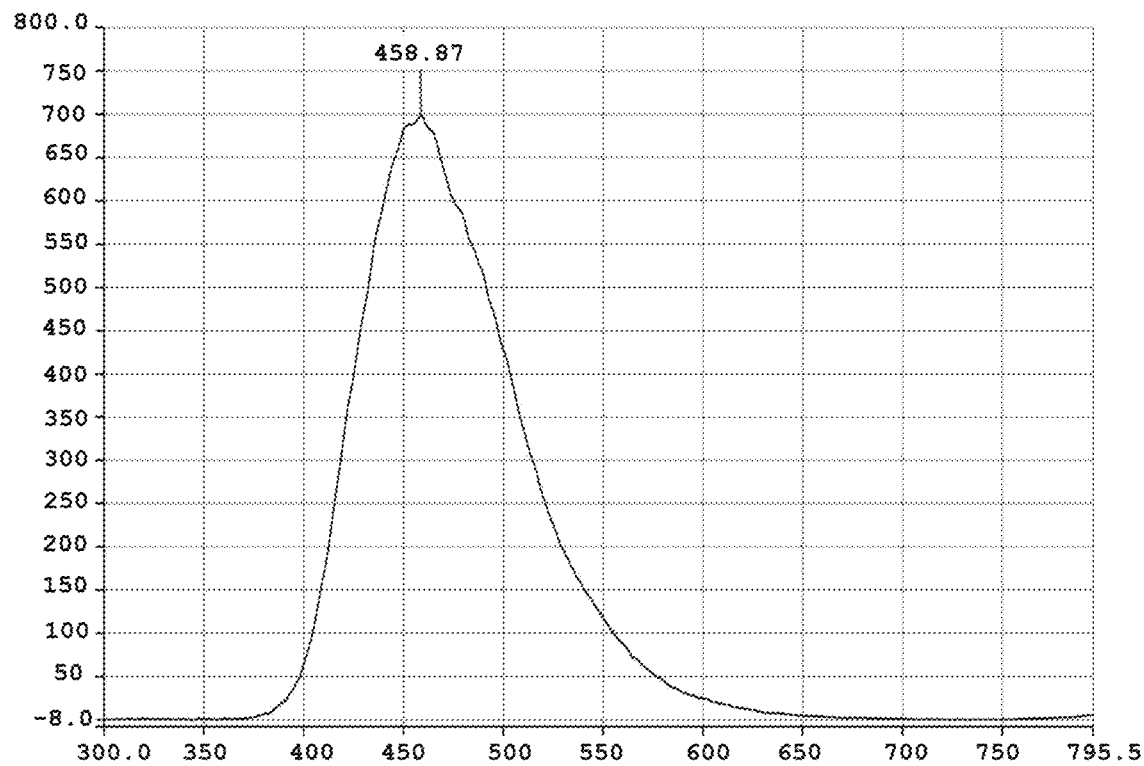

[Figure 28]
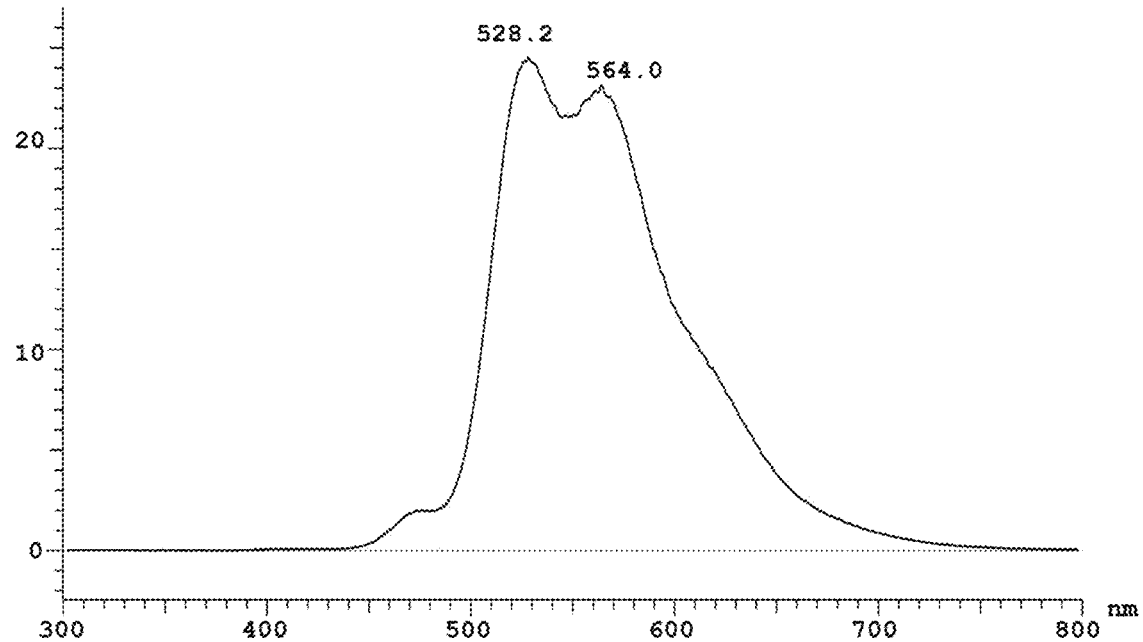
[Figure 29]
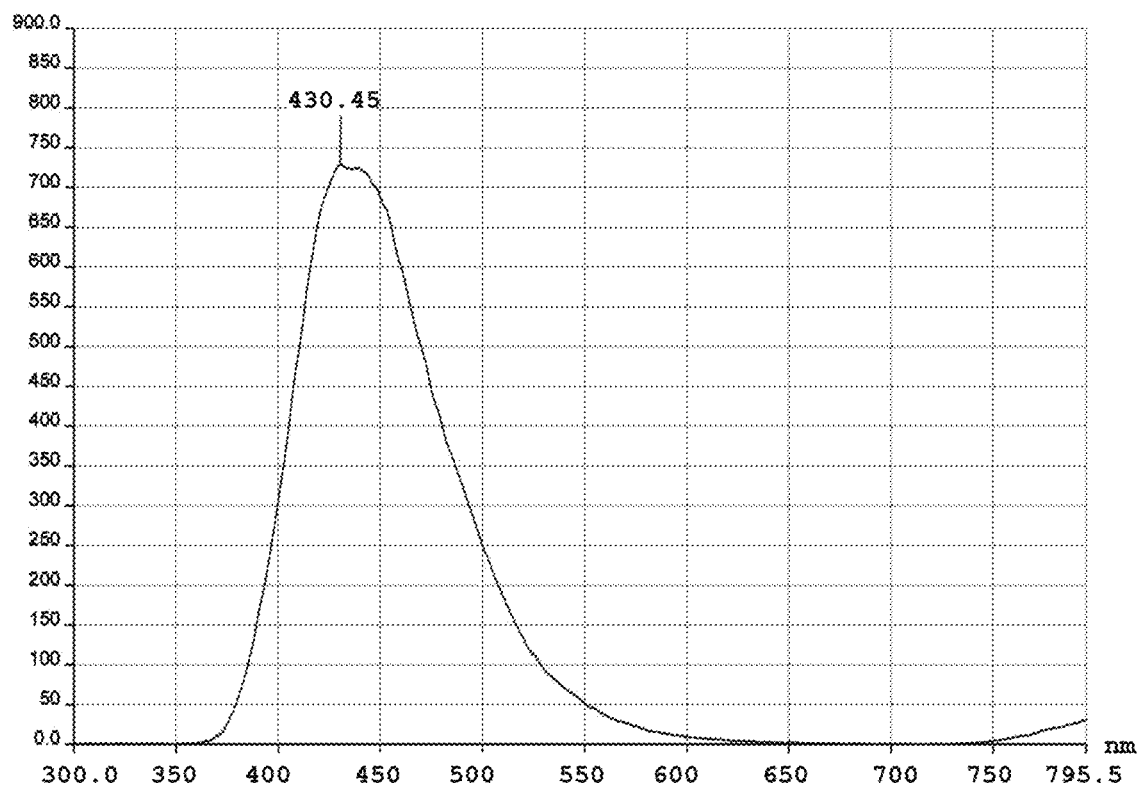

[Figure 30]
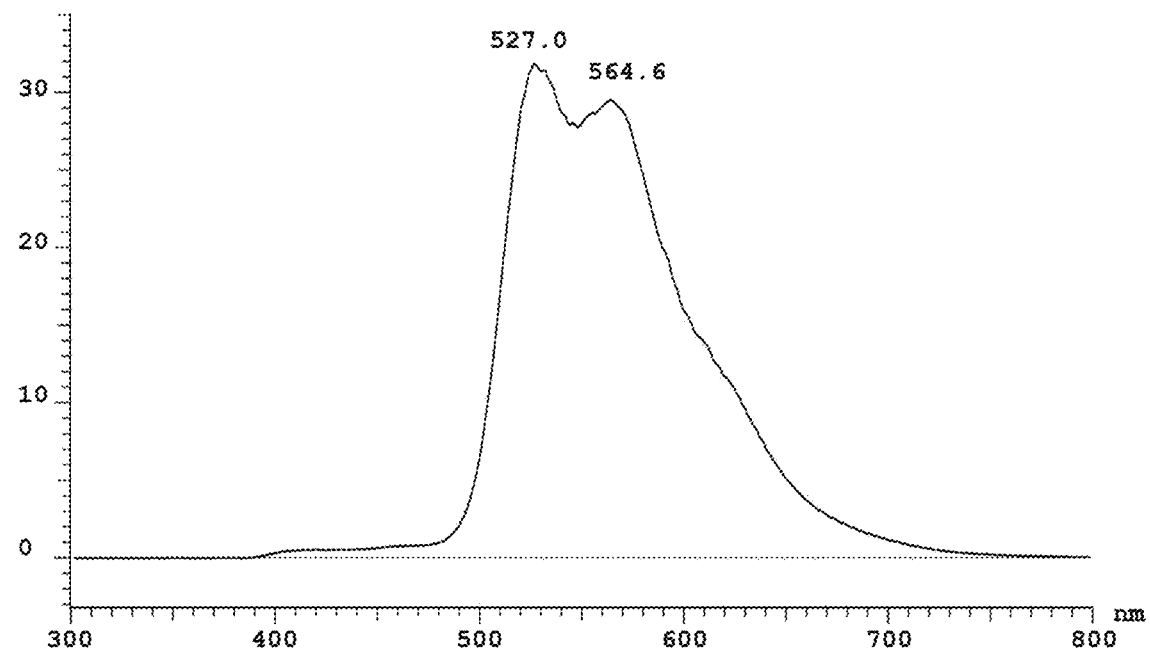
[Figure 31]
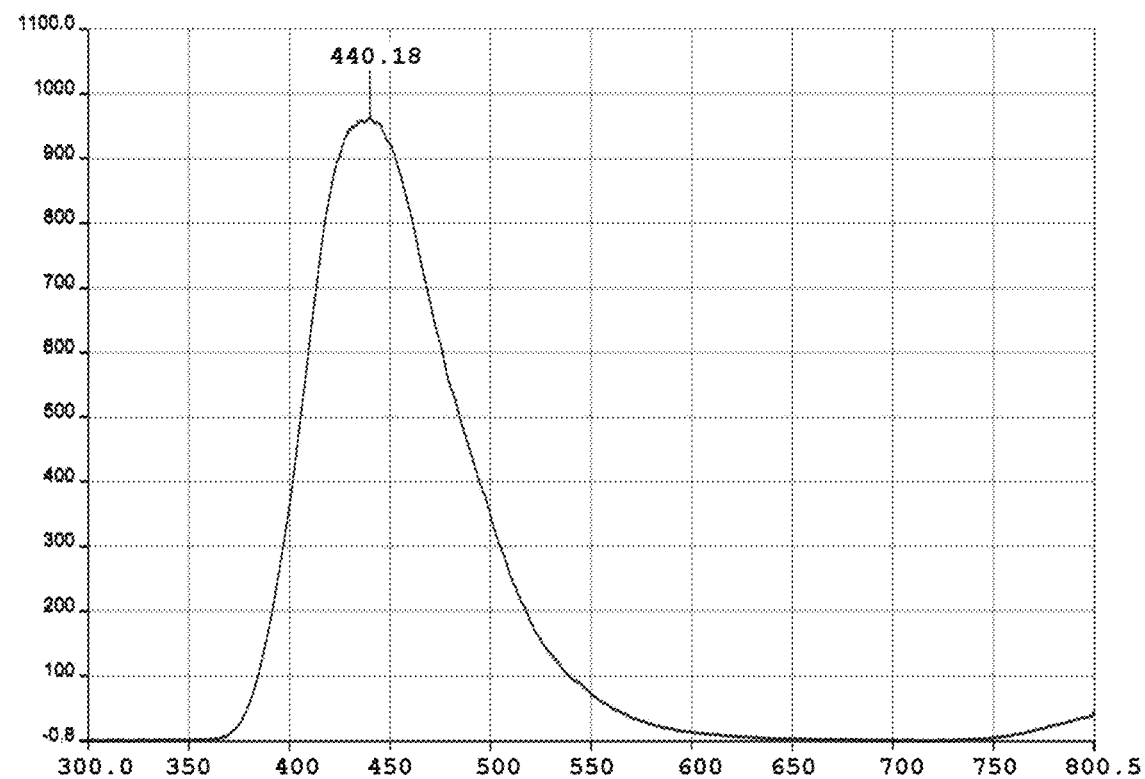

[Figure 32]
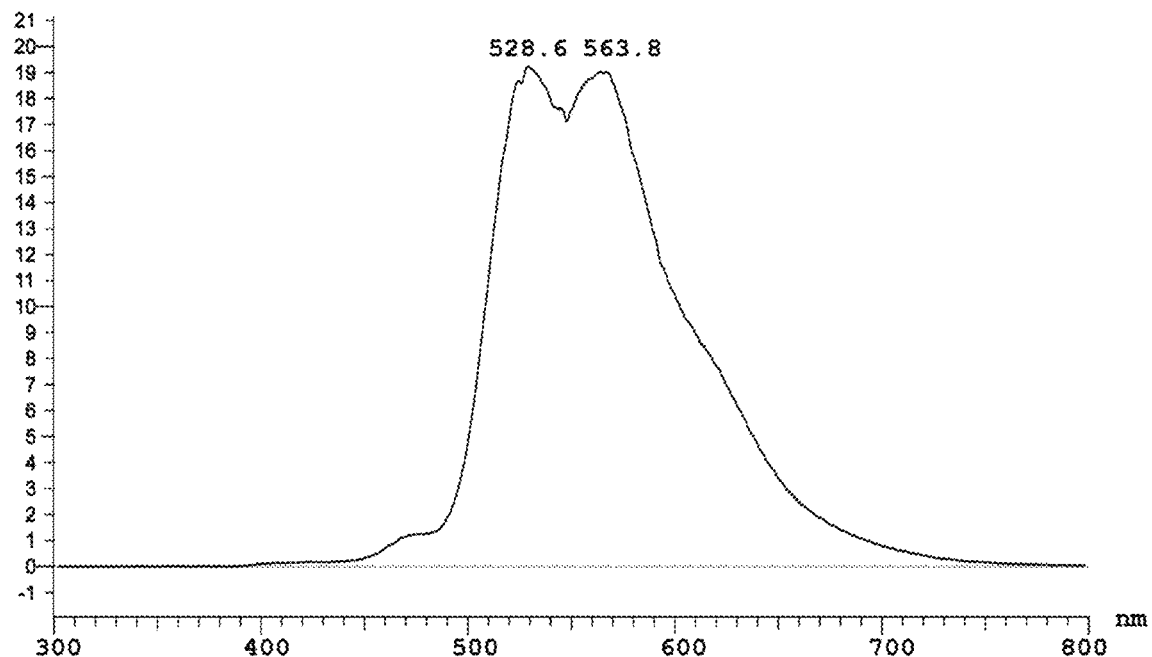
[Figure 33]
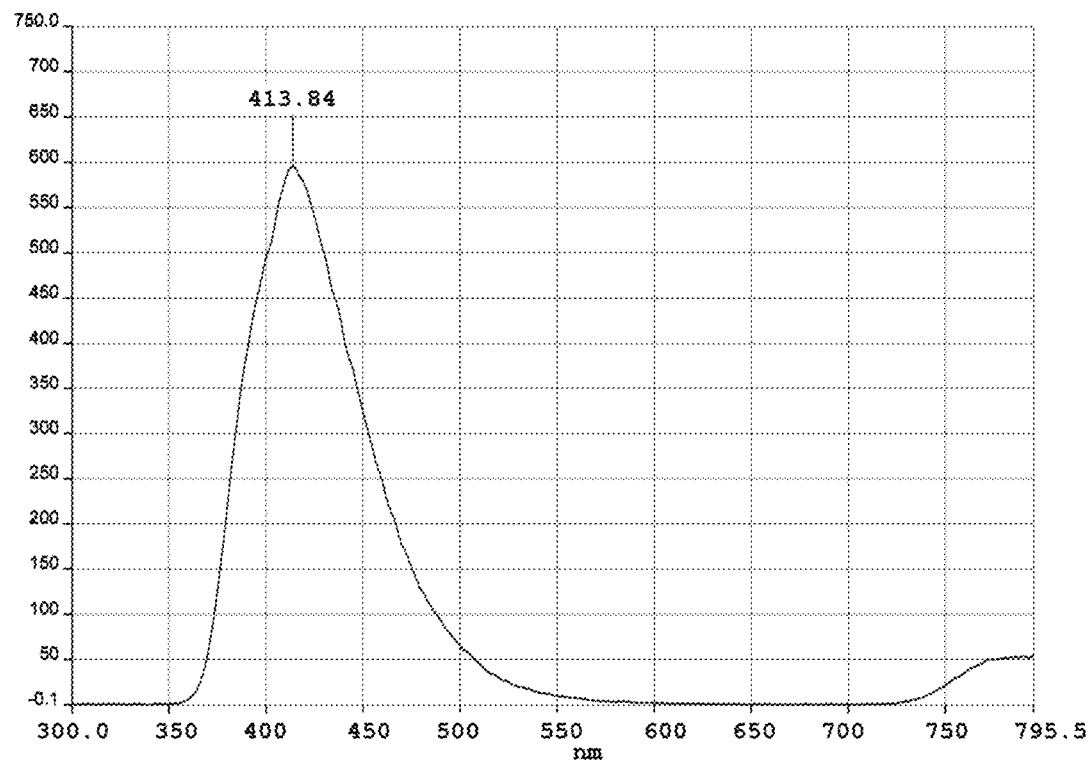

[Figure 34]
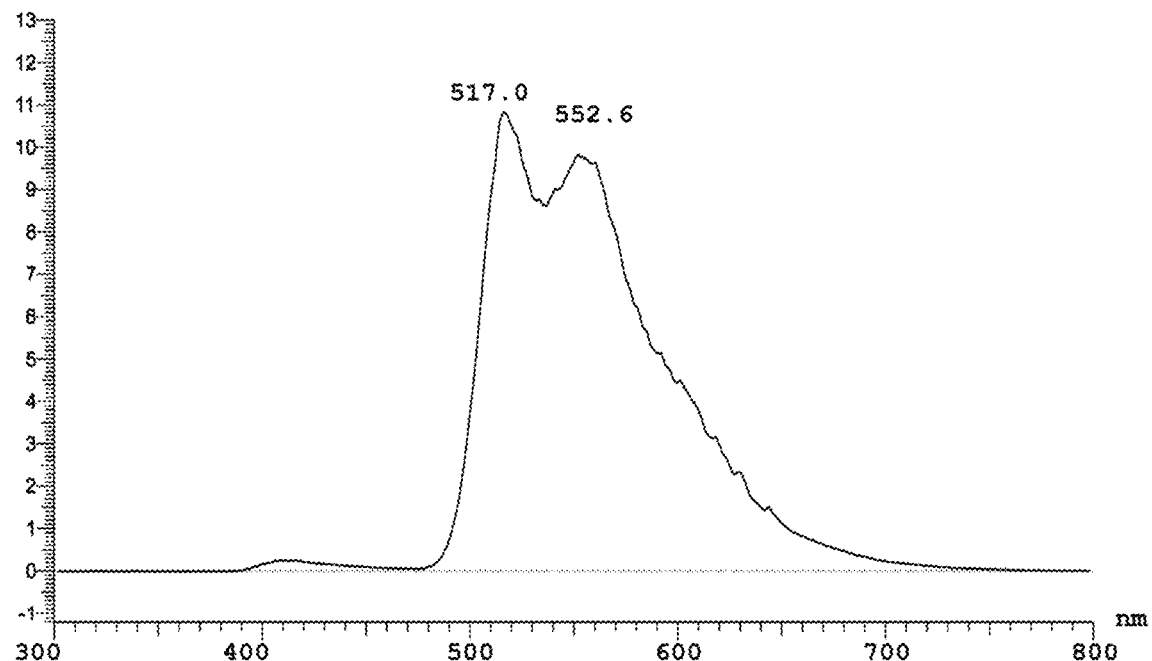
[Figure 35]
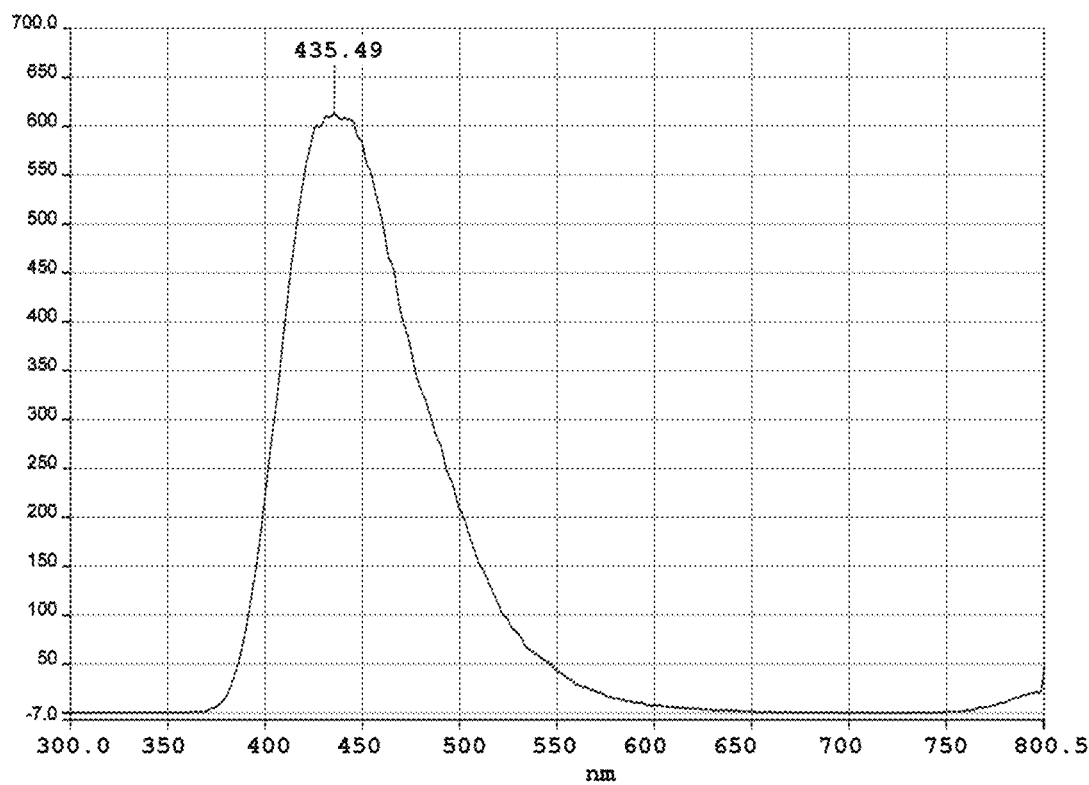

HETEROCYCLIC COMPOUND AND ORGANIC LIGHT EMITTING ELEMENT USING SAME

TECHNICAL FIELD

This application claims priority to and the benefit of Korean Patent Application No. 10-2015-0156174 filed in the Korean Intellectual Property Office on Nov. 9, 2015, the entire contents of which are incorporated herein by reference.

The present application relates to a hetero-cyclic compound and an organic light emitting device using the same.

BACKGROUND ART

An electroluminescence device is a kind of self-emitting type display device, and has an advantage in that the viewing angle is wide, the contrast is excellent, and the response speed is fast.

An organic light emitting device has a structure in which an organic thin film is disposed between two electrodes. When a voltage is applied to an organic light emitting device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, service life, or efficiency of the organic light emitting device, there is a continuous need for developing a material for an organic thin film.

DISCLOSURE

Technical Problem

It is necessary to perform studies on an organic light emitting device including a compound having a chemical structure, which may satisfy conditions required for a material which is available for the organic light emitting device, for example, appropriate energy levels, electrochemical stability, thermal stability, and the like, and may perform various functions required for the organic light emitting device according to the substituent.

Technical Solution

An exemplary embodiment of the present application provides a hetero-cyclic compound represented by the following Chemical Formula 1:

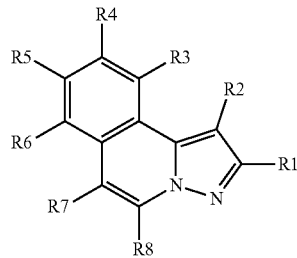

[Chemical Formula 1]

In Chemical Formula 1, at least one of R1 to R8 is represented by -L-Ar, and the others are each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R''; —P(=O)RR'; and an amine group which is unsubstituted or substituted with a $C_1$ to $C_{20}$ alkyl group, a substituted or unsubstituted $C_6$ to $C_{60}$ aryl group, or a substituted or unsubstituted $C_2$ to $C_{60}$ heteroaryl group, or two or more adjacent groups are bonded to each other to form a substituted or unsubstituted aliphatic or aromatic hydrocarbon ring, L is a substituted or unsubstituted $C_6$ to $C_{60}$ arylene group, Ar is represented by any one of the following Chemical Formulae 2 to 7,

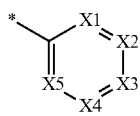

[Chemical Formula 2]

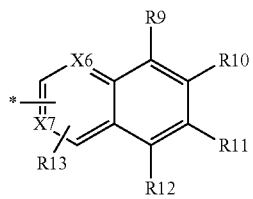

[Chemical Formula 3]

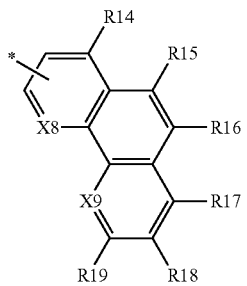

[Chemical Formula 4]

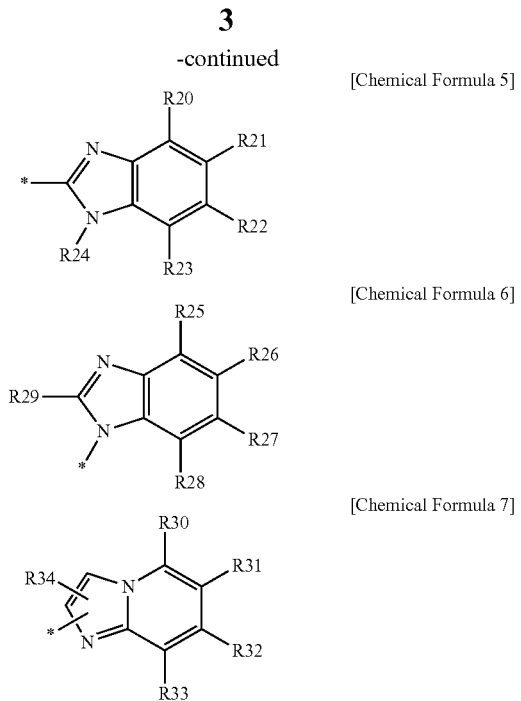

[Chemical Formula 5]

[Chemical Formula 6]

[Chemical Formula 7]

In Chemical Formulae 2 to 7, at least one of X1 to X5 is N, and the others are N or CR, at least one of X6 and X7 is N, and the other is N or CR, at least one of X8 and X9 is N, and the other is N or CR, R9 to R34 are the same as or different from each other, and are each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a substituted or unsubstituted $C_2$ to $C_{60}$ heteroaryl group, or two or more adjacent groups are bonded to each other to form a substituted or unsubstituted aliphatic or aromatic hydrocarbon ring, R, R', and R" are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, and

* denotes a position bonded to L.

Further, another exemplary embodiment of the present application provides an organic light emitting device comprising: a positive electrode; a negative electrode; and an organic material layer having one or more layers disposed between the positive electrode and the negative electrode, in which one or more layers of the organic material layer comprise the hetero-cyclic compound.

Advantageous Effects

A hetero-cyclic compound according to an exemplary embodiment of the present application may be used as a material for an organic material layer of an organic light emitting device. The hetero-cyclic compound may be used as a material for a hole injection layer, a hole transporting layer, a light emitting layer, an electron transporting layer, an electron injection layer, and the like in an organic light emitting device. In particular, the hetero-cyclic compound represented by Chemical Formula 1 may be used as a material for an electron transporting layer, a hole transporting layer, or a light emitting layer of an organic light emitting device. In addition, when the hetero-cyclic compound represented by Chemical Formula 1 is used for an organic light emitting device, the driving voltage of the device may be lowered, the light efficiency of the device may be improved, and the service life characteristics of the device may be improved due to the thermal stability of the compound.

DESCRIPTION OF DRAWINGS

FIGS. 1 to 3 each are a view schematically illustrating a stacking structure of an organic light emitting device according to an exemplary embodiment of the present application.

FIG. 4 illustrates a measurement graph of LTPL of Compound 5.

FIG. 5 illustrates a measurement graph of PL of Compound 5.

FIG. 6 illustrates a measurement graph of LTPL of Compound 7.

FIG. 7 illustrates a measurement graph of PL of Compound 7.

FIG. 8 illustrates a measurement graph of LTPL of Compound 9.

FIG. 9 illustrates a measurement graph of PL of Compound 9.

FIG. 10 illustrates a measurement graph of LTPL of Compound 10.

FIG. 11 illustrates a measurement graph of PL of Compound 10.

FIG. 12 illustrates a measurement graph of LTPL of Compound 11.

FIG. 13 illustrates a measurement graph of PL of Compound 11.

FIG. 14 illustrates a measurement graph of LTPL of Compound 12.

FIG. 15 illustrates a measurement graph of PL of Compound 12.

FIG. 16 illustrates a measurement graph of LTPL of Compound 20.

FIG. 17 illustrates a measurement graph of PL of Compound 20.

FIG. 18 illustrates a measurement graph of LTPL of Compound 33.

FIG. 19 illustrates a measurement graph of PL of Compound 33.

FIG. 20 illustrates a measurement graph of LTPL of Compound 34.

FIG. 21 illustrates a measurement graph of PL of Compound 34.

FIG. 22 illustrates a measurement graph of LTPL of Compound 35.

FIG. 23 illustrates a measurement graph of PL of Compound 35.

FIG. 24 illustrates a measurement graph of LTPL of Compound 52.

FIG. 25 illustrates a measurement graph of PL of Compound 52.

FIG. 26 illustrates a measurement graph of LTPL of Compound 117.

FIG. 27 illustrates a measurement graph of PL of Compound 117.

FIG. 28 illustrates a measurement graph of LTPL of Compound 122.

FIG. 29 illustrates a measurement graph of PL of Compound 122.

FIG. 30 illustrates a measurement graph of LTPL of Compound 123.

FIG. 31 illustrates a measurement graph of PL of Compound 123.

FIG. 32 illustrates a measurement graph of LTPL of Compound 124.

FIG. 33 illustrates a measurement graph of PL of Compound 124.

FIG. 34 illustrates a measurement graph of LTPL of Compound 169.

FIG. 35 illustrates a measurement graph of PL of Compound 169.

EXPLANATION OF REFERENCE NUMERALS AND SYMBOLS

100: Substrate
200: Positive electrode
300: Organic material layer
301: Hole injection layer
302: Hole transporting layer
303: Light emitting layer
304: Hole blocking layer
305: Electron transporting layer
306: Electron injection layer
400: Negative electrode

BEST MODE

Hereinafter, the present application will be described in detail.

A hetero-cyclic compound according to an exemplary embodiment of the present application is represented by Chemical Formula 1. More specifically, the hetero-cyclic compound represented by Chemical Formula 1 may be used as a material for an organic material layer of an organic light emitting device by the structural characteristics of the core structure and the substituent as described above.

According to an exemplary embodiment of the present application, Chemical Formula 1 may be represented by any one of the following Chemical Formulae 8 to 10.

[Chemical Formula 8]

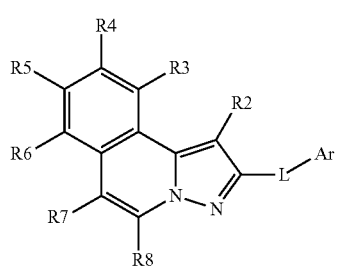

[Chemical Formula 9]

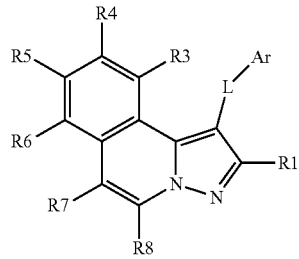

[Chemical Formula 10]

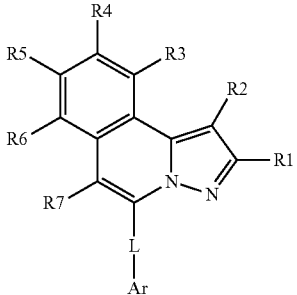

In Chemical Formulae 8 to 10, R1 to R8, L, and Ar are the same as the definitions in Chemical Formula 1.

In an exemplary embodiment of the present application, at least one of R1 to R8 is represented by -L-Ar, and the others are each independently hydrogen; deuterium; a substituted or unsubstituted $C_1$ to $C_{60}$ alkyl group; or a substituted or unsubstituted $C_6$ to $C_{60}$ aryl group.

In the present application, the substituents of Chemical Formulae 1 to 10 will be more specifically described as follows.

In the present specification, "substituted or unsubstituted" means being unsubstituted or substituted with one or more substituents selected from the group consisting of deuterium; a halogen group; —CN; a straight or branched $C_1$ to $C_{60}$ alkyl group; a straight or branched $C_2$ to $C_{60}$ alkenyl group; a straight or branched $C_2$ to $C_{60}$ alkynyl group; a monocyclic or polycyclic $C_3$ to $C_{60}$ cycloalkyl group; a monocyclic or polycyclic $C_2$ to $C_{60}$ heterocycloalkyl group; a monocyclic or polycyclic $C_6$ to $C_{60}$ aryl group; a monocyclic or polycyclic $C_2$ to $C_{60}$ heteroaryl group; —SiRR'R''; —P(=O)RR'; a $C_1$ to $C_{20}$ alkylamine group; a monocyclic or polycyclic $C_6$ to $C_{60}$ arylamine group; and a monocyclic or polycyclic $C_2$ to $C_{60}$ heteroarylamine group, or being unsubstituted or substituted with a substituent to which two or more among the substituents are bonded, or being unsubstituted or substituted with a substituent to which two or more substituents selected from the substituents are linked. For example, "the substituent to which two or more substituents are linked" may be a biphenyl group. That is, the biphenyl group may also be an aryl group, and may be interpreted as a substituent to which two phenyl groups are linked. The additional substituents may also be additionally substituted. R, R', and R'' are the same as or different from each other, and are each independently hydrogen; deuterium; —CN; a substituted or unsubstituted, straight or branched $C_1$ to $C_{60}$ alkyl group; a substituted or unsubstituted, monocyclic or polycyclic $C_3$ to $C_{60}$ cycloalkyl group; a substituted or unsubstituted, monocyclic or polycyclic $C_6$ to $C_{60}$ aryl group; or a substituted or unsubstituted, monocyclic or polycyclic $C_2$ to $C_{60}$ heteroaryl group.

According to an exemplary embodiment of the present application, the "substituted or unsubstituted" means being unsubstituted or substituted with one or more substituents selected from the group consisting of deuterium, a halogen group, —CN, —SiRR'R", —P(═O)RR', a straight or branched $C_1$ to $C_{20}$ alkyl group, a monocyclic or polycyclic $C_6$ to $C_{60}$ aryl group, and a monocyclic or polycyclic $C_2$ to $C_{60}$ heteroaryl group, and R, R', and R" are the same as or different from each other, and are each independently hydrogen; deuterium; —CN; a straight or branched $C_1$ to $C_{60}$ alkyl group which is unsubstituted or substituted with deuterium, a halogen group, —CN, a straight or branched $C_1$ to $C_{20}$ alkyl group, a monocyclic or polycyclic $C_6$ to $C_{60}$ aryl group, and a monocyclic or polycyclic $C_2$ to $C_{60}$ heteroaryl group; a monocyclic or polycyclic $C_3$ to $C_{60}$ cycloalkyl group which is unsubstituted or substituted with deuterium, halogen, —CN, a straight or branched $C_1$ to $C_{20}$ alkyl group, a monocyclic or polycyclic $C_6$ to $C_{60}$ aryl group, and a monocyclic or polycyclic $C_2$ to $C_{60}$ heteroaryl group; a monocyclic or polycyclic $C_6$ to $C_{60}$ aryl group which is unsubstituted or substituted with deuterium, halogen, —CN, a straight or branched $C_1$ to $C_{20}$ alkyl group, a monocyclic or polycyclic $C_6$ to $C_{60}$ aryl group, and a monocyclic or polycyclic $C_2$ to $C_{60}$ heteroaryl group; or a monocyclic or polycyclic $C_2$ to $C_{60}$ heteroaryl group which is unsubstituted or substituted with deuterium, halogen, —CN, a straight or branched $C_1$ to $C_{20}$ alkyl group, a monocyclic or polycyclic $C_6$ to $C_{60}$ aryl group, and a monocyclic or polycyclic $C_2$ to $C_{60}$ heteroaryl group.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the halogen may be fluorine, chlorine, bromine or iodine.

In the present specification, the alkyl group comprises a straight-chain or branched-chain having 1 to 60 carbon atoms, and may be additionally substituted with another substituent. The number of carbon atoms of the alkyl group may be 1 to 60, specifically 1 to 40, and more specifically 1 to 20. Specific examples thereof comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group, and the like, but are not limited thereto.

In the present specification, the alkenyl group comprises a straight-chain or branched-chain having 2 to 60 carbon atoms, and may be additionally substituted with another substituent. The number of carbon atoms of the alkenyl group may be 2 to 60, specifically 2 to 40, and more specifically 2 to 20. Specific examples thereof comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group, and the like, but are not limited thereto.

In the present specification, the alkynyl group comprises a straight-chain or branched-chain having 2 to 60 carbon atoms, and may be additionally substituted with another substituent. The number of carbon atoms of the alkynyl group may be 2 to 60, specifically 2 to 40, and more specifically 2 to 20.

In the present specification, the cycloalkyl group comprises a monocycle or polycycle having 3 to 60 carbon atoms, and may be additionally substituted with another substituent. Here, the polycycle means a group in which a cycloalkyl group is directly linked to or fused with another cyclic group. Here, another cyclic group may also be a cycloalkyl group, but may also be another kind of cyclic group, for example, a heterocycloalkyl group, an aryl group, a heteroaryl group, and the like. The number of carbon atoms of the cycloalkyl group may be 3 to 60, specifically 3 to 40, and more specifically 5 to 20. Specific examples thereof comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group, and the like, but are not limited thereto.

In the present specification, the heterocycloalkyl group comprises O, S, Se, N, or Si as a heteroatom, includes a monocycle or polycycle having 2 to 60 carbon atoms, and may be additionally substituted with another substituent. Here, the polycycle means a group in which a heterocycloalkyl group is directly linked to or fused with another cyclic group. Here, another cyclic group may also be a heterocycloalkyl group, but may also be another kind of cyclic group, for example, a cycloalkyl group, an aryl group, a heteroaryl group, and the like. The number of carbon atoms of the heterocycloalkyl group may be 2 to 60, specifically 2 to 40, and more specifically 3 to 20.

In the present specification, the aryl group comprises a monocycle or polycycle having 6 to 60 carbon atoms, and may be additionally substituted with another substituent. Here, the polycycle means a group in which an aryl group is directly linked to or fused with another cyclic group. Here, another cyclic group may also be an aryl group, but may also be another kind of cyclic group, for example, a cycloalkyl group, a heterocycloalkyl group, a heteroaryl group, and the like. The aryl group comprises a spiro group. The number of carbon atoms of the aryl group may be 6 to 60, specifically 6 to 40, and more specifically 6 to 25. Specific examples of the aryl group comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof, and the like, but are not limited thereto.

In the present specification, the spiro group is a group comprising a spiro structure, and may have 15 to 60 carbon atoms. For example, the spiro group may comprise a structure in which a 2,3-dihydro-1H-indene group or a cyclohexane group is spiro-bonded to a fluorenyl group. Specifically, the Spiro group may include any one of the groups of the following structural formulae.

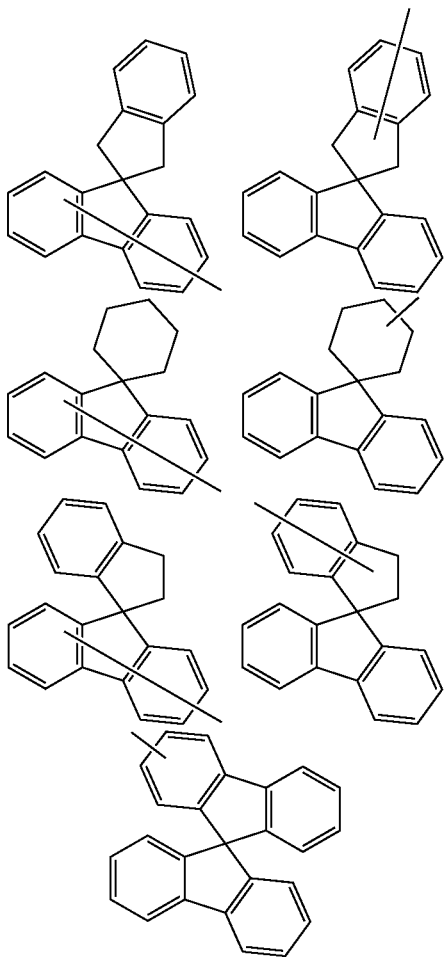

In the present specification, the heteroaryl group comprises S, 0, Se, N, or Si as a heteroatom, comprises a monocycle or polycycle having 2 to 60 carbon atoms, and may be additionally substituted with another substituent. Here, the polycycle means a group in which a heteroaryl group is directly linked to or fused with another cyclic group. Here, another cyclic group may also be a heteroaryl group, but may also be another kind of cyclic group, for example, a cycloalkyl group, a heterocycloalkyl group, an aryl group, and the like. The number of carbon atoms of the heteroaryl group may be 2 to 60, specifically 2 to 40, and more specifically 3 to 25. Specific examples of the heteroaryl group comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxinyl group, a triazinyl group, a tetrazinyl group, a quinolyl group, an isoquinolyl group, a quinazolinyl group, an isoquinazolinyl group, a quinozolilyl group, a naphthyridyl group, an acridinyl group, a phenanthridinyl group, an imidazopyridinyl group, a diaza naphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi (dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepin group, a 9,10-dihydroacridinyl group, a phenanthrazinyl group, a phenothiazinyl group, a phthalazinyl group, a naphthylidinyl group, a phenanthrolinyl group, a benzo[c][1,2,5]thiadiazolyl group, a 5,10-dihydrodibenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group, and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and the number of carbon atoms thereof is not particularly limited, but is preferably 1 to 30. Specific examples of the amine group comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group, and the like, but are not limited thereto.

In the present specification, the arylene group means that there are two bonding positions in an aryl group, that is, a divalent group. The above-described description on the aryl group may be applied to the arylene group, except for a divalent arylene group. Further, the heteroarylene group means that there are two bonding positions in a heteroaryl group, that is, a divalent group. The above-described description on the heteroaryl group may be applied to the heteroarylene group, except for a divalent heteroarylene group.

According to an exemplary embodiment of the present application, Chemical Formula 1 may be represented by any one of the following compounds, but is not limited thereto.

5
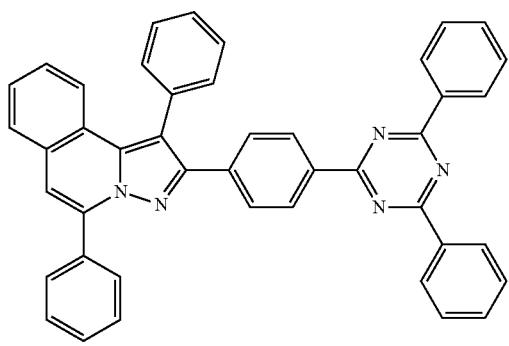
6
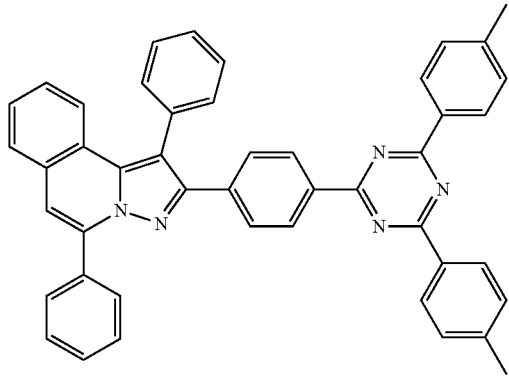
7
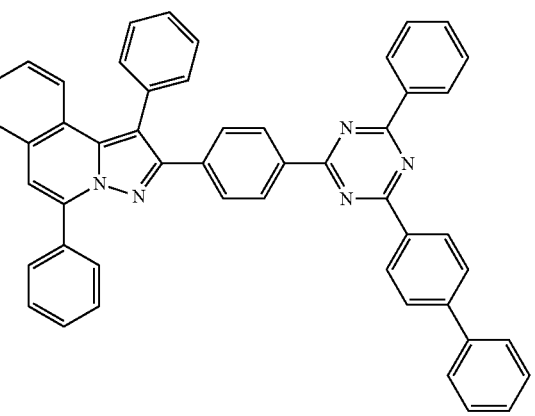
8
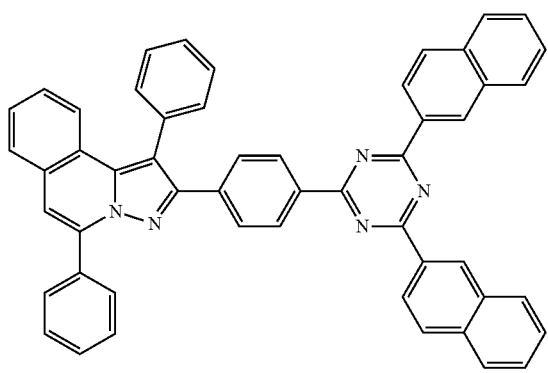
9
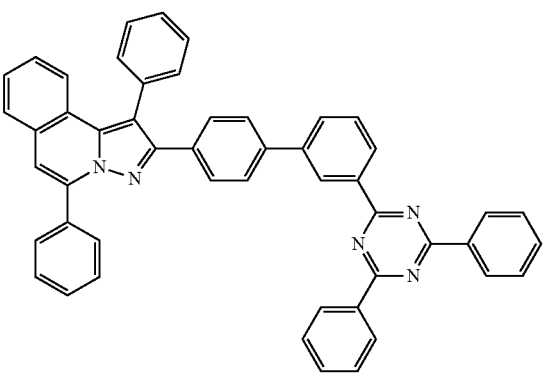
10
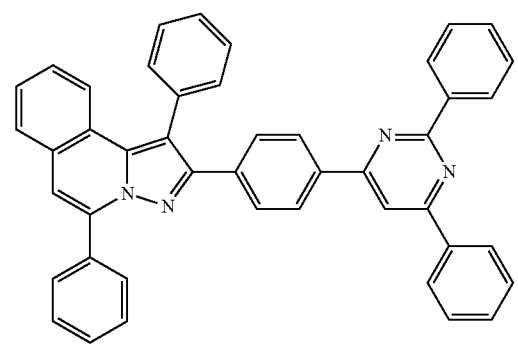
11
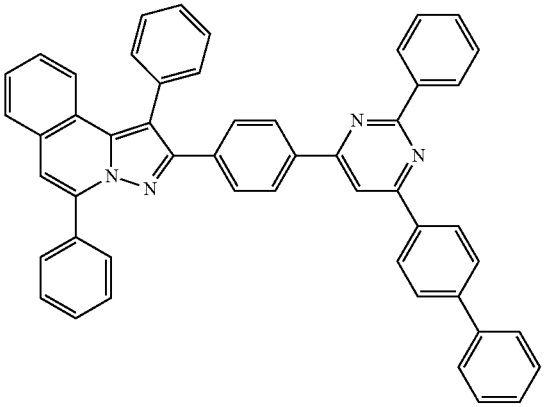
12
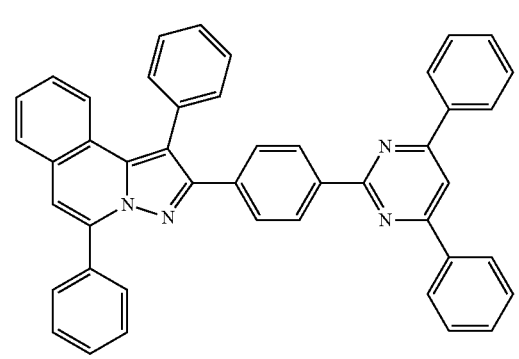

13
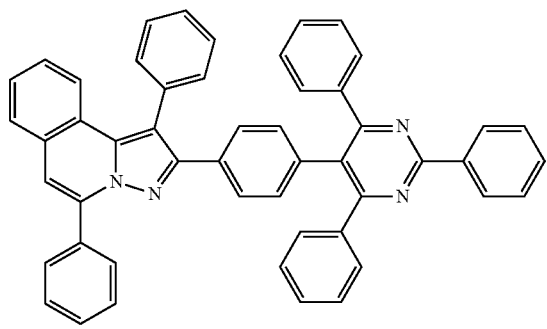
14
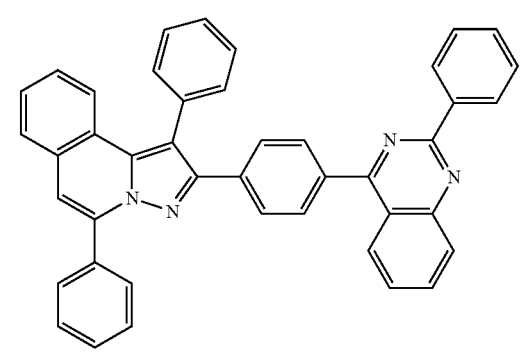
19
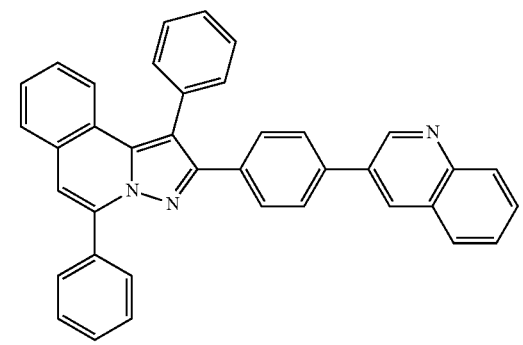
20
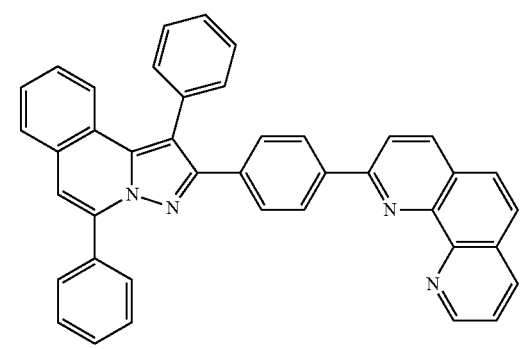
23
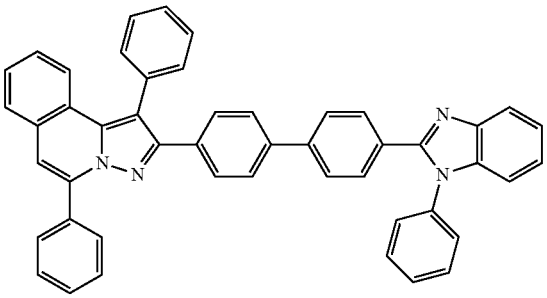
24
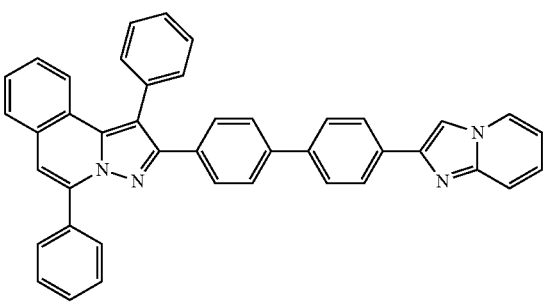
25
26
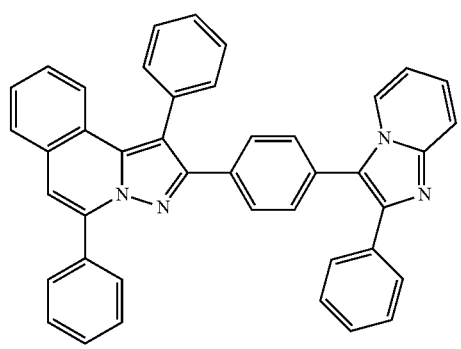

27
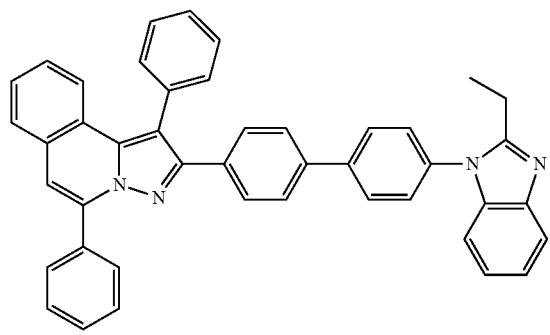
28
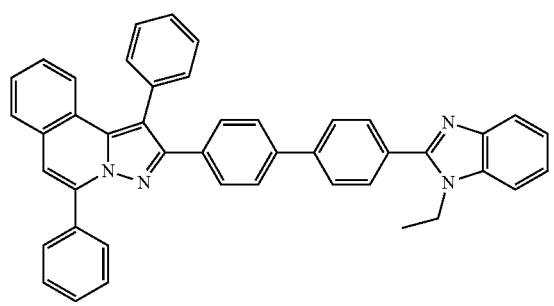
33
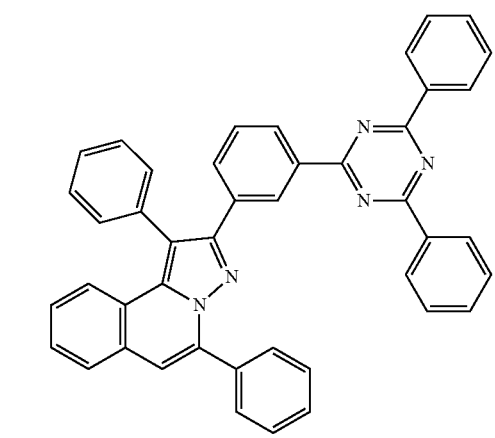
34
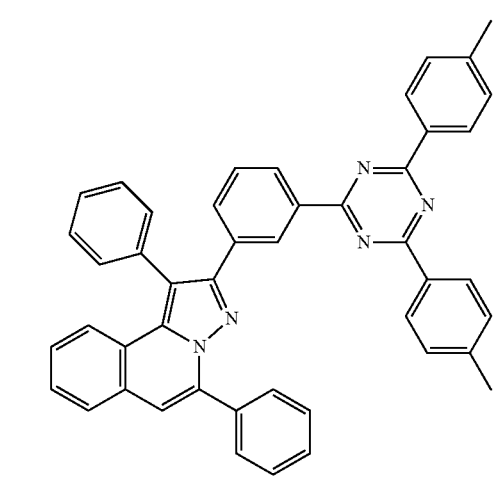
35
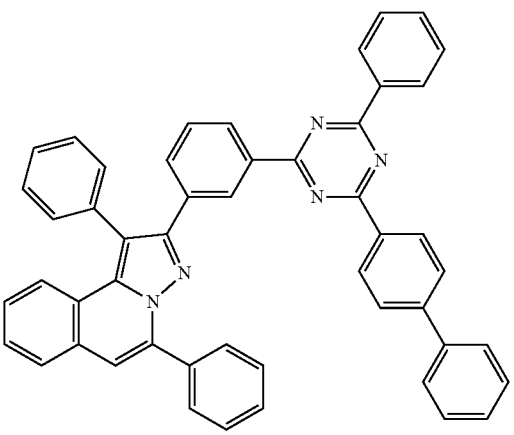
36
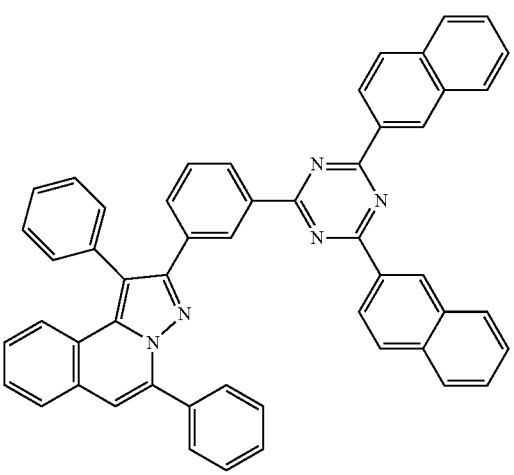
37
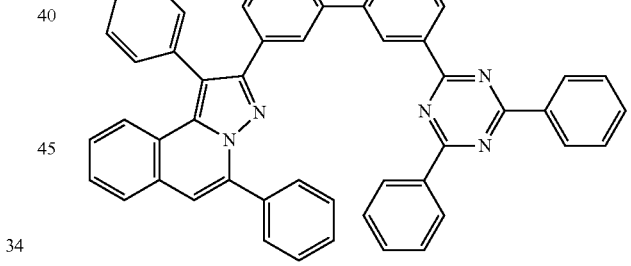
38
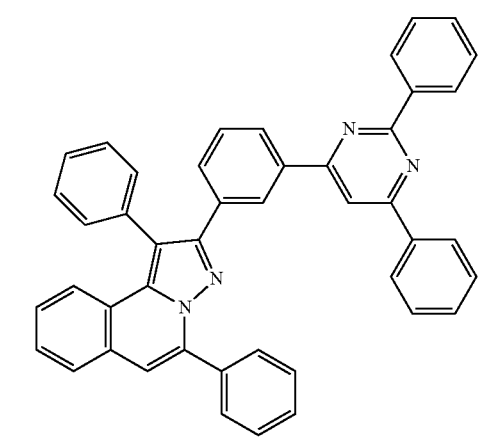

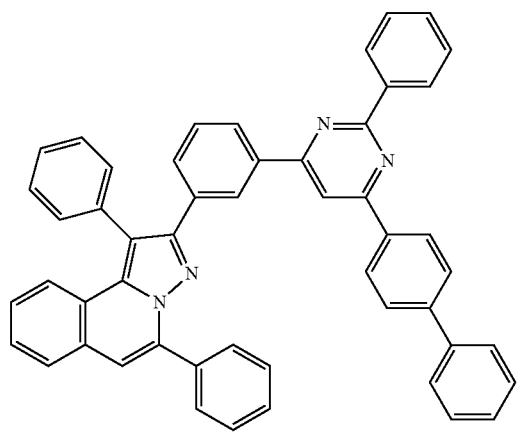
39
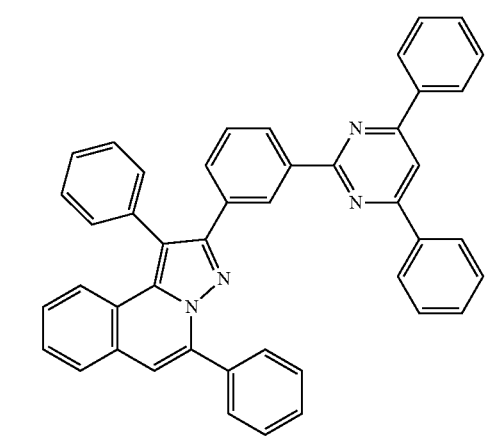
40
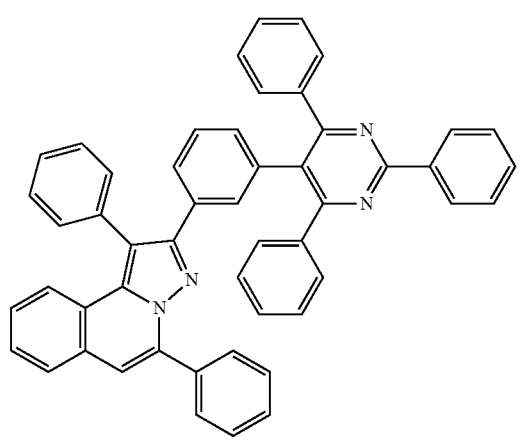
41
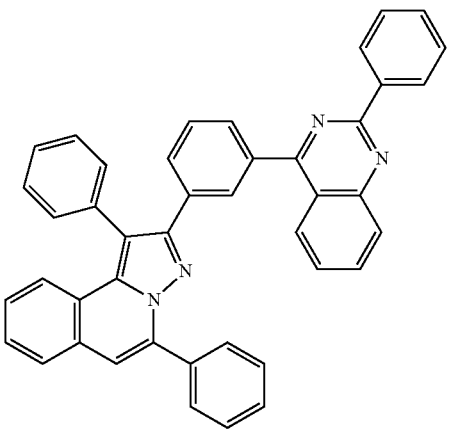
42
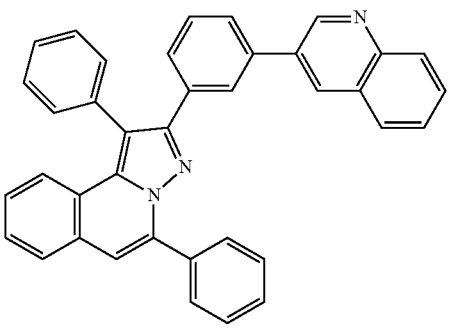
47
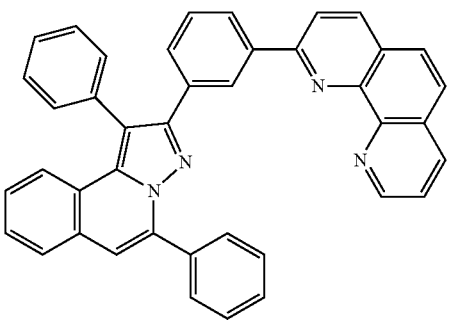
48
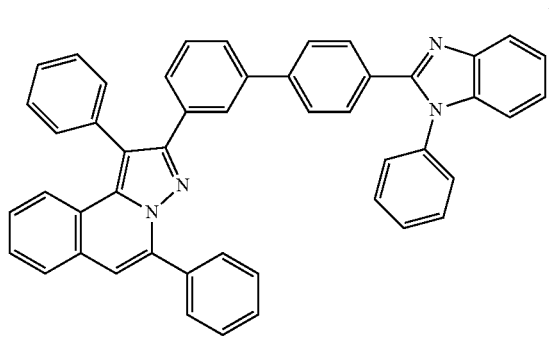
51

-continued
52
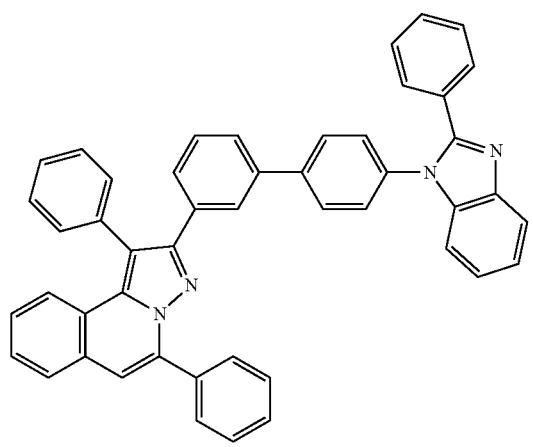
56
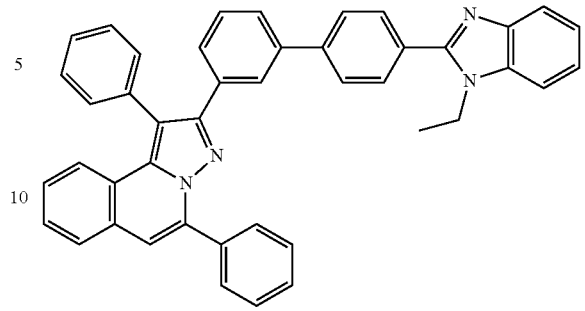
53
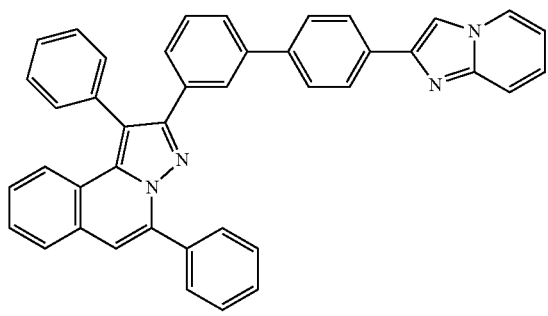
61
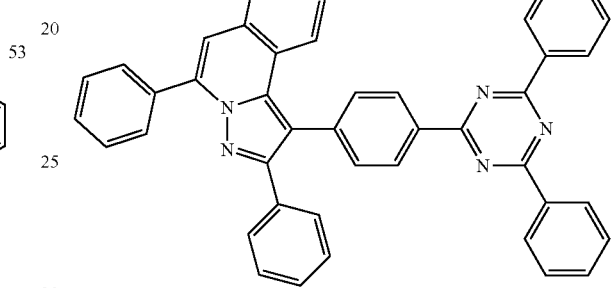
54
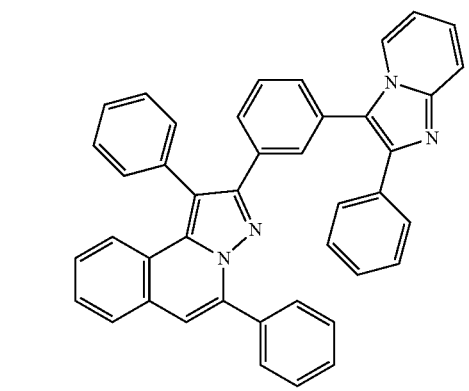
62
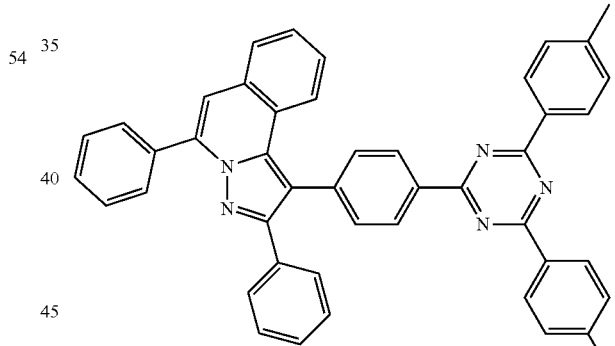
55
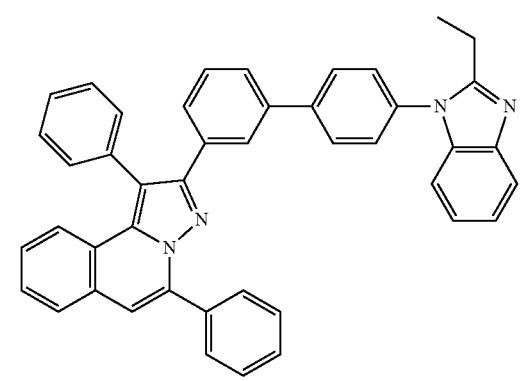
63
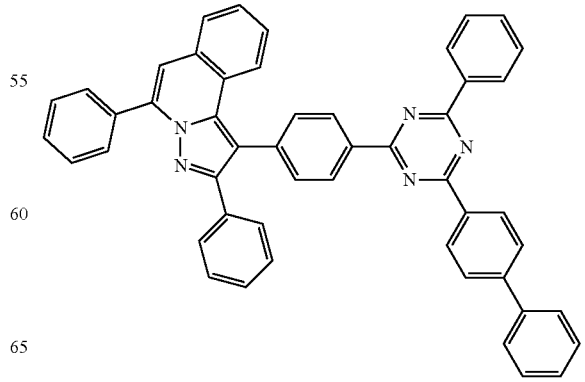

64
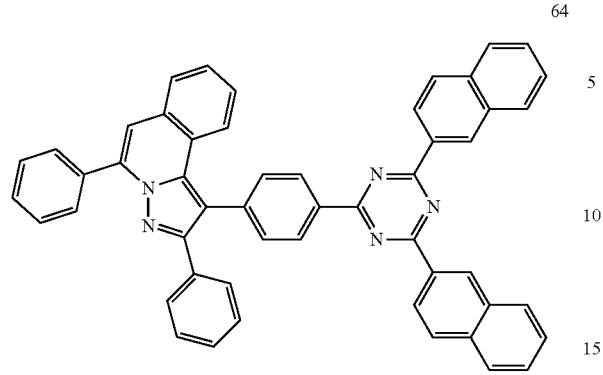
65
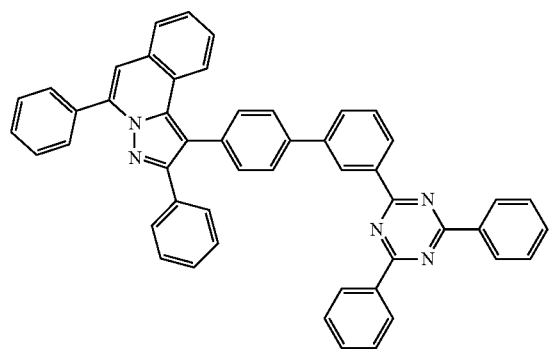
66
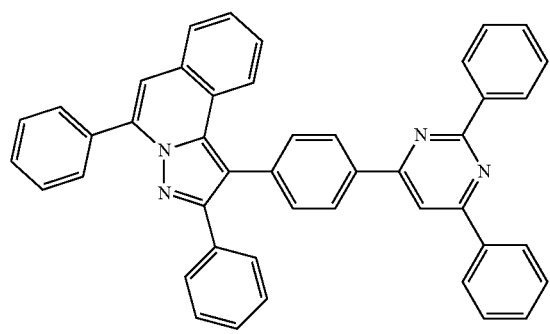
67
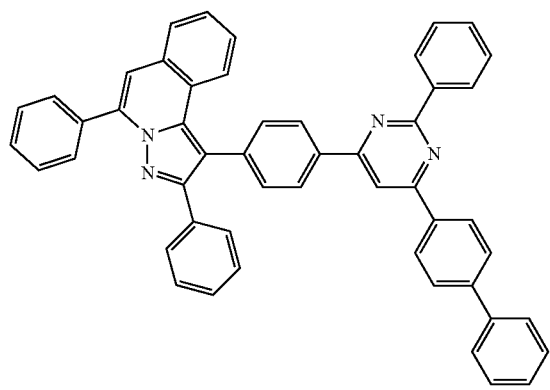
68
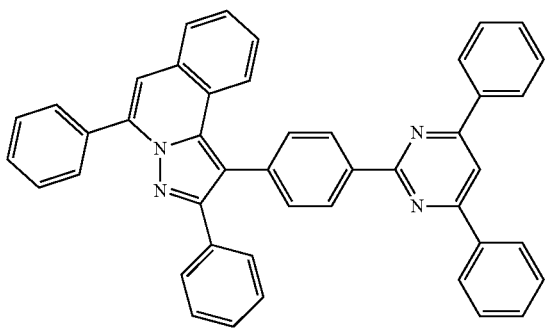
69
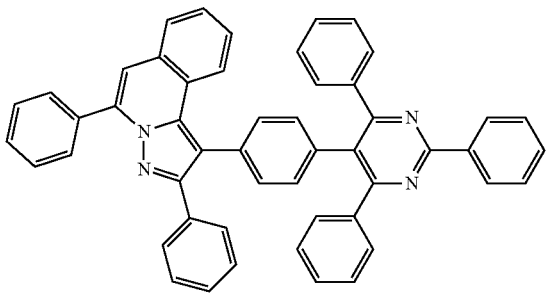
70
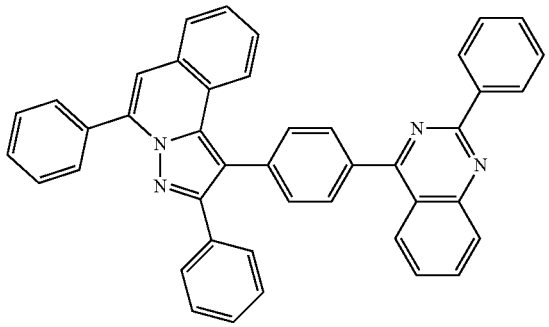
75
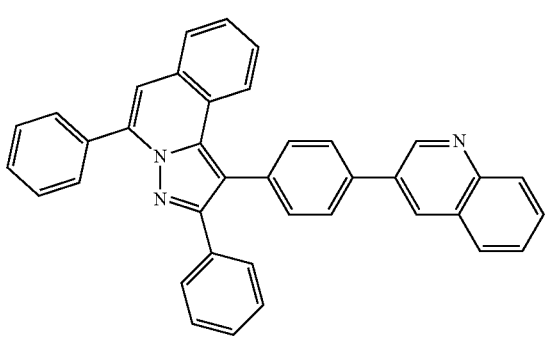

76
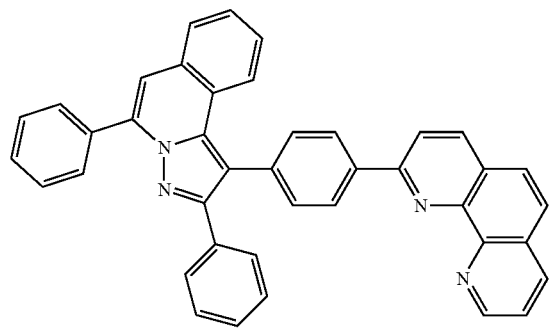
79
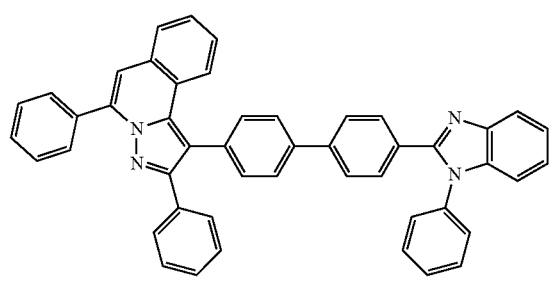
80
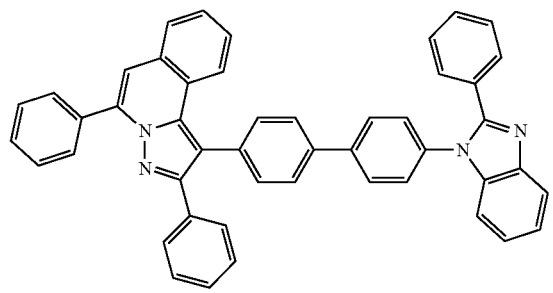
81
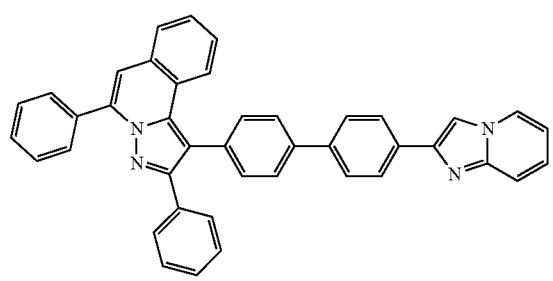
82
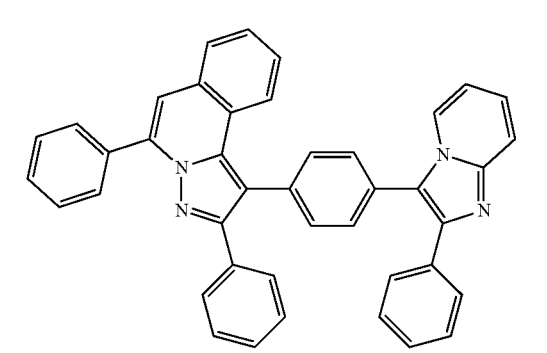
83
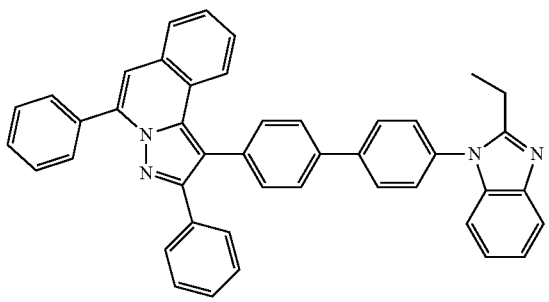
84
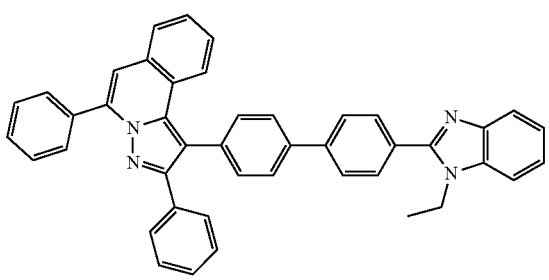
89
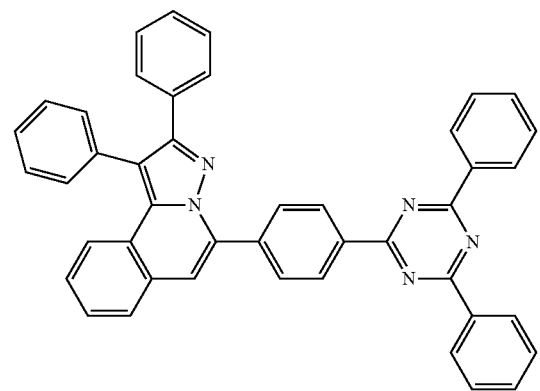
90
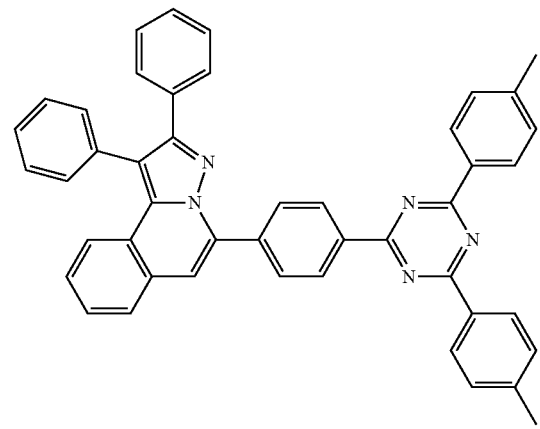

91
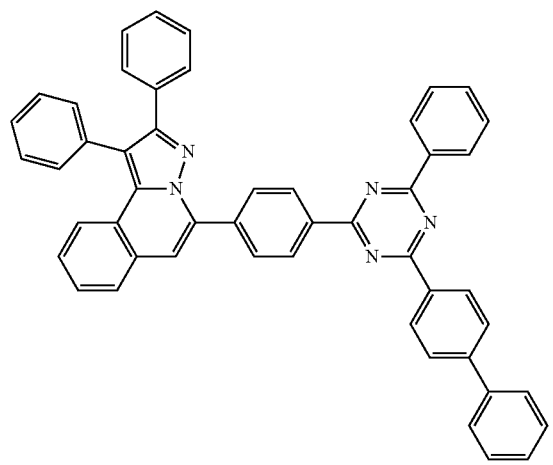
92
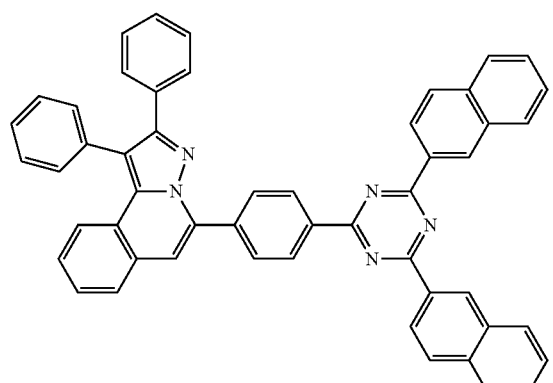
93
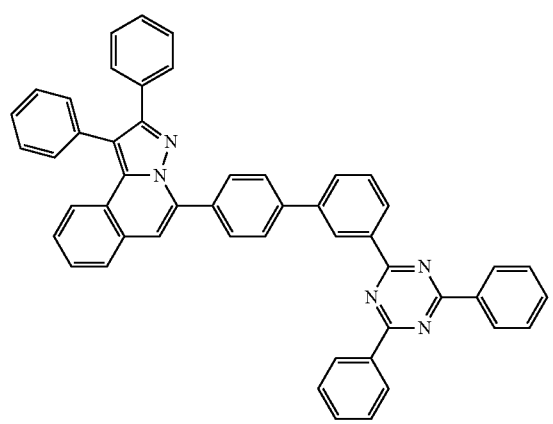
94
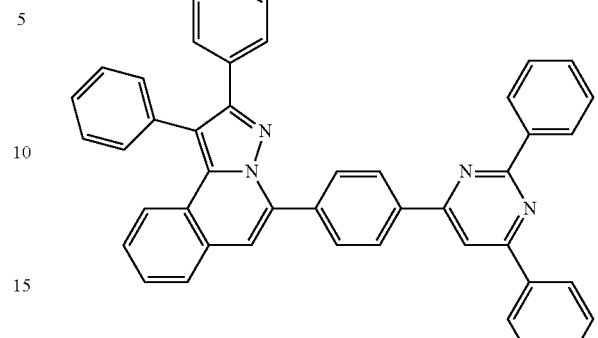
95
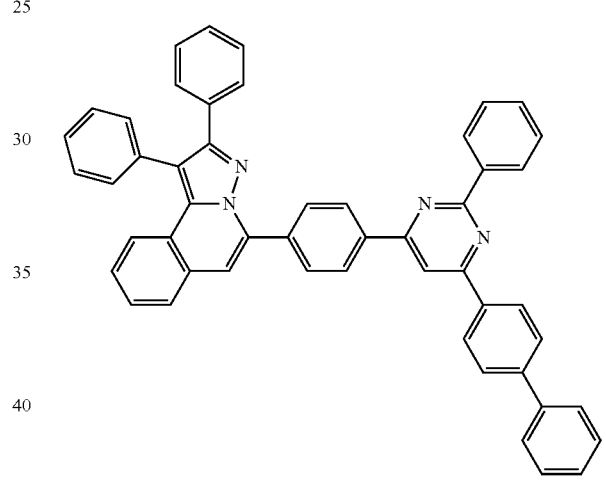
96
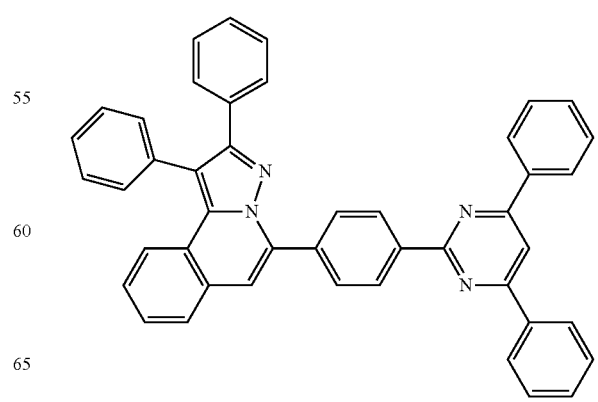

97
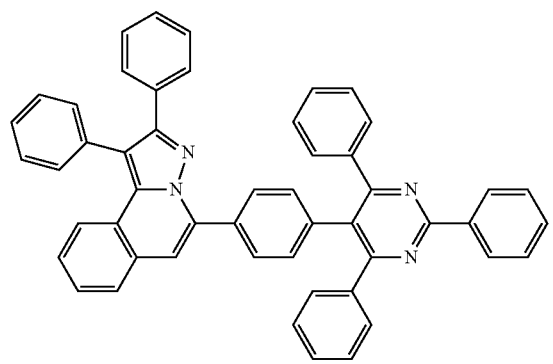
98
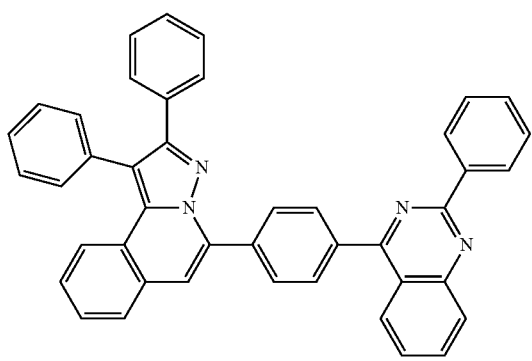
103
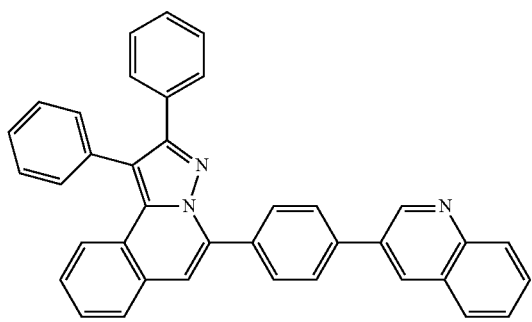
104
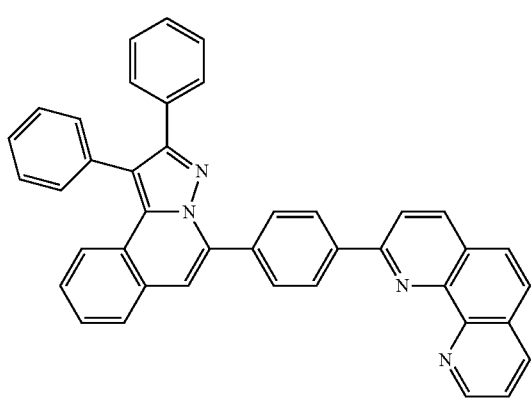
107
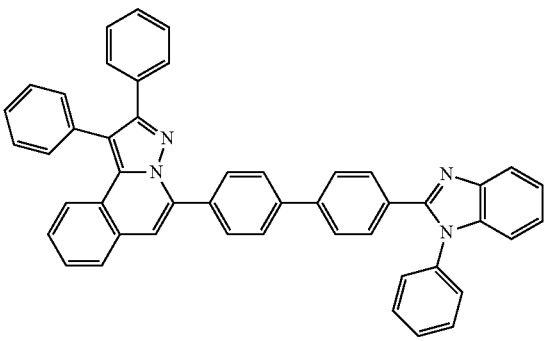
108
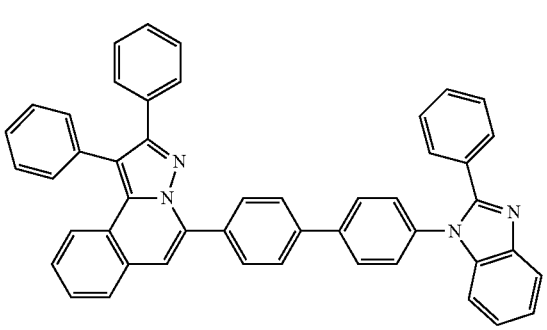
109
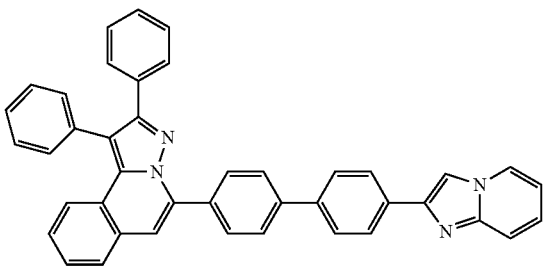
110
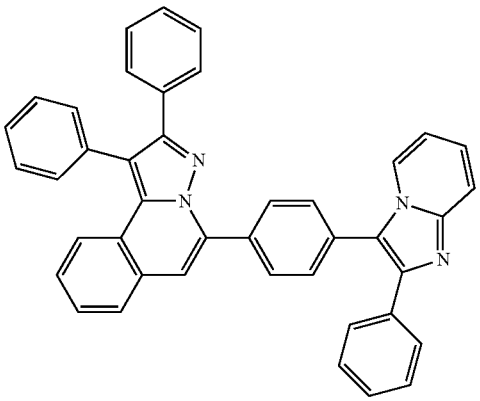

111
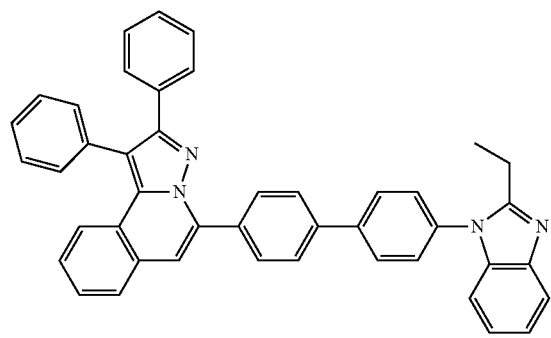
112
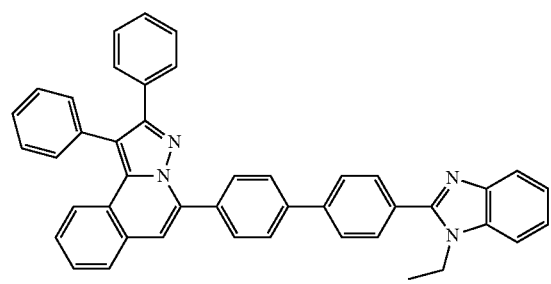
117
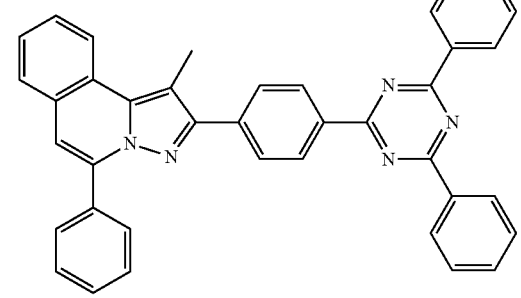
118
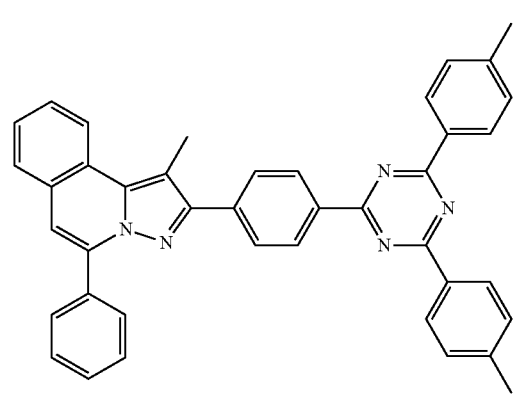
119
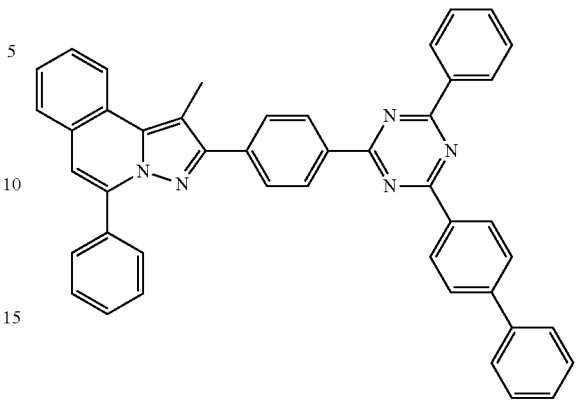
120
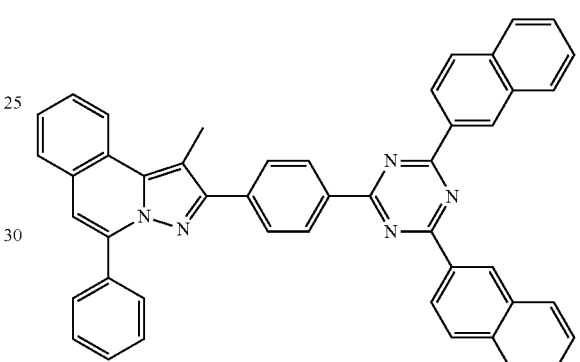
121
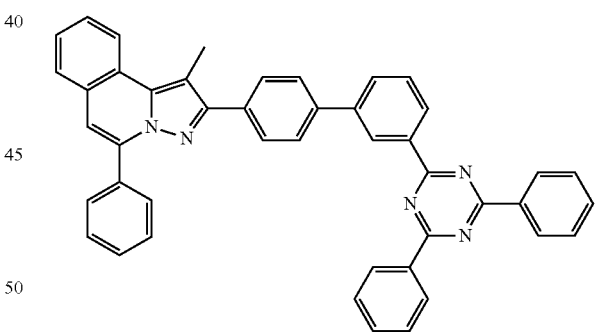
122
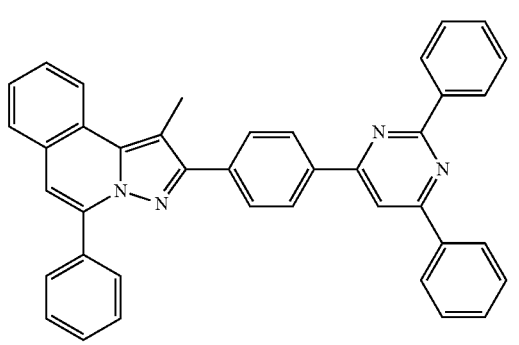

-continued
123
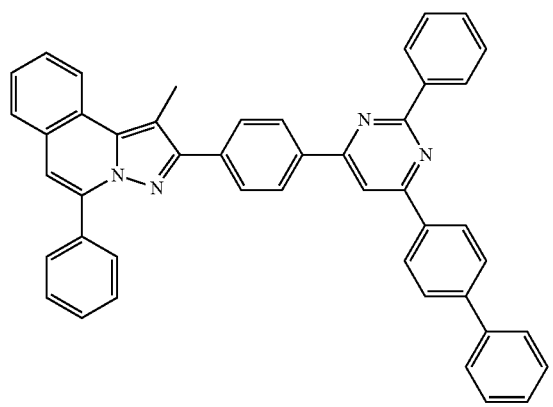
124
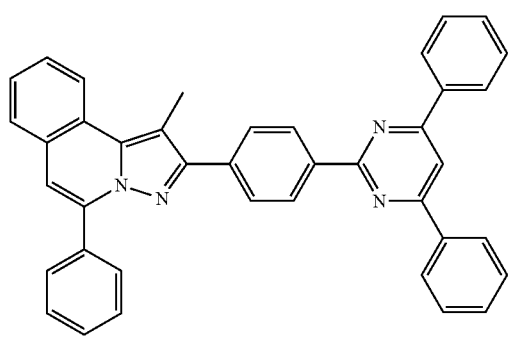
125
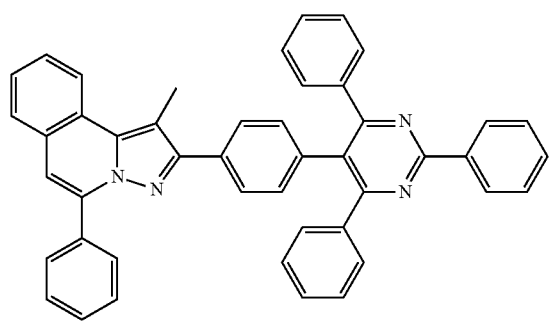
126
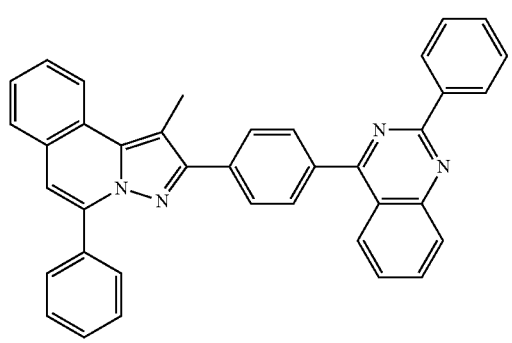
-continued
131
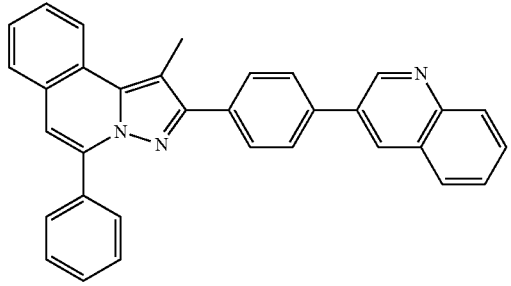
132
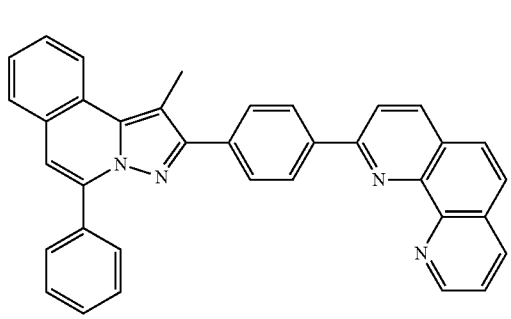
135
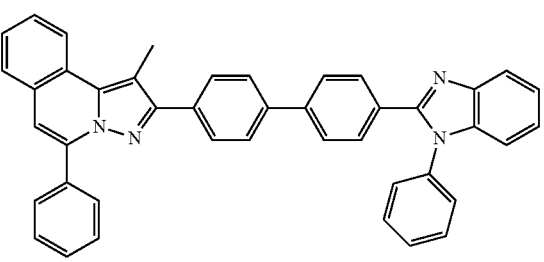
136
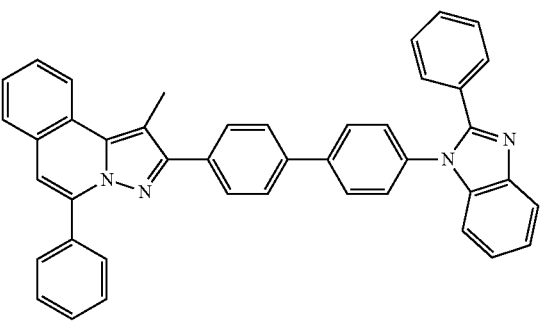
137
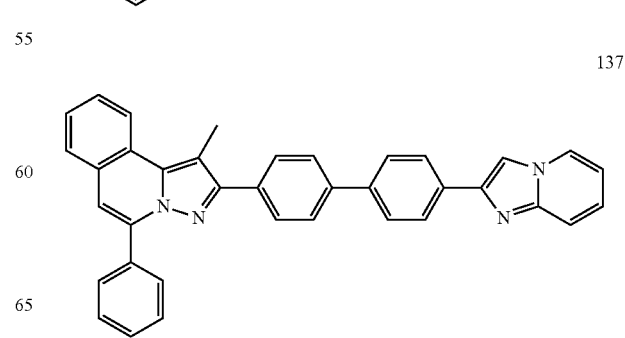

138
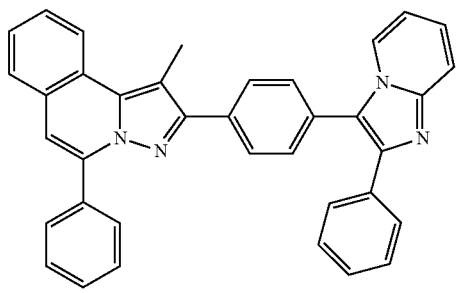
139
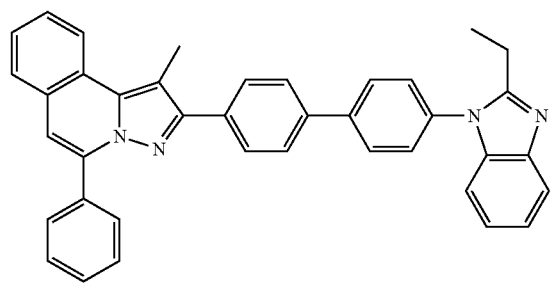
140
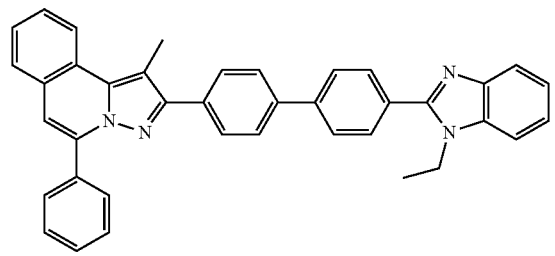
145
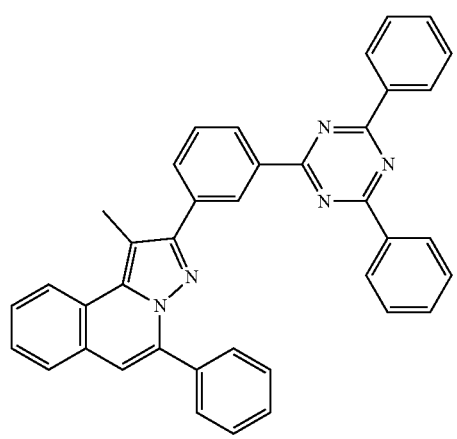
146
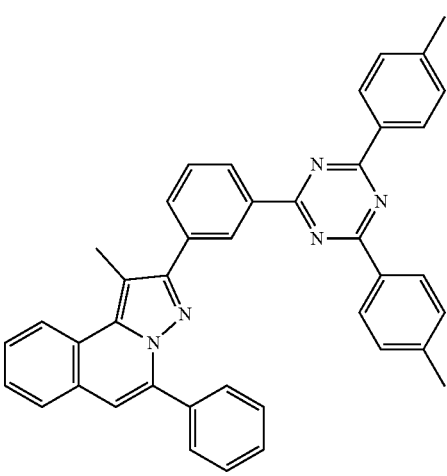
147
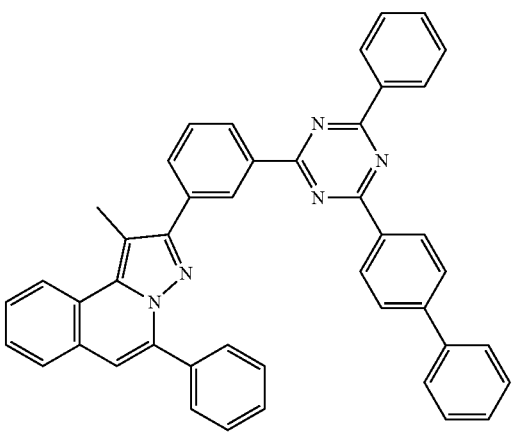
148
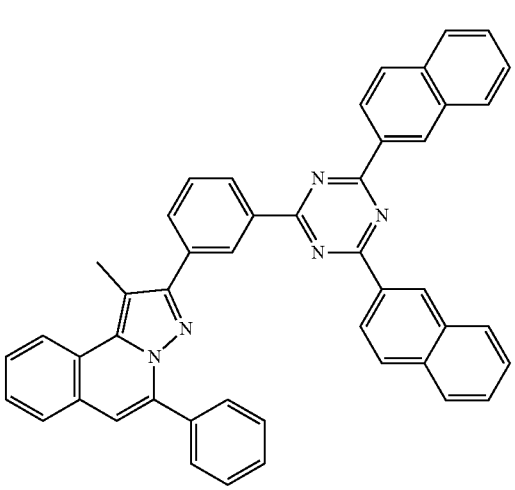

149
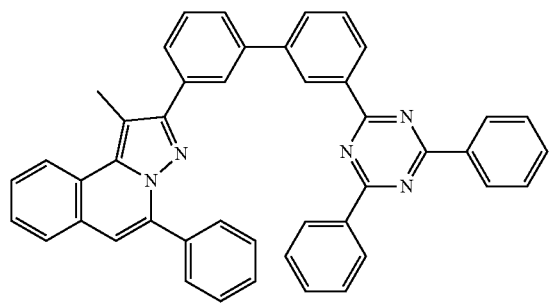
150
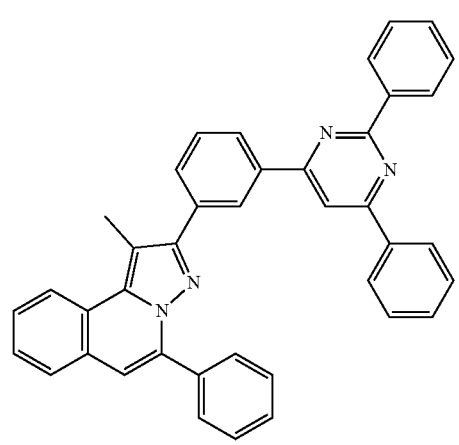
151
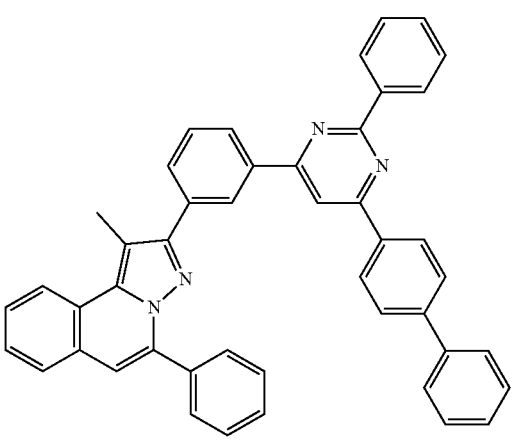
152
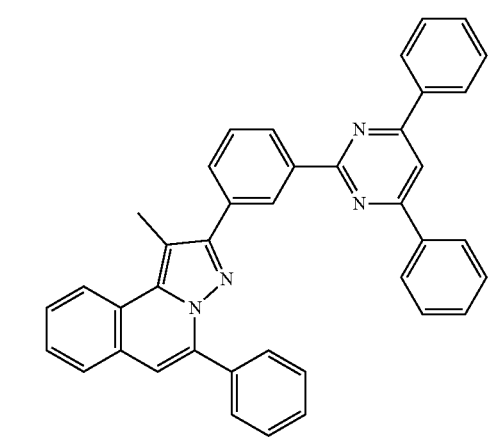
153
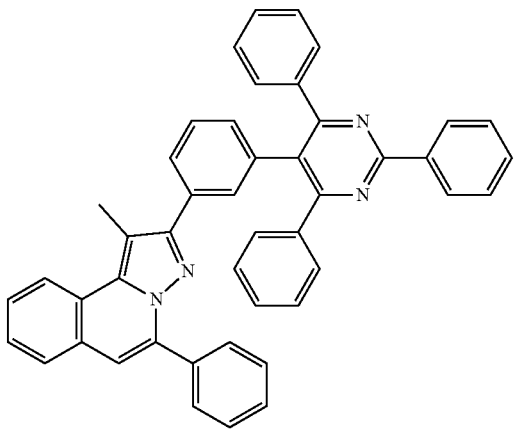
154
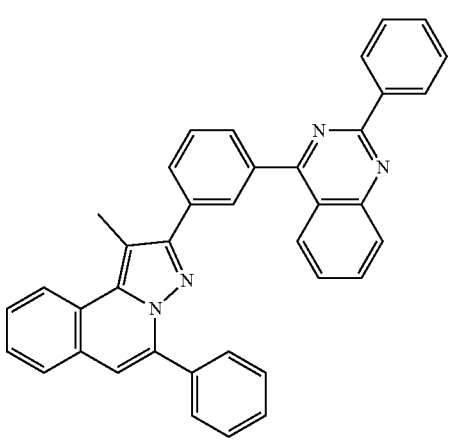
159
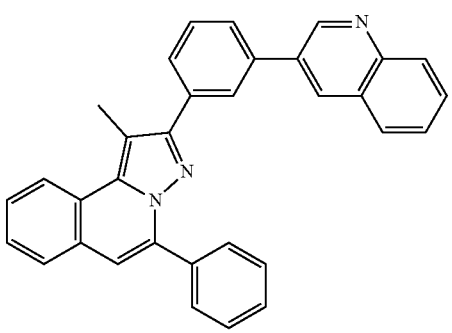
160
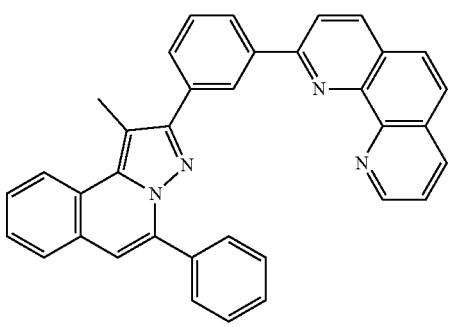

163
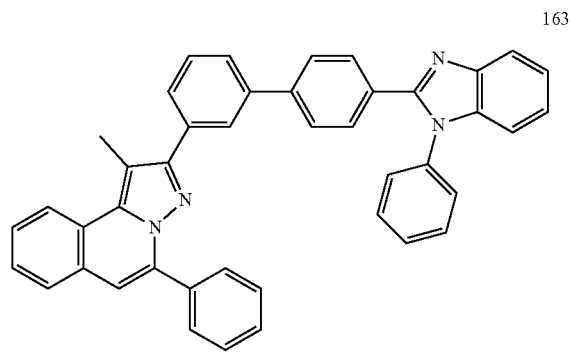
164
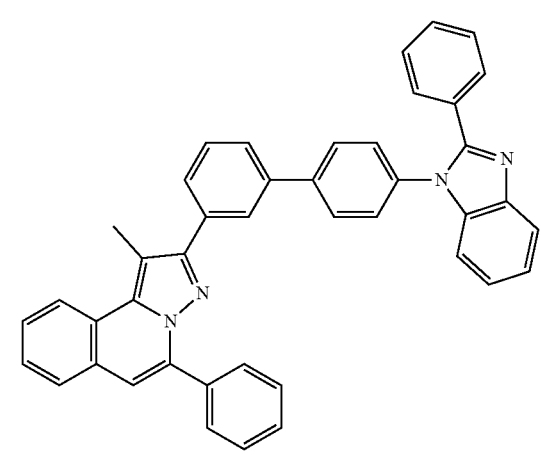
165
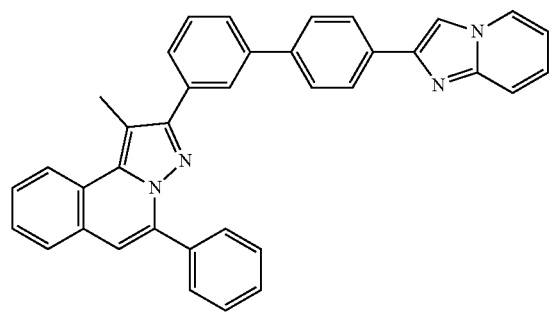
166
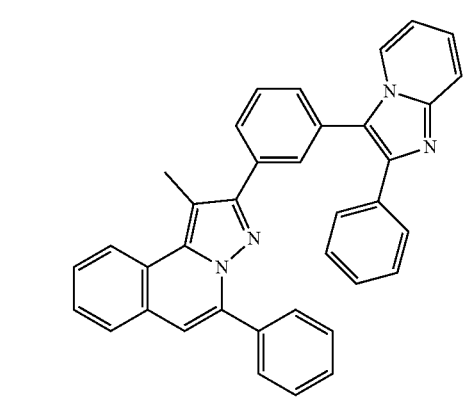
167
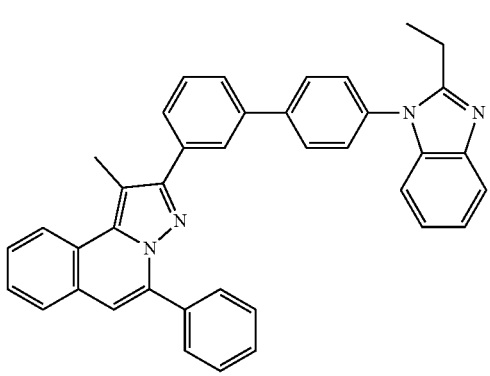
168
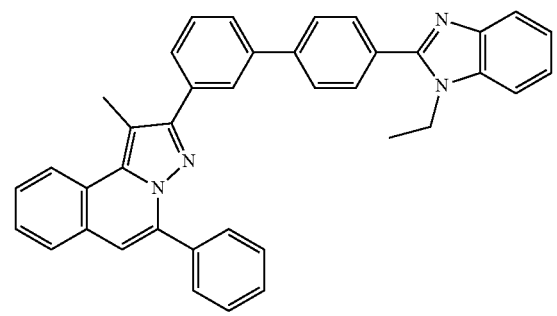
169
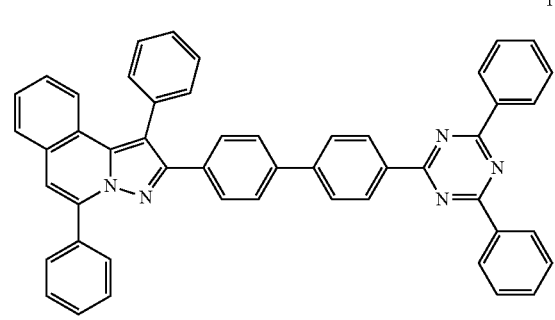
170
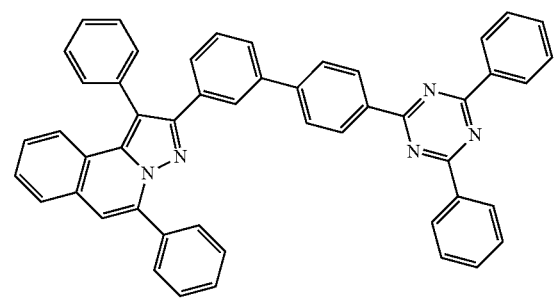
171
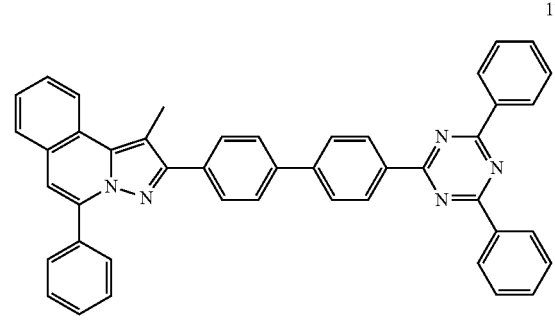

172
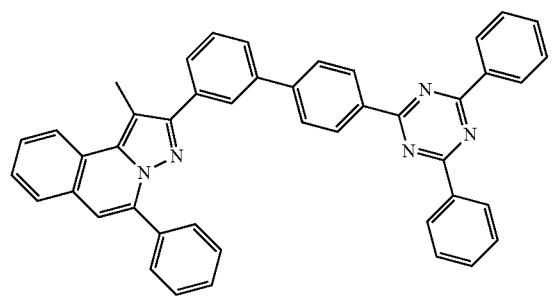
173
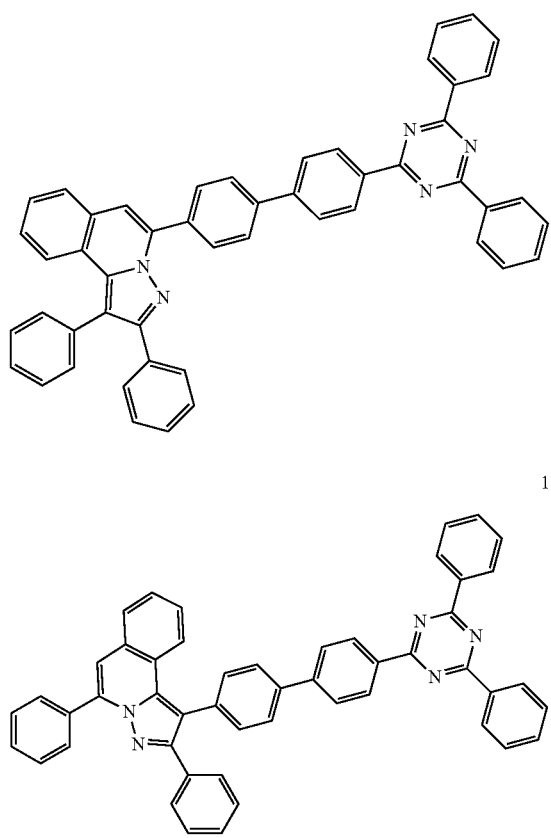
174
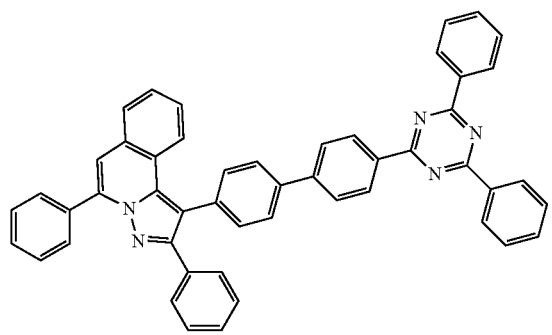
175
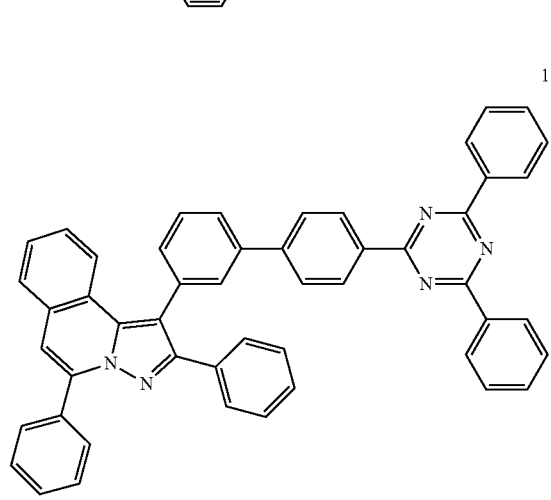
176
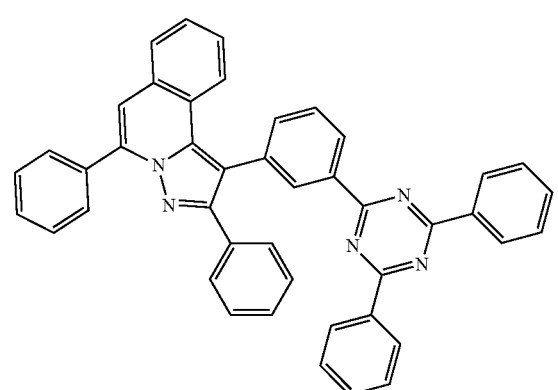
177
178
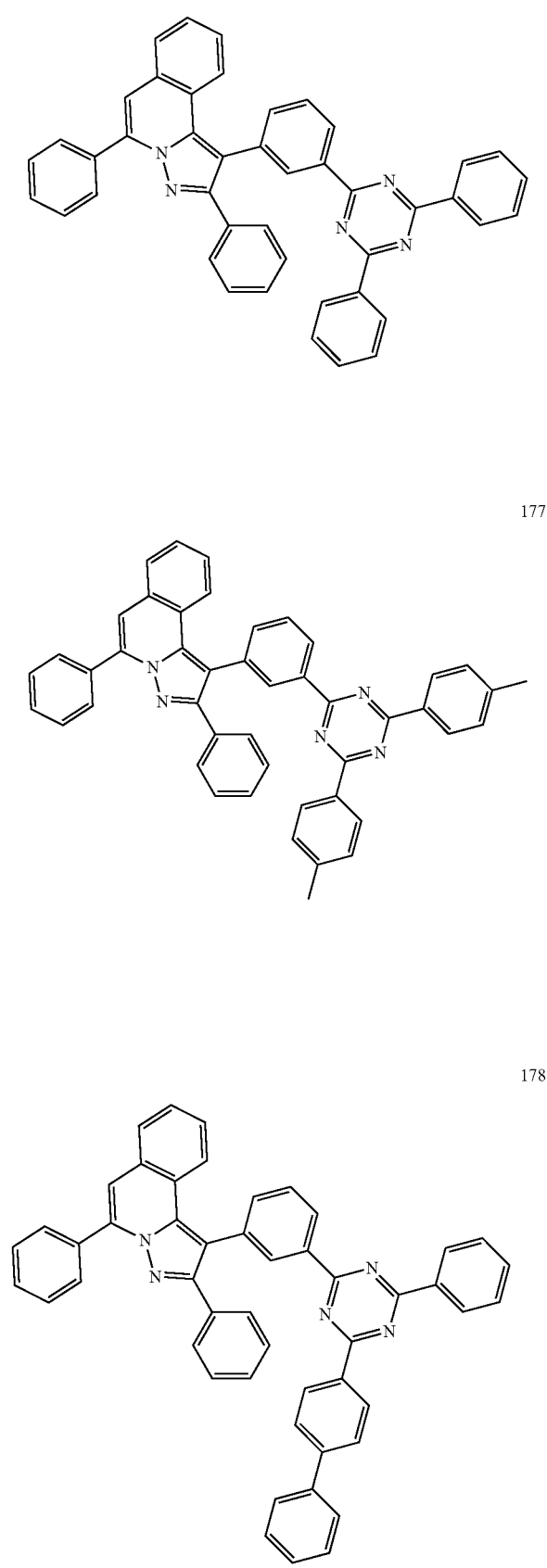

179
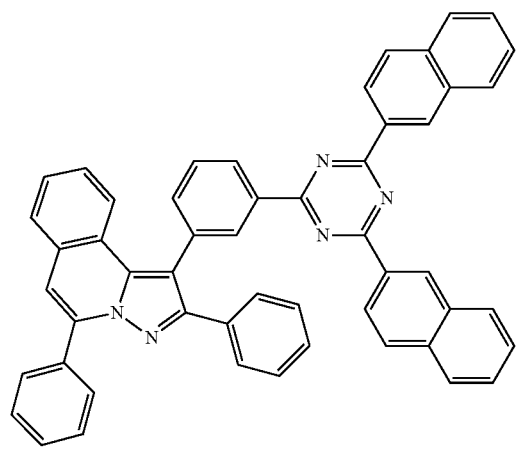
180
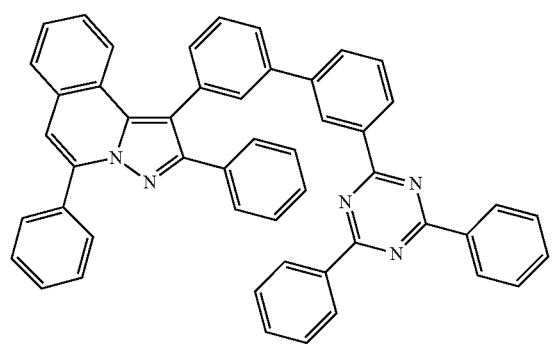
181
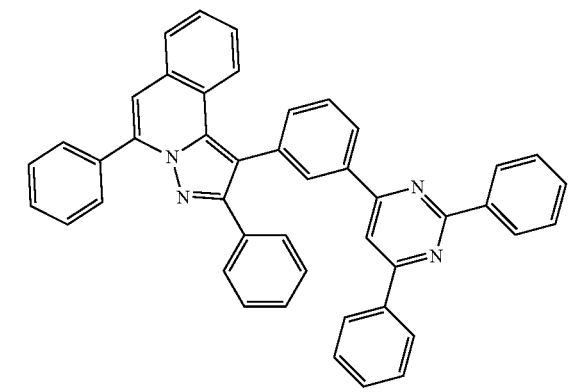
182
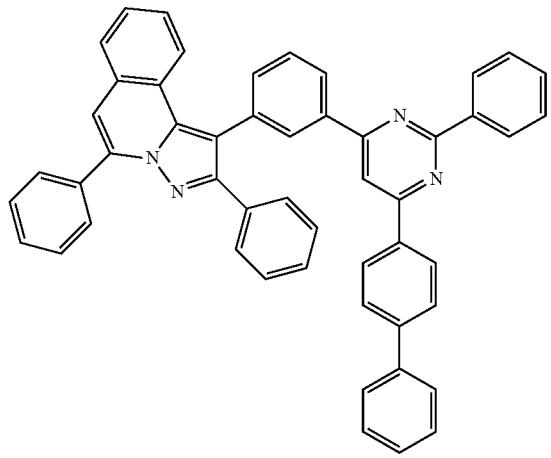
183
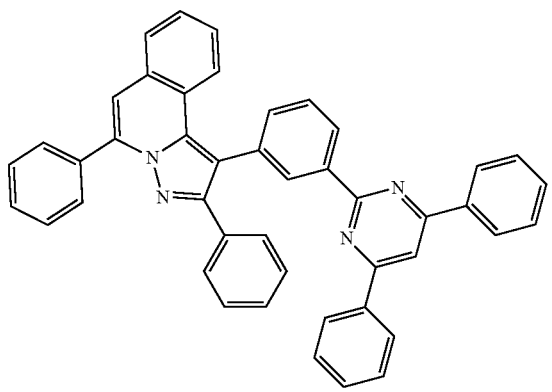
184
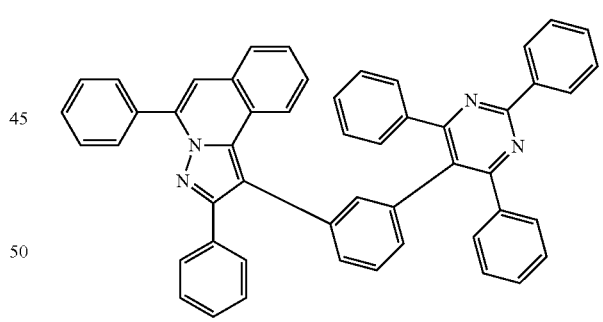
185
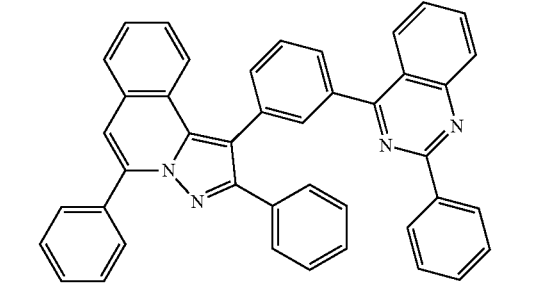

186

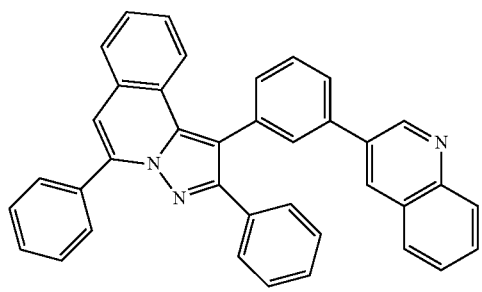

187

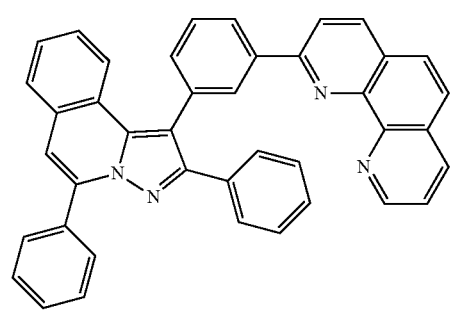

188

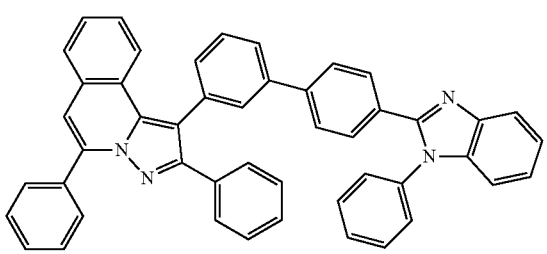

189

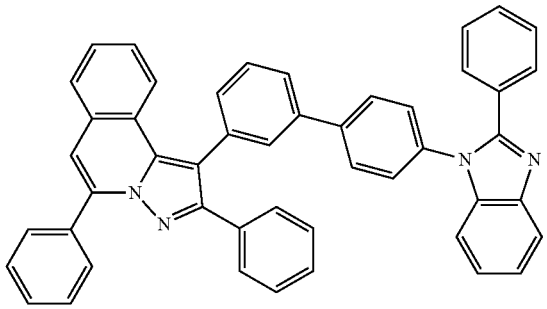

190

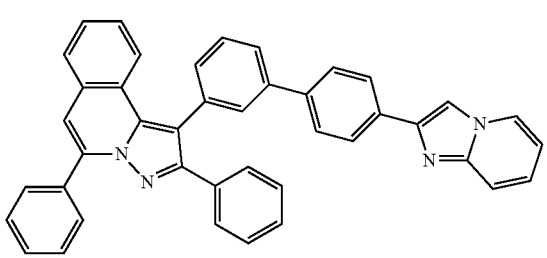

191

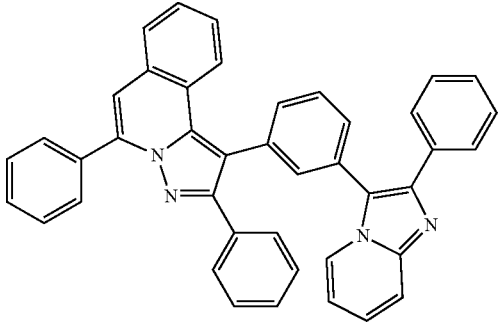

192

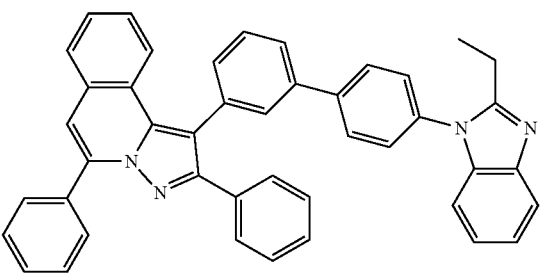

193

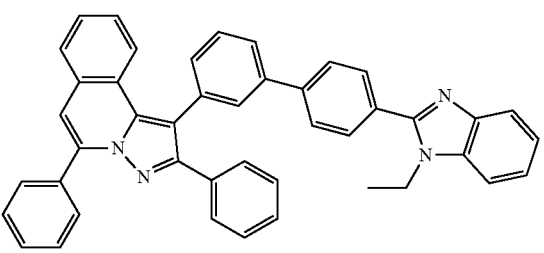

In addition, various substituents may be introduced into the structure of Chemical Formula 1 to synthesize a compound having inherent characteristics of the introduced substituent. For example, a substituent usually used for a hole injection layer material, a material for transporting holes, a light emitting layer material, and an electron transporting layer material, which are used for manufacturing an organic light emitting device, may be introduced into the core structure to synthesize a material which satisfies conditions required for each organic material layer.

Furthermore, various substituents may be introduced into the structure of Chemical Formula 1 to finely adjust an energy bandgap, and meanwhile, characteristics at the interface between organic materials may be improved, and the use of the material may be diversified.

Meanwhile, the hetero-cyclic compound has a high glass transition temperature (Tg) and thus has excellent thermal stability. The increase in thermal stability becomes an important factor which provides driving stability to a device.

The hetero-cyclic compound according to an exemplary embodiment of the present application may be prepared by a multi-step chemical reaction. Some intermediate compounds are first prepared, and the compound of Chemical Formula 1 may be prepared from the intermediate compounds. More specifically, the hetero-cyclic compound according to an exemplary embodiment of the present application may be prepared based on the Preparation Examples to be described below.

Another exemplary embodiment of the present application provides an organic light emitting device comprising the hetero-cyclic compound represented by Chemical Formula 1.

The organic light emitting device according to an exemplary embodiment of the present application may be manufactured by typical manufacturing methods and materials of the organic light emitting device, except that the above-described hetero-cyclic compound is used to form an organic material layer having one or more layer.

The hetero-cyclic compound may be formed as an organic material layer by not only a vacuum deposition method, but also a solution application method when an organic light emitting device is manufactured. Here, the solution application method means spin coating, dip coating, inkjet printing, screen printing, a spray method, roll coating, and the like, but is not limited thereto.

Specifically, the organic light emitting device according to an exemplary embodiment of the present application comprises a positive electrode, a negative electrode, and an organic material layer having one or more layer disposed between the positive electrode and the negative electrode, in which one or more layers of the organic material layer comprise the hetero-cyclic compound represented by Chemical Formula 1.

FIGS. 1 to 3 exemplify the stacking sequence of the electrodes and the organic material layer of the organic light emitting device according to an exemplary embodiment of the present application. However, the scope of the present application is not intended to be limited by these drawings, and the structure of the organic light emitting device known in the art may also be applied to the present application.

According to FIG. 1, an organic light emitting device in which a positive electrode 200, an organic material layer 300, and a negative electrode 400 are sequentially stacked on a substrate 100 is illustrated. However, the organic light emitting device is not limited only to such a structure, and as in FIG. 2, an organic light emitting device in which a negative electrode, an organic material layer, and a positive electrode are sequentially stacked on a substrate may also be implemented.

FIG. 3 exemplifies a case where an organic material layer is a multilayer. An organic light emitting device according to FIG. 3 comprises a hole injection layer 301, a hole transporting layer 302, a light emitting layer 303, a hole blocking layer 304, an electron transporting layer 305, and an electron injection layer 306. However, the scope of the present application is not limited by the stacking structure as described above, and if necessary, the other layers except for the light emitting layer may be omitted, and another necessary functional layer may be further added.

The organic light emitting device according to the present application may be manufactured by the materials and methods known in the art, except that one or more layers of the organic material layer comprise the hetero-cyclic compound represented by Chemical Formula 1.

The hetero-cyclic compound represented by Chemical Formula 1 may alone constitute one or more layers of the organic material layer of the organic light emitting device. However, the hetero-cyclic compound represented by Chemical Formula 1 may be mixed with another material, if necessary, to constitute an organic material layer.

The hetero-cyclic compound represented by Chemical Formula 1 may be used as a material for an electron transporting layer, a hole blocking layer, or a light emitting layer, and the like in an organic light emitting device. As an example, the hetero-cyclic compound represented by Chemical Formula 1 may be used as a material for an electron transporting layer, a hole transporting layer, or a light emitting layer of an organic light emitting device.

Furthermore, the hetero-cyclic compound represented by Chemical Formula 1 may be used as a material for a light emitting layer in an organic light emitting device. As an example, the hetero-cyclic compound represented by Chemical Formula 1 may be used as a material for a phosphorescent host of a light emitting layer in an organic light emitting device.

In the organic light emitting device according to an exemplary embodiment of the present application, the hetero-cyclic compound of Chemical Formula 1 may be more preferably used as a material for an electron transporting layer in the organic light emitting device. In particular, a functional group of a hetero-cyclic group comprising a nitrogen atom, such as Chemical Formulae 2 to 7 may be bonded to at least one of R1 to R8 of Chemical Formula 1, more preferably at least one of R1, R2, and R8, thereby obtaining effects of improved electron affinity and electron mobility. By the effects of improved electron affinity and electron mobility, the driving voltage of the organic light emitting device may be lowered, and the service life characteristics of the organic light emitting device may be improved.

In the organic light emitting device according to an exemplary embodiment of the present application, materials other than the hetero-cyclic compound of Chemical Formula 1 will be exemplified below, but these materials illustrative only and are not for limiting the scope of the present application, and may be replaced with materials publicly known in the art.

As a positive electrode material, materials having a relatively high work function may be used, and a transparent conductive oxide, a metal or a conductive polymer, and the like may be used. Specific examples of the positive electrode material comprise: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as $ZnO:Al$ or $SnO_2:Sb$; a conductive polymer such as poly(3-methylthiophene), poly[3,4-(ethylene-1,2-dioxy)thiophene] (PEDOT), polypyrrole, and polyaniline; and the like, but are not limited thereto.

As a negative electrode material, materials having a relatively low work function may be used, and a metal, a metal oxide, or a conductive polymer, and the like may be used. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2/Al$; and the like, but are not limited thereto.

As a hole injection material, a publicly-known hole injection material may also be used, and it is possible to use, for example, a phthalocyanine compound such as copper phthalocyanine disclosed in U.S. Pat. No. 4,356,429 or starburst-type amine derivatives described in the document [Advanced Material, 6, p. 677 (1994)], for example, tris(4-carbazoyl-9-ylphenyl)amine (TCTA), 4,4',4"-tris[phenyl(m-tolyl)amino]triphenylamine (m-MTDATA), 1,3,5-tris[4-(3-methylphenylphenylamino)phenyl]benzene (m-MTDAPB), polyaniline/dodecylbenzenesulfonic acid or poly(3,4-ethylenedioxythiophene)/poly(4-styrenesulfonate), which is a soluble conductive polymer, polyaniline/camphor sulfonic acid or polyaniline/poly(4-styrene-sulfonate), and the like.

As a hole transport material, a pyrazoline derivative, an arylamine-based derivative, a stilbene derivative, a triphenyldiamine derivative, and the like may be used, and a low-molecular weight or polymer material may also be used.

As an electron transport material, it is possible to use an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, and the like, and a low-molecular weight material and a polymer material may also be used.

As an electron injection material, for example, LiF is representatively used in the art, but the present application is not limited thereto.

As a light emitting material, a red, green, or blue light emitting material may be used, and if necessary, two or more light emitting materials may be mixed and used. Further, as the light emitting material, a fluorescent material may also be used, but a phosphorescent material may also be used. As the light emitting material, it is also possible to use alone a material which emits light by combining holes and electrons each injected from the positive electrode and the negative electrode, but materials in which a host material and a dopant material are involved in light emission together may also be used.

The organic light emitting device according to an exemplary embodiment of the present application may be a top emission type, a bottom emission type, or a dual emission type according to the material to be used.

The hetero-cyclic compound according to an exemplary embodiment of the present application may act even in organic electronic devices comprising organic solar cells, organic photoconductors, organic transistors, and the like, based on the principle similar to those applied to organic light emitting devices.

MODE FOR INVENTION

Hereinafter, the present specification will be described in more detail through Examples, but these Examples are provided only for exemplifying the present application, and are not intended to limit the scope of the present application.

EXAMPLES

<Synthesis Example 1> Synthesis of Intermediate A

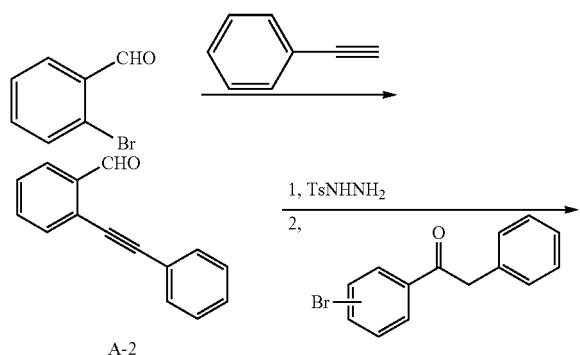

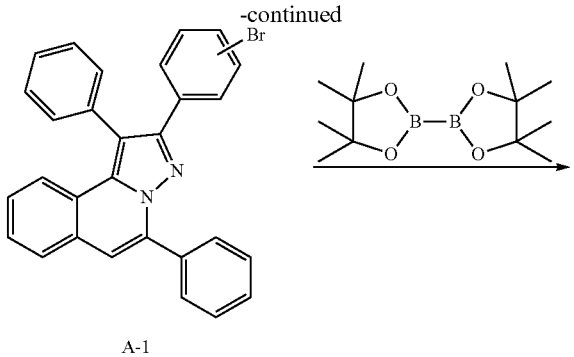

A-1

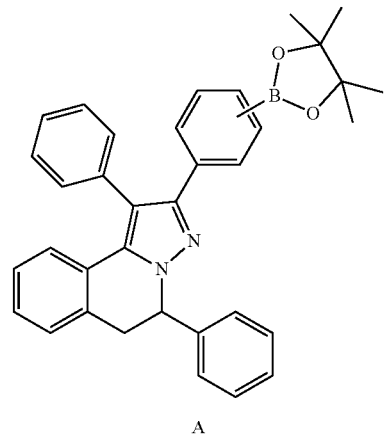

A

Preparation of Compound A-2

10 g (54 mol) of a compound 2-bromoaldehyde, 0.8 g (1.1 mmol) of Pd(PPh$_3$)$_2$Cl$_2$, 0.4 g (2.2 mmol) of Cu', and 300 mL of triethylamine were put into a reactor, and the resulting mixture was stirred at normal temperature of 10 minutes. 6.1 g (59.4 mmol) of phenylacetylene was added thereto, and then the resulting mixture was stirred at 50° C. for 3 hours. After the reaction was completed, the resulting product was cooled to normal temperature, and then extraction was performed with distilled water and EA. After the organic layer was dried over anhydrous MgSO$_4$, the solvent was removed by a rotary evaporator, and then the residue was purified by column chromatography using dichloromethane and hexane as an eluting solvent, thereby obtaining 9.1 g (82%) of Target Compound A-2.

Preparation of Compound A-1

After 9 g (44 mmol) of Compound A-2 was dissolved in ethanol, 8.2 g (44 mmol) of TsNHNH$_2$ was added thereto, and then the resulting solution was stirred at normal temperature for 20 minutes. 1.1 g (4.4 mmol) of AgOTf was added thereto, and then the resulting mixture was stirred at 70° C. for 30 minutes. After the temperature was lowered to normal temperature, 24.2 g (88 mmol) of 4'-bromo-2-phenylacetophenone or 3'-bromo-2-phenylacetophenone and 37.4 g (176 mmol) of K$_3$PO$_4$ were added thereto, and then the resulting mixture was stirred at 70° C. for 17 hours or more. After the reaction was completed, the resulting product was cooled to normal temperature, and then extraction was performed with distilled water and EA. After the organic layer was dried over anhydrous MgSO$_4$, the solvent was removed by a rotary evaporator, and then the residue was purified by column chromatography using dichloromethane and hexane as an eluting solvent, thereby obtaining 14.6 g (70%) of Target Compound A-1.

Preparation of Compound A 10 g (21.03 mmol) of Compound A-1, 6.41 g (25.24 mmol) of bis(pinacolato)diboron, 769 mg (1.05 mmol) of $PdCl_2$(dppf), and 6.19 g (63.09 mmol) of KOAc were dissolved in 100 mL of 1,4-dioxane, and then the resulting solution stirred was stirred at 80° C. for 12 hours. After the reaction was completed, distilled water and DCM were added thereto at room temperature, extraction was performed, the organic layer was dried over $MgSO_4$, and then the solvent was removed by a rotary evaporator. The reactant was purified with column chromatography (DCM), thereby obtaining 10.76 g (98%) of Target Compound A.

<Synthesis Example 2> Synthesis of Intermediate B

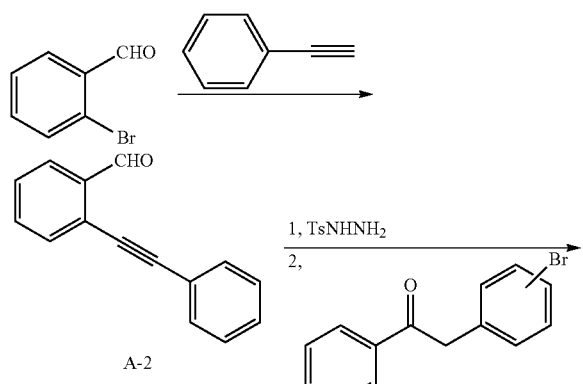

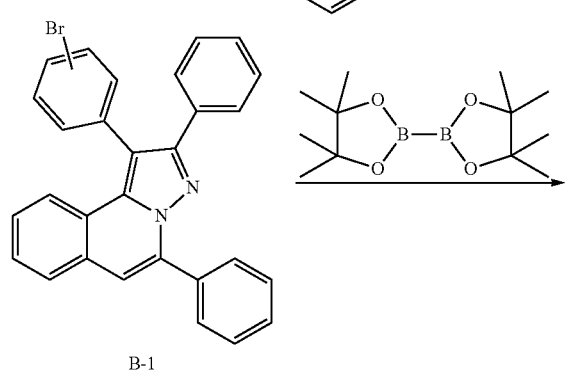

Preparation of Compound B-1

After 9 g (44 mmol) of Compound A-2 was dissolved in ethanol, 8.2 g (44 mmol) of $TsNHNH_2$ was added thereto, and then the resulting solution was stirred at normal temperature for 20 minutes. 1.1 g (4.4 mmol) of AgOTf was added thereto, and then the resulting mixture was stirred at 70° C. for 30 minutes. After the temperature was cooled to normal temperature, 24.2 g (88 mmol) of 2-(4-bromophenyl)acetophenone or 2-(3-bromophenyl)acetophenone and 37.4 g (176 mmol) of $K_3PO_4$ were added thereto, and then the resulting mixture was stirred at 70° C. for 17 hours or more. After the reaction was completed, the resulting product was cooled to normal temperature, and then extraction was performed with distilled water and EA. After the organic layer was dried over anhydrous $MgSO_4$, the solvent was removed by a rotary evaporator, and then the residue was purified by column chromatography using dichloromethane and hexane as an eluting solvent, thereby obtaining 14.0 g (67%) of Target Compound B-1.

Preparation of Compound B 10 g (21.03 mmol) of Compound B-1, 6.41 g (25.24 mmol) of bis(pinacolato)diboron, 769 mg (1.05 mmol) of $PdCl_2$(dppf), and 6.19 g (63.09 mmol) of KOAc were dissolved in 100 mL of 1,4-dioxane, and then the resulting solution was stirred at 80° C. for 12 hours. After the reaction was completed, distilled water and DCM were added thereto at room temperature, extraction was performed, the organic layer was dried over $MgSO_4$, and then the solvent was removed by a rotary evaporator. The reactant was purified with column chromatography (DCM), thereby obtaining 10.76 g (98%) of Target Compound B.

<Synthesis Example 3> Synthesis of Intermediate C

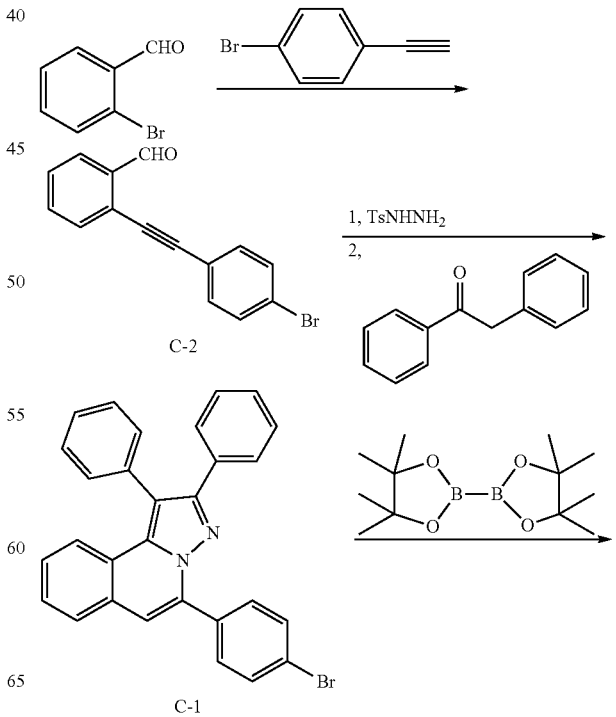

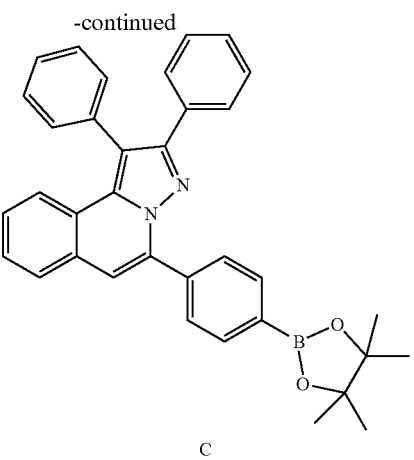

C

Preparation of Compound C-2

10 g (54 mol) of a compound 2-bromoaldehyde, 0.8 g (1.1 mmol) of Pd(PPh₃)₂Cl₂, 0.4 g (2.2 mmol) of CuI, and 300 mL of triethylamine were put into a reactor, and the resulting mixture was stirred at normal temperature of 10 minutes. 10.7 g (59.4 mmol) of 1-bromo-4-ethynylbenzene was added thereto, and then the resulting mixture was stirred at 50° C. for 3 hours. After the reaction was completed, the resulting product was cooled to normal temperature, and then extraction was performed with distilled water and EA. After the organic layer was dried over anhydrous MgSO₄, the solvent was removed by a rotary evaporator, and then the residue was purified by column chromatography using dichloromethane and hexane as an eluting solvent, thereby obtaining 13.0 g (85%) of Target Compound C-2.

Preparation of Compound C-1

After 12.5 g (44 mmol) of Compound C-2 was dissolved in ethanol, 8.2 g (44 mmol) of TsNHNH₂ was added thereto, and then the resulting solution was stirred at normal temperature for 20 minutes. 1.1 g (4.4 mmol) of AgOTf was added thereto, and then the resulting mixture was stirred at 70° C. for 30 minutes. After the temperature was cooled to normal temperature, 17.27 g (88 mmol) of 1,2-diphenylethanone and 37.4 g (176 mmol) of K₃PO₄ were added thereto, and then the resulting mixture was stirred at 70° C. for 17 hours or more. After the reaction was completed, the resulting product was cooled to normal temperature, and then extraction was performed with distilled water and EA. After the organic layer was dried over anhydrous MgSO₄, the solvent was removed by a rotary evaporator, and then the residue was purified by column chromatography using dichloromethane and hexane as an eluting solvent, thereby obtaining 13.6 g (65%) of Target Compound C-1.

Preparation of Compound C 10 g (21.03 mmol) of Compound C-1, 6.41 g (25.24 mmol) of bis(pinacolato)diboron, 769 mg (1.05 mmol) of PdCl₂(dppf), and 6.19 g (63.09 mmol) of KOAc were dissolved in 100 mL of 1,4-dioxane, and then the resulting solution was stirred at 80° C. for 12 hours. After the reaction was completed, distilled water and DCM were added thereto at room temperature, extraction was performed, the organic layer was dried over MgSO₄, and then the solvent was removed by a rotary evaporator. The reactant was purified with column chromatography (DCM), thereby obtaining 10.76 g (98%) of Target Compound C.

<Synthesis Example 4> Synthesis of Intermediate D

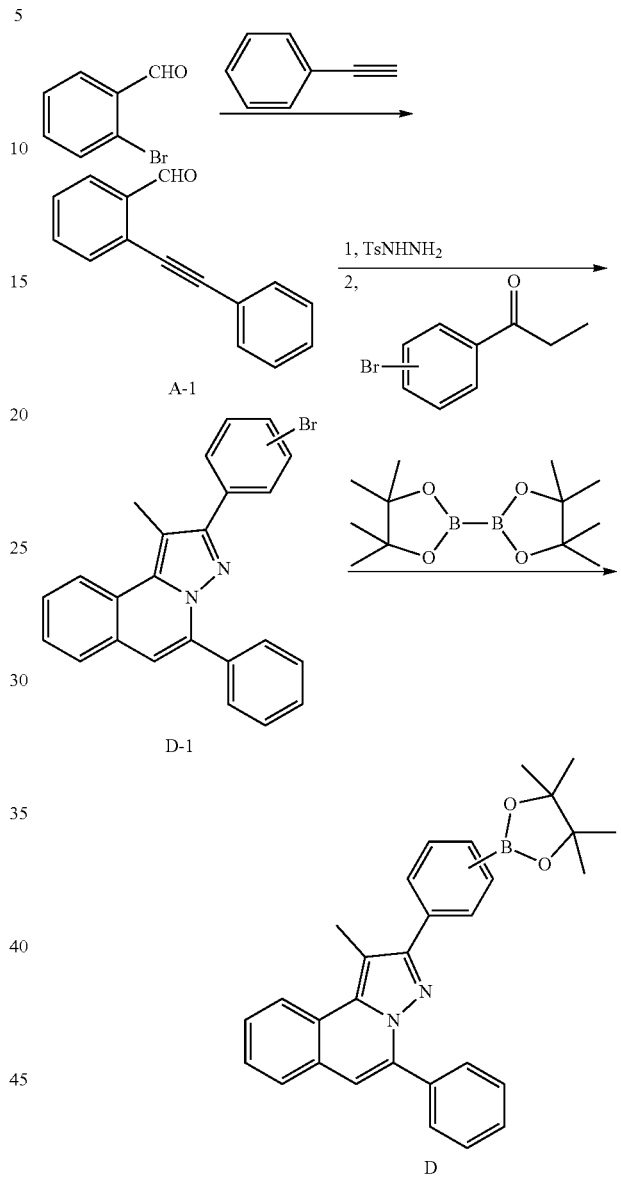

Preparation of Compound D-1

After 9 g (44 mmol) of Compound A-1 was dissolved in ethanol, 8.2 g (44 mmol) of TsNHNH₂ was added thereto, and then the resulting solution was stirred at normal temperature for 20 minutes. 1.1 g (4.4 mmol) of AgOTf was added thereto, and then the resulting mixture was stirred at 70° C. for 30 minutes. After the temperature was cooled to normal temperature, 18.8 g (88 mmol) of 4'-bromopropiophenone or 3'-bromopropiophenone and 37.4 g (176 mmol) of K₃PO₄ were added thereto, and then the resulting mixture was stirred at 70° C. for 17 hours or more. After the reaction was completed, the resulting product was cooled to normal temperature, and then extraction was performed with distilled water and EA. After the organic layer was dried over anhydrous MgSO₄, the solvent was removed by a rotary evaporator, and then the residue was purified by column chromatography using dichloromethane and hexane as an eluting solvent, thereby obtaining 13.3 g (73%) of Target Compound D-1.

Preparation of Compound D 10 g (24.26 mmol) of Compound D-1, 7.4 g (29.12 mmol) of bis(pinacolato)diboron, 885 mg (1.21 mmol) of PdCl$_2$(dppf), and 7.14 g (72.79 mmol) of KOAc were dissolved in 100 mL of 1,4-dioxane, and then the resulting solution was stirred at 80° C. for 12 hours. After the reaction was completed, distilled water and DCM were added thereto at room temperature, extraction was performed, the organic layer was dried over MgSO$_4$, and then the solvent was removed by a rotary evaporator. The reactant was purified with column chromatography (DCM), thereby obtaining 10.6 g (95%) of Target Compound D.

<Preparation Example 1> Preparation of Compound 5

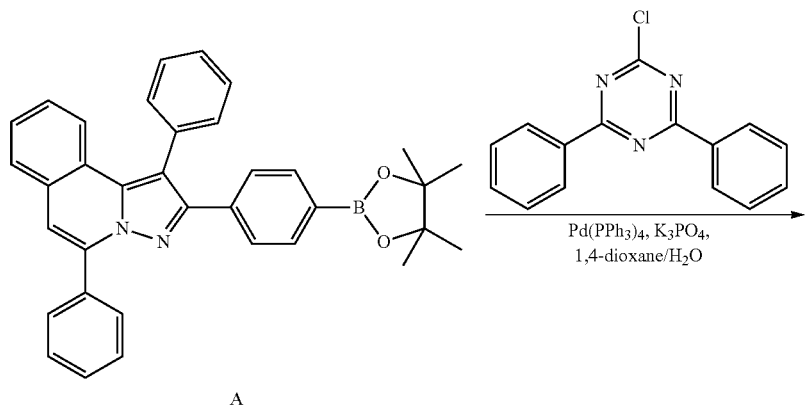

A

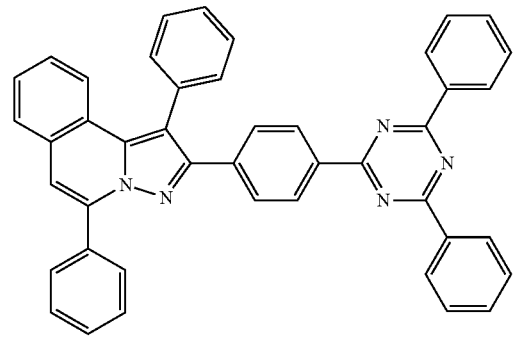

5

10 g (21.72 mmol) of Compound A, 6.39 g (23.89 mmol) of 2-chloro-4,6-diphenyl-1,3,5-triazine, 2.5 g (2.17 mmol) of Pd(PPh$_3$)$_4$, and 65.16 g (13.83 mmol) of K$_3$PO$_4$ were dissolved in 1,4-dioxane/water, and then the resulting solution was refluxed and stirred for about 3 hours. After the reaction was completed, distilled water and DCM were added thereto at room temperature, extraction was performed, the organic layer was dried over MgSO$_4$, and then the solvent was removed by a rotary evaporator. The reactant was purified by column chromatography (DCM:Hex=1:3) and recrystallized with ethyl acetate, thereby obtaining 11.6 g (85%) of a target compound.

<Preparation Example 2> Preparation of Compound 7

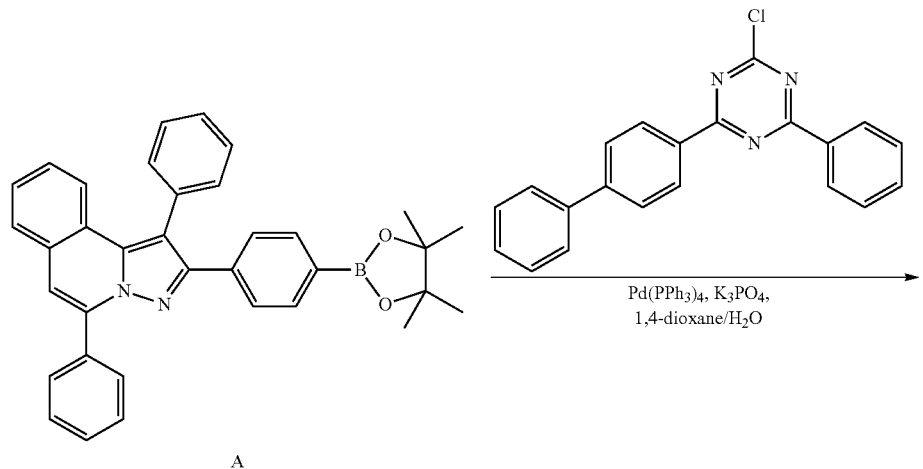

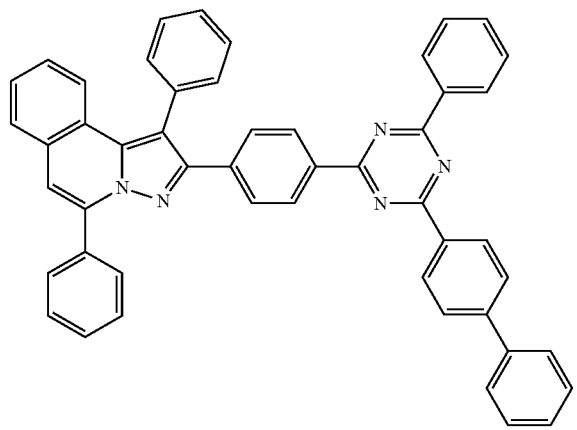

A preparation was performed in the same manner as in the preparation of Compound 5 in Preparation Example 1, except that 2-([1,1'-biphenyl]-4-yl)-4-chloro-6-phenyl-1,3,5-triazine was used instead of the compound 2-chloro-4,6-diphenyl-1,3,5-triazine, thereby obtaining Target Compound 7.

<Preparation Example 3> Preparation of Compound 10

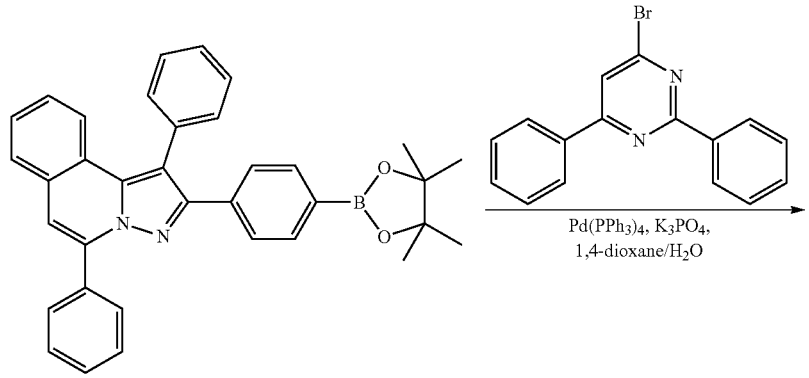

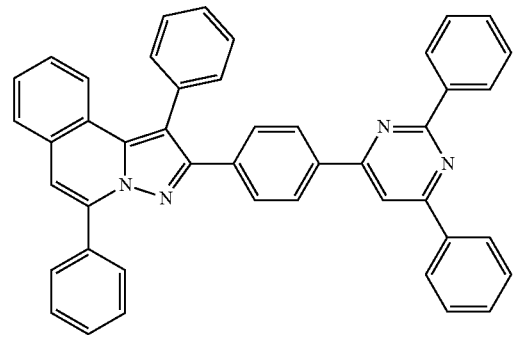

A preparation was performed in the same manner as in the preparation of Compound 5 in Preparation Example 1, except that 4-bromo-2,6-diphenylpyrimidine was used instead of the compound 2-chloro-4,6-diphenyl-1,3,5-triazine, thereby obtaining Target Compound 10.

<Preparation Example 4> Preparation of Compound 11

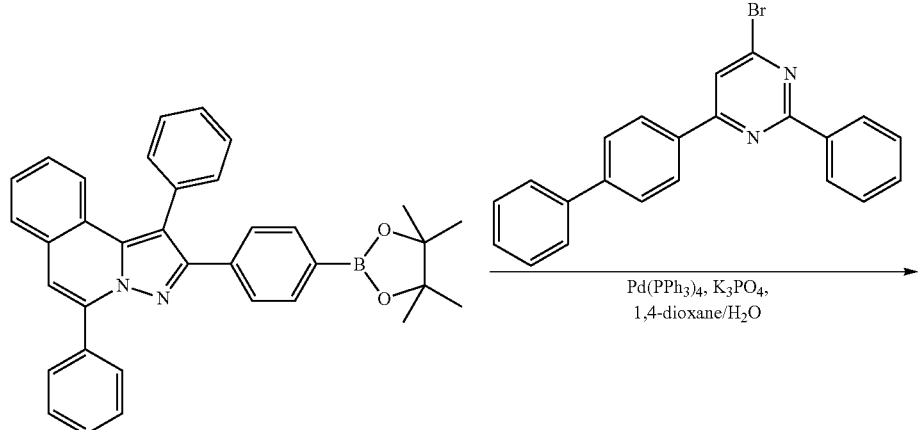

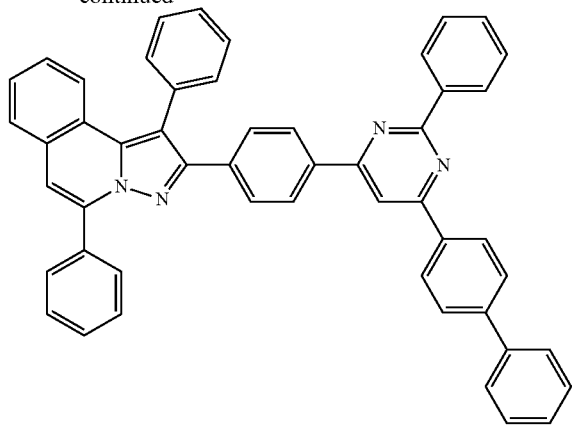
11
A preparation was performed in the same manner as in the preparation of Compound 5 in Preparation Example 1, except that 4-([1,1'-biphenyl]-4-yl)-6-bromo-6-phenylpyrimidine was used instead of the compound 2-chloro-4,6-diphenyl-1,3,5-triazine, thereby obtaining Target Compound 11.
<Preparation Example 5> Preparation of Compound 12
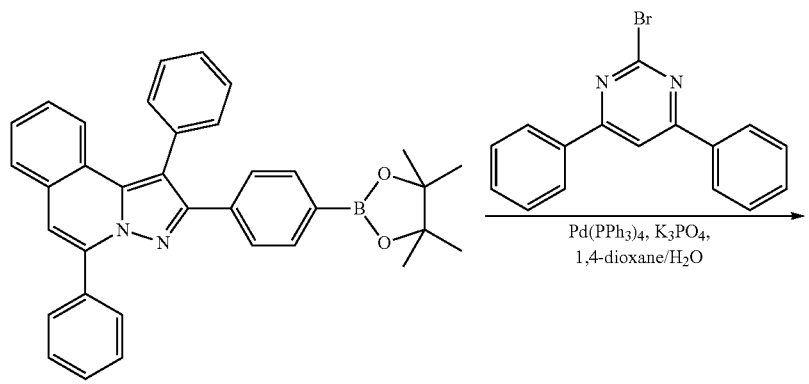
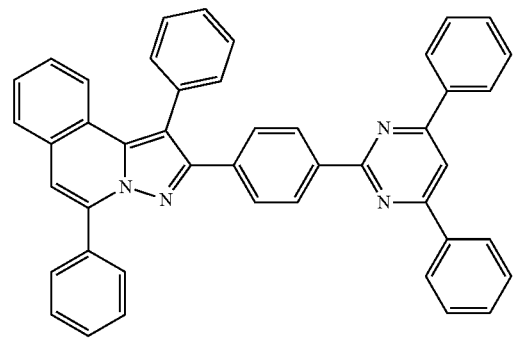
12

A preparation was performed in the same manner as in the preparation of Compound 5 in Preparation Example 1, except that 2-bromo-4,6-diphenylpyrimidine was used instead of the compound 2-chloro-4,6-diphenyl-1,3,5-triazine, thereby obtaining Target Compound 12.

<Preparation Example 6> Preparation of Compound 33

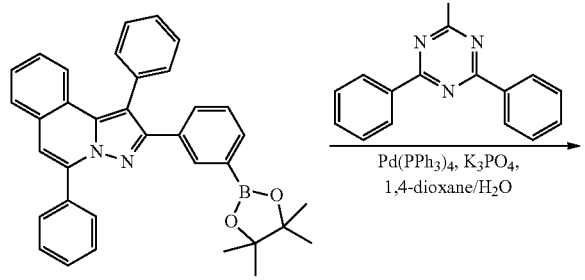

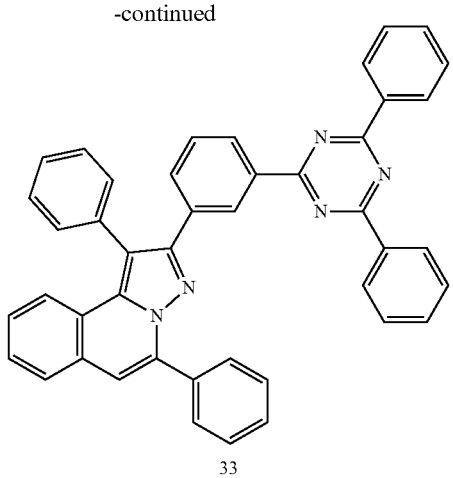

A preparation was performed in the same manner as in the preparation of Compound 5 in Preparation Example 1, thereby obtaining Target Compound 33.

<Preparation Example 7> Preparation of Compound 35

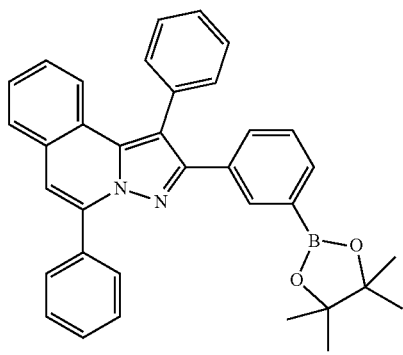

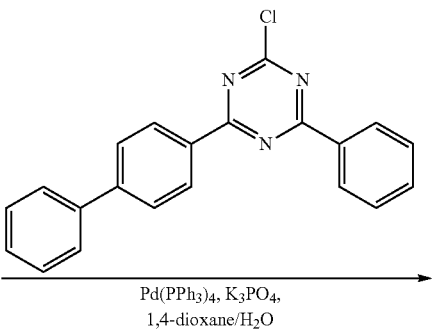

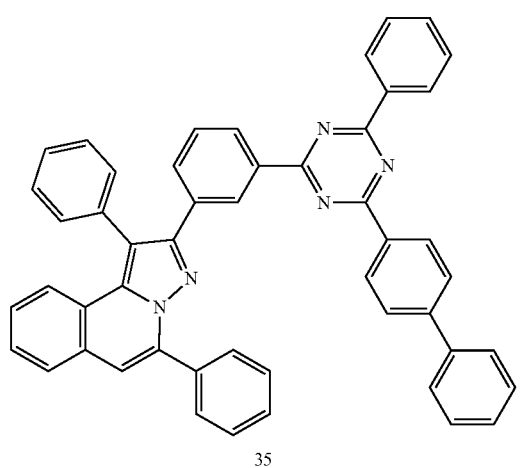

A preparation was performed in the same manner as in the preparation of Compound 7 in Preparation Example 2, thereby obtaining Target Compound 35.

<Preparation Example 8> Preparation of Compound 61

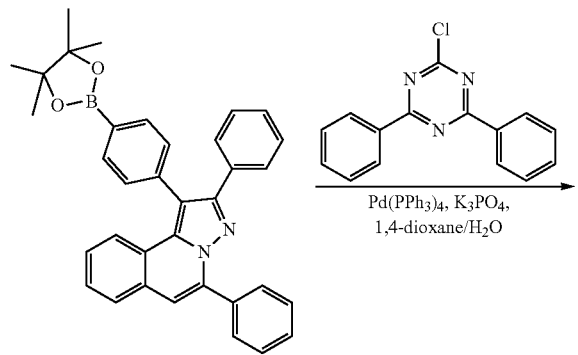

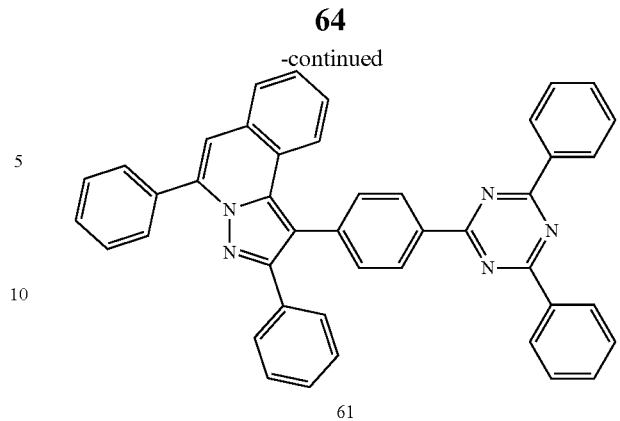

A preparation was performed in the same manner as in the preparation of Compound 5, except that Compound B was used instead of Compound A in Preparation Example 1, thereby obtaining Target Compound 61.

<Preparation Example 9> Preparation of Compound 63

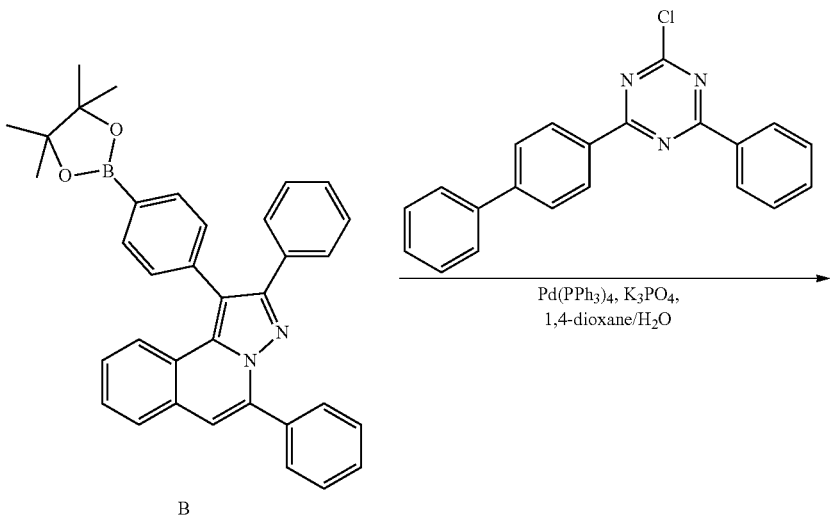

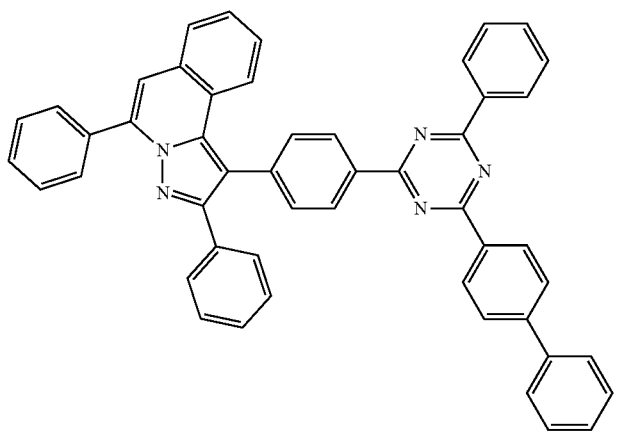

A preparation was performed in the same manner as in the preparation of Compound 7, except that Compound B was used instead of Compound A in Preparation Example 2, thereby obtaining Target Compound 63.

<Preparation Example 10> Preparation of Compound 89

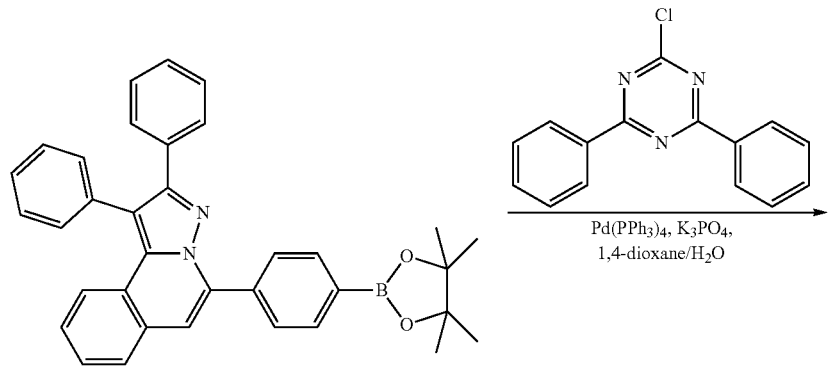

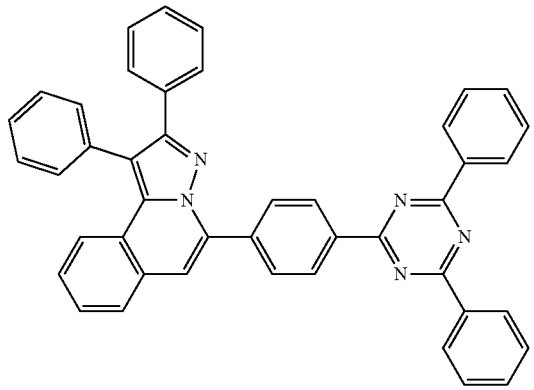

A preparation was performed in the same manner as in the preparation of Compound 5, except that Compound C was used instead of Compound A in Preparation Example 1, thereby obtaining Target Compound 89.

<Preparation Example 11> Preparation of Compound 91

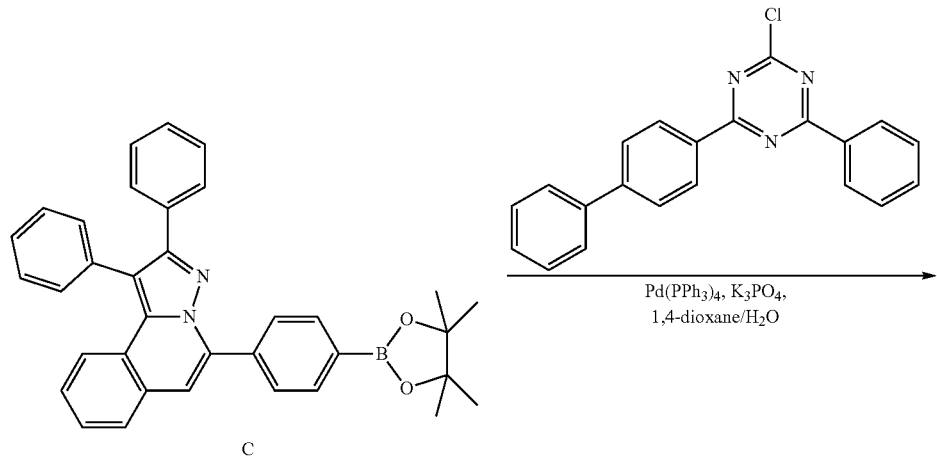

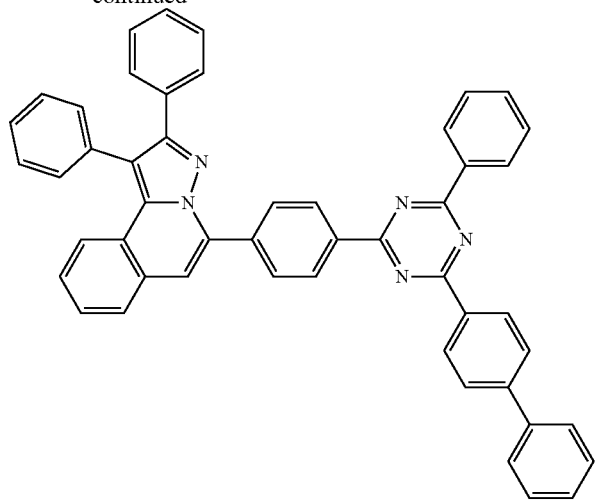
91
A preparation was performed in the same manner as in the preparation of Compound 7, except that Compound C was used instead of Compound A in Preparation Example 2, thereby obtaining Target Compound 91.
<Preparation Example 12> Preparation of Compound 117
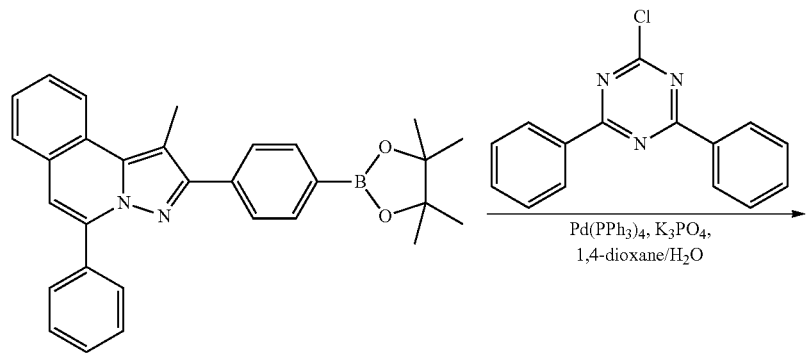
D
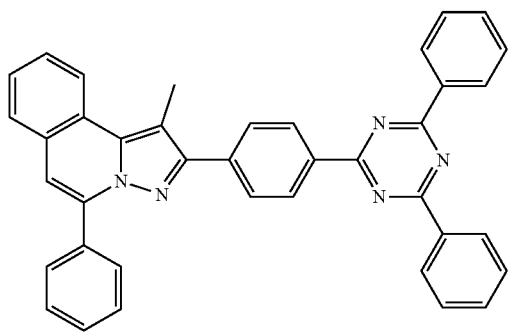
117

A preparation was performed in the same manner as in the preparation of Compound 5, except that Compound D was used instead of Compound A in Preparation Example 1, thereby obtaining Target Compound 117.

<Preparation Example 13> Preparation of Compound 119

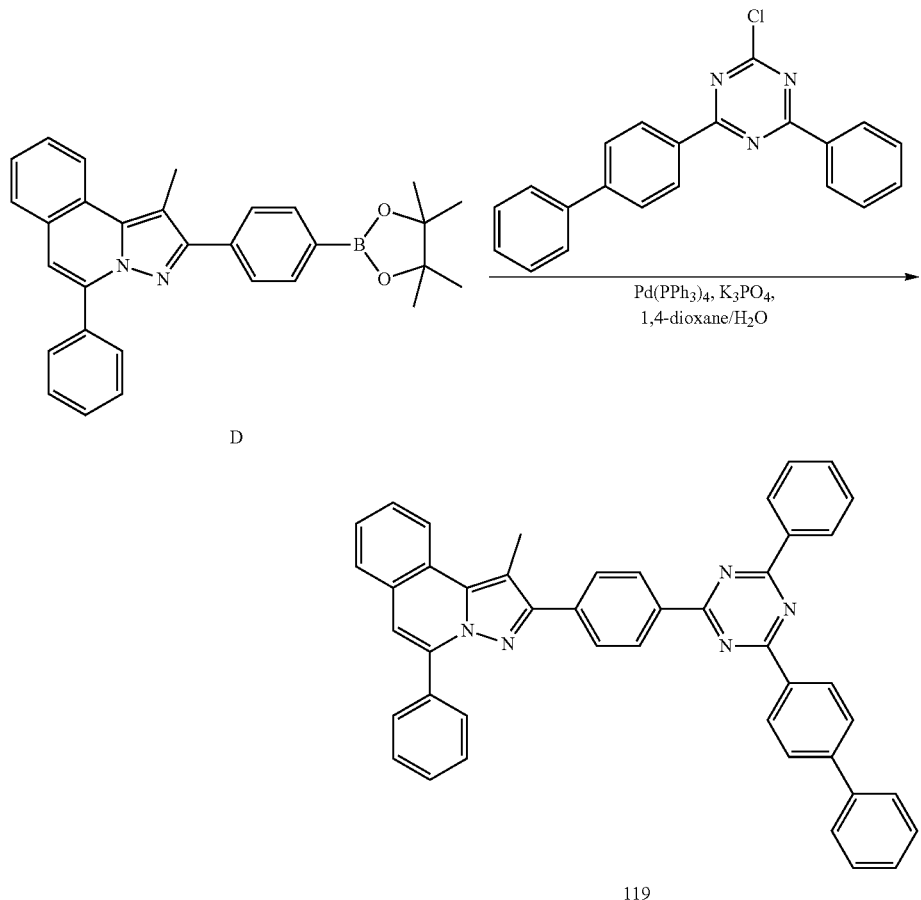

A preparation was performed in the same manner as in the preparation of Compound 7, except that Compound D was used instead of Compound A in Preparation Example 2, thereby obtaining Target Compound 119.

<Preparation Example 14> Preparation of Compound 122

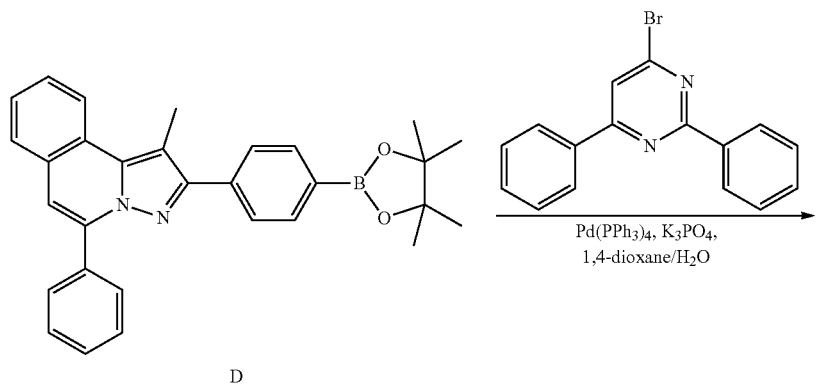

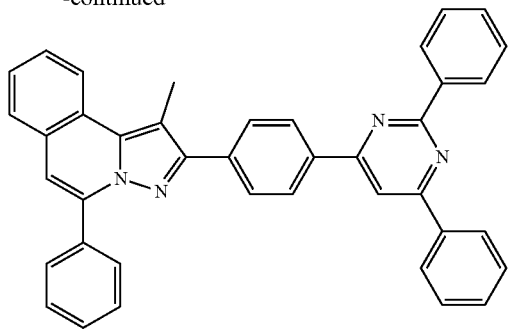
122
A preparation was performed in the same manner as in the preparation of Compound 7, except that Compound D was used instead of Compound A in Preparation Example 3, thereby obtaining Target Compound 122.
<Preparation Example 15> Preparation of Compound 123
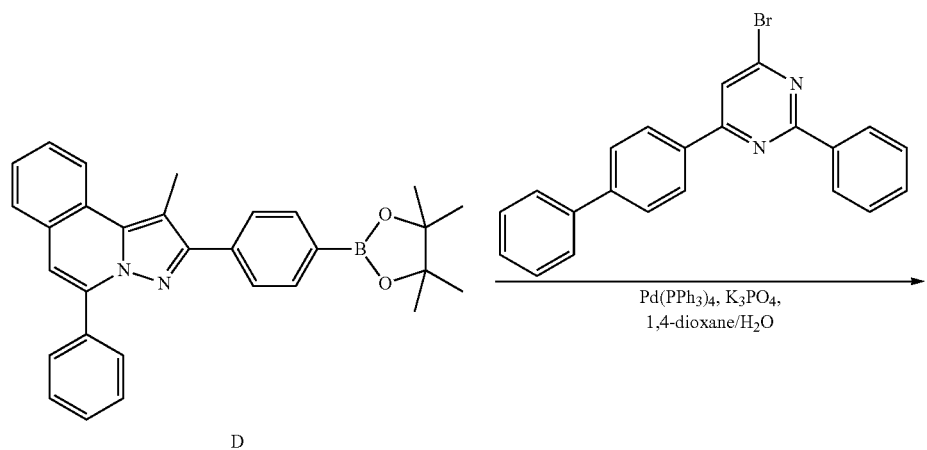
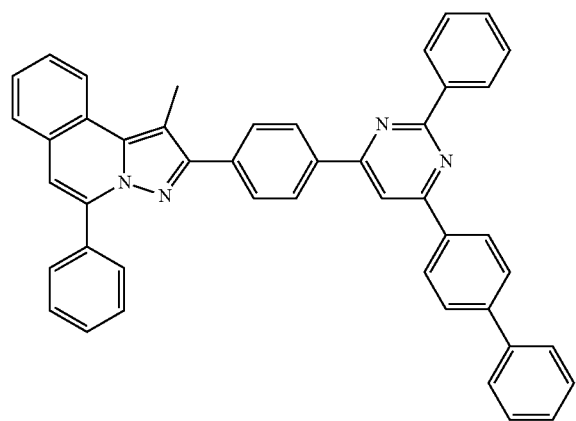
123

A preparation was performed in the same manner as in the preparation of Compound 11, except that Compound D was used instead of Compound A in Preparation Example 4, thereby obtaining Target Compound 123.
<Preparation Example 16> Preparation of Compound 124
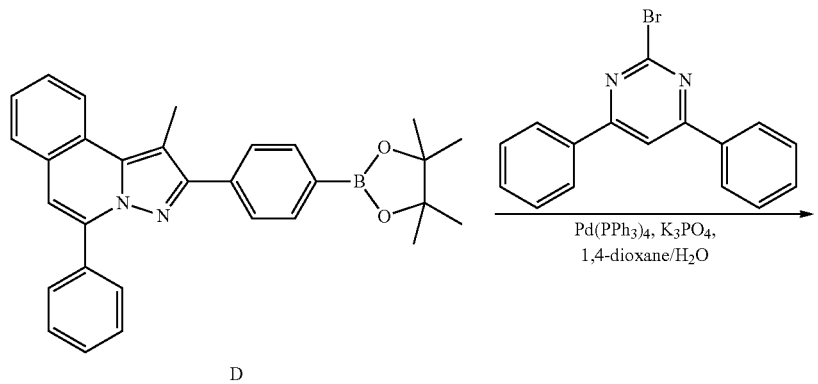
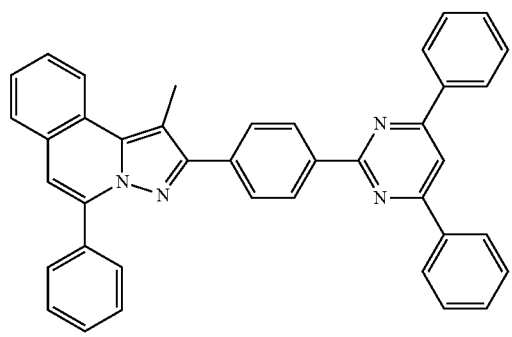

A preparation was performed in the same manner as in the preparation of Compound 12, except that Compound D was used instead of Compound A in Preparation Example 5, thereby obtaining Target Compound 124.

<Preparation Example 17> Preparation of Compound 145

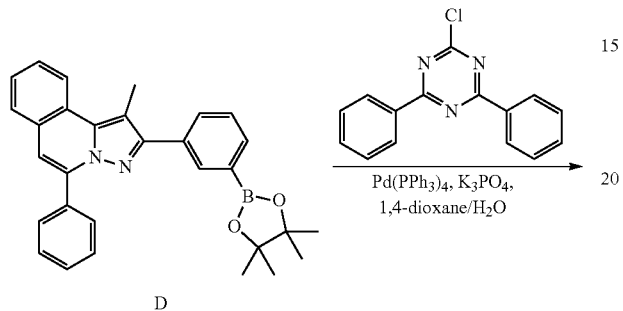

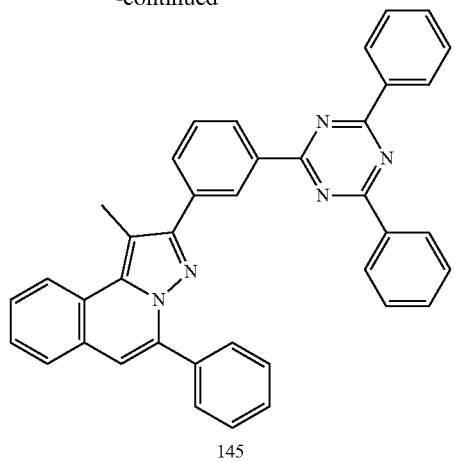

145

A preparation was performed in the same manner as in the preparation of Compound 5, except that Compound D was used instead of Compound A in Preparation Example 1, thereby obtaining Target Compound 145.

<Preparation Example 18> Preparation of Compound 147

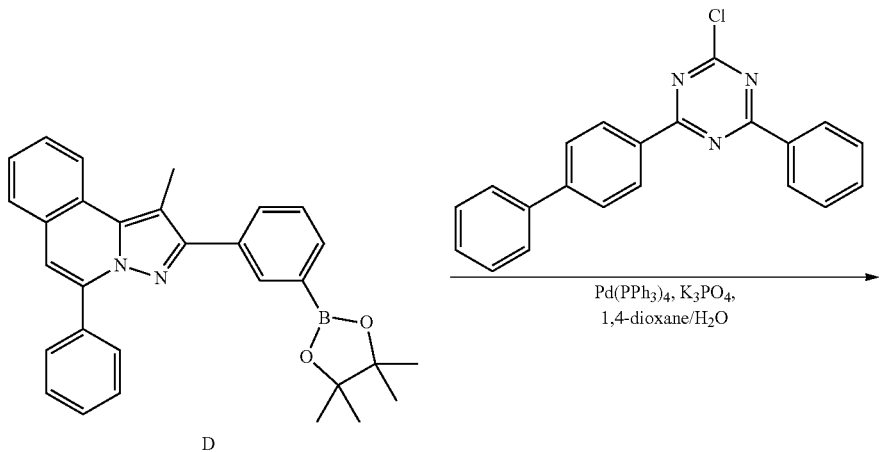

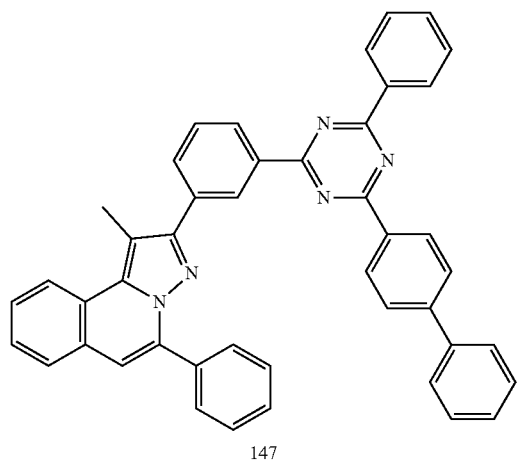

147

A preparation was performed in the same manner as in the preparation of Compound 7, except that Compound D was used instead of Compound A in Preparation Example 2, thereby obtaining Target Compound 147.
<Preparation Example 19> Preparation of Compound 9
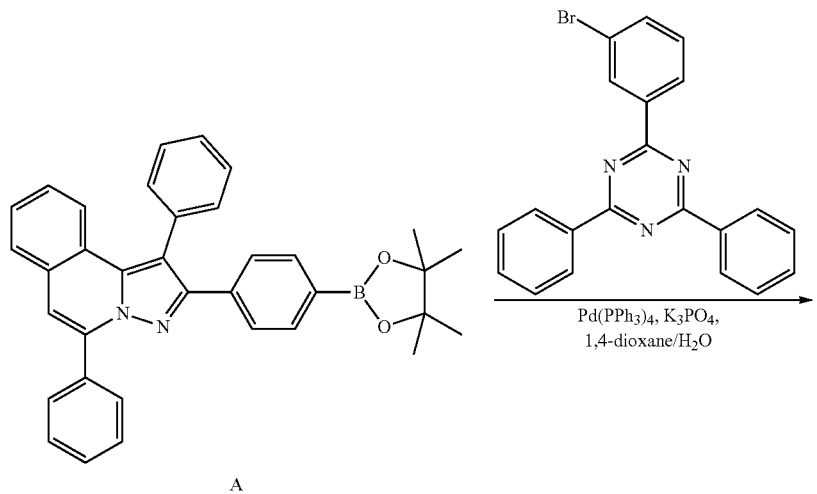

A preparation was performed in the same manner as in the preparation of Compound 5 in Preparation Example 1, except that 2-(3-bromophenyl)-4,6-diphenyl-1,3,5-triazine was used instead of the compound 2-chloro-4,6-diphenyl-1,3,5-triazine, thereby obtaining Target Compound 9.

<Preparation Example 20> Preparation of Compound 20

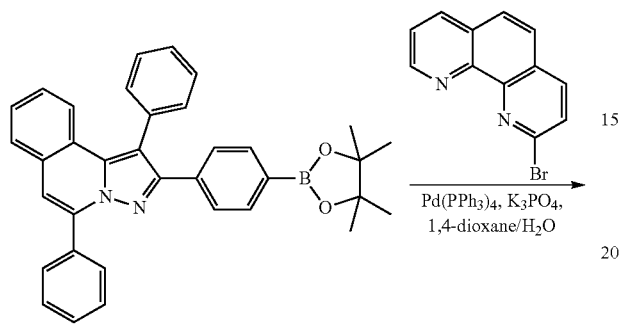

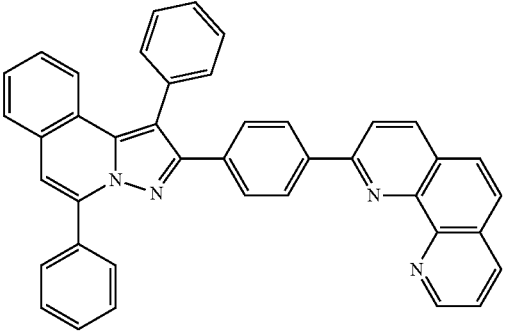

A preparation was performed in the same manner as in the preparation of Compound 5 in Preparation Example 1, except that 2-bromo-1,10-phenanthroline was used instead of the compound 2-chloro-4,6-diphenyl-1,3,5-triazine, thereby obtaining Target Compound 20.

<Preparation Example 21> Preparation of Compound 34

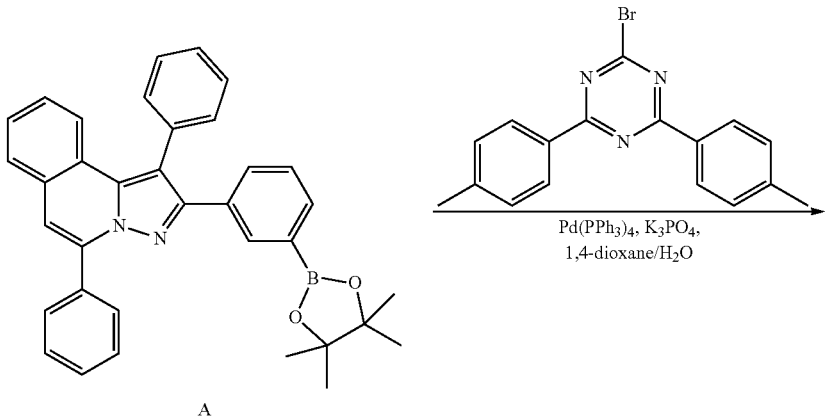

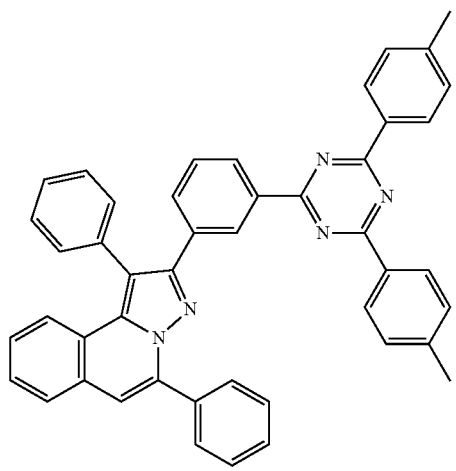

A preparation was performed in the same manner as in the preparation of Compound 5 in Preparation Example 1, except that 2-bromo-4,6-di-p-tolyl-1,3,5-triazine was used instead of the compound 2-chloro-4,6-diphenyl-1,3,5-triazine, thereby obtaining Target Compound 34.
<Preparation Example 22> Preparation of Compound 36
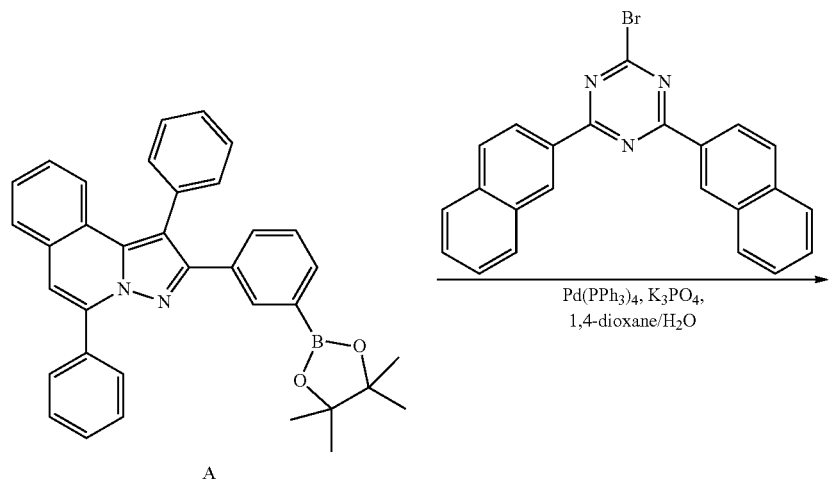
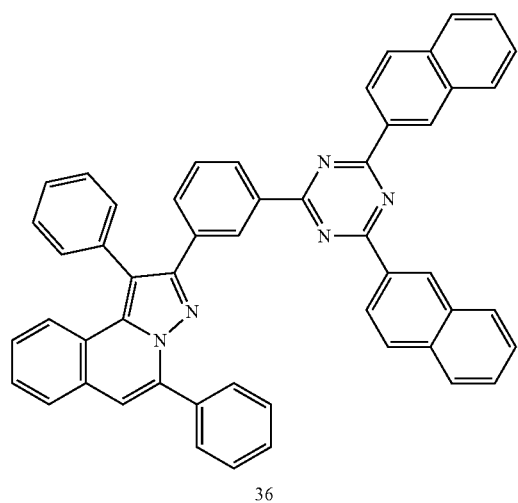

A preparation was performed in the same manner as in the preparation of Compound 5 in Preparation Example 1, except that 2-bromo-4,6-di(naphthalen-2-yl)-1,3,5-triazine was used instead of the compound 2-chloro-4,6-diphenyl-1,3,5-triazine, thereby obtaining Target Compound 36.

<Preparation Example 23> Preparation of Compound 52

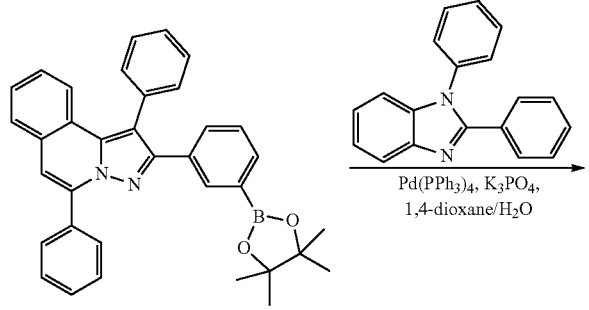

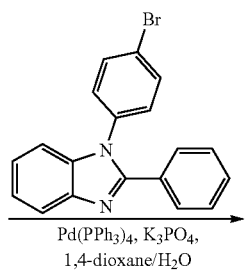

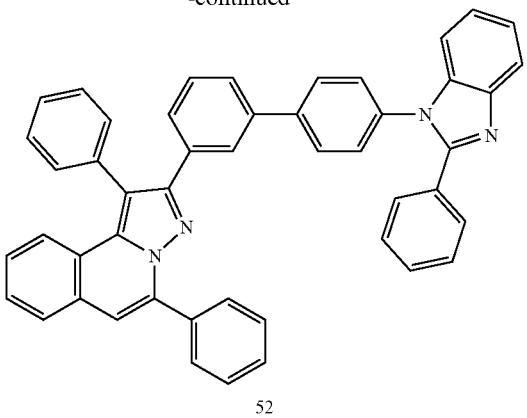

52

A preparation was performed in the same manner as in the preparation of Compound 5 in Preparation Example 1, except that 1-(4-bromophenyl)-2-phenyl-1H-benzo[d]imidazole was used instead of the compound 2-chloro-4,6-diphenyl-1,3,5-triazine, thereby obtaining Target Compound 52.

<Preparation Example 24> Preparation of Compound 169

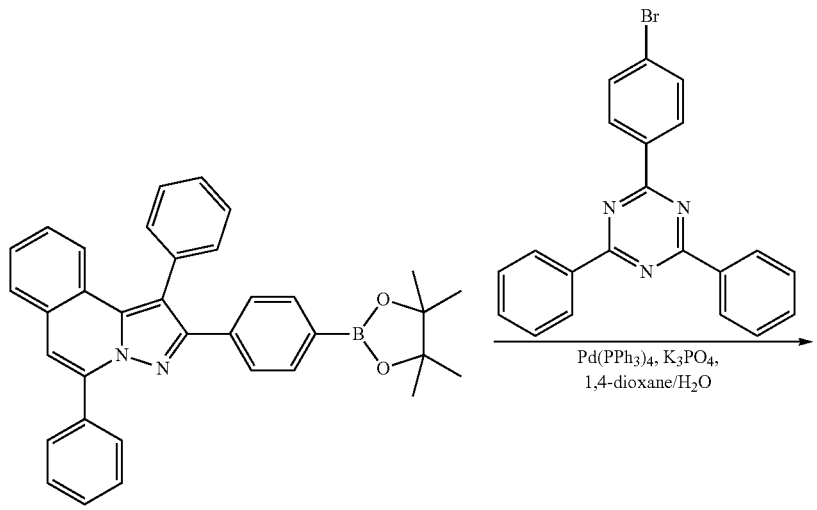

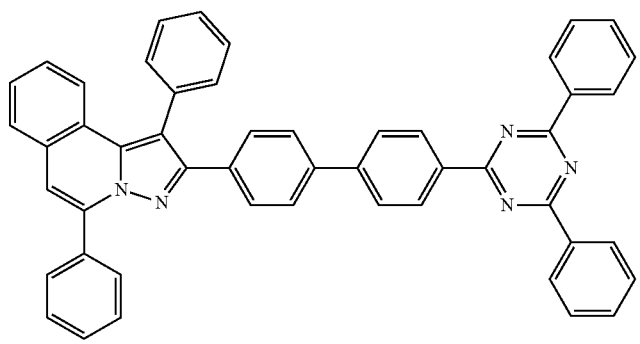

169

A preparation was performed in the same manner as in the preparation of Compound 5 in Preparation Example 1, except that 2-(4-bromophenyl)-4,6-diphenyl-1,3,5-triazine was used instead of the compound 2-chloro-4,6-diphenyl-1,3,5-triazine, thereby obtaining Target Compound 169.

<Preparation Example 25> Preparation of Compound 176

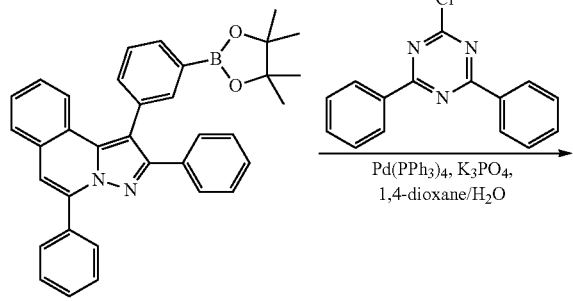

B

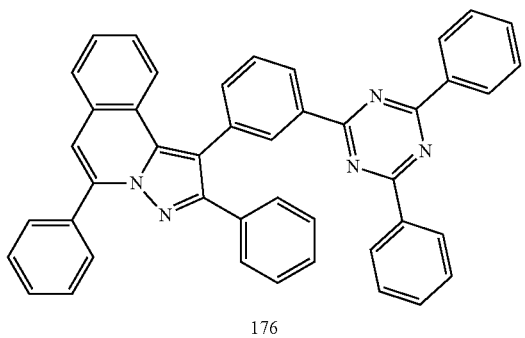

176

A preparation was performed in the same manner as in the preparation of Compound 5, except that Compound B was used instead of Compound A in Preparation Example 1, thereby obtaining Target Compound 176.

<Preparation Example 26> Preparation of Compound 178

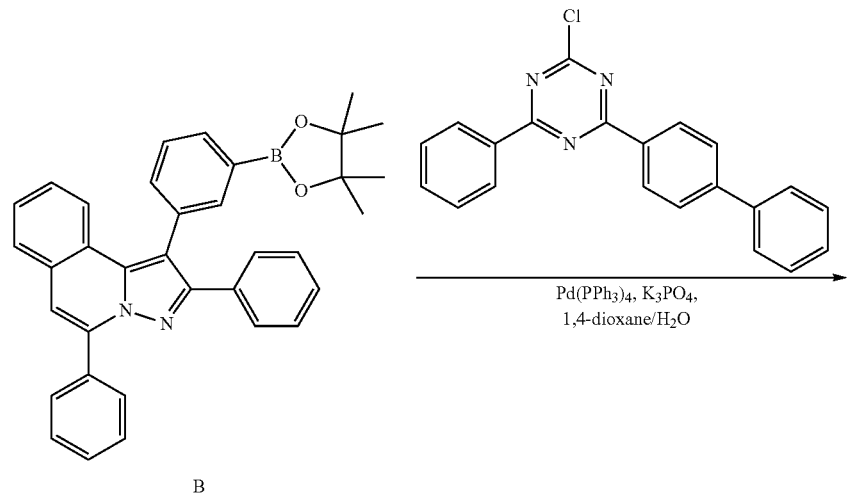

B

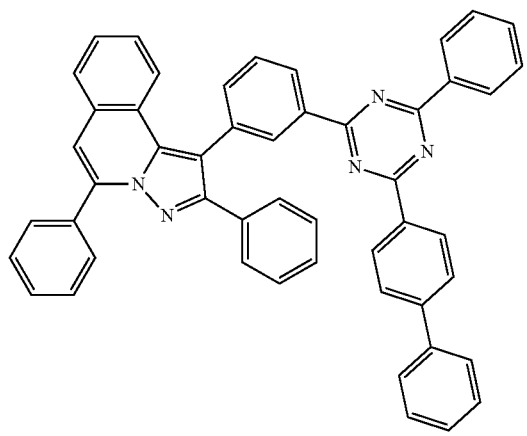

178

A preparation was performed in the same manner as in the preparation of Compound 5, except that Compound B was used instead of Compound A in Preparation Example 1, thereby obtaining Target Compound 178.

<Preparation Example 27> Preparation of Compound 187

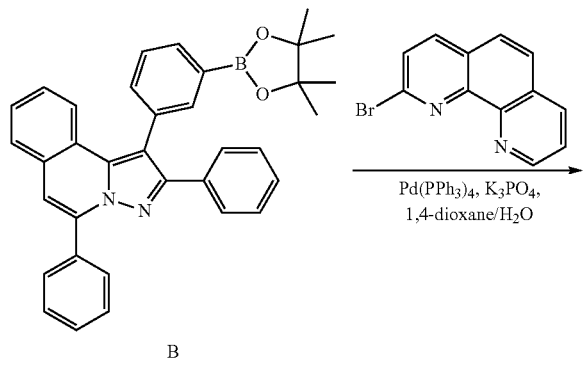

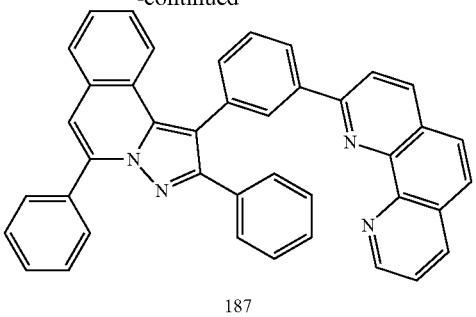

187

A preparation was performed in the same manner as in the preparation of Compound 20, except that Compound B was used instead of Compound A in Preparation Example 1, thereby obtaining Target Compound 187.

Compounds were prepared in the same manner as in the Preparation Examples, and the synthesis confirmation results thereof are shown in the following Tables. Table 1 is about measured values of field desorption mass spectrometry (FD-MS), and Table 2 is about NMR values.

TABLE 1

| Compound | FD-MS | Compound | FD-MS |
|---|---|---|---|
| 5 | m/z = 627.24($C_{44}H_{29}N_5$ = 627.75) | 6 | m/z = 655.27($C_{46}H_{33}N_5$ = 655.80) |
| 7 | m/z = 703.27($C_{50}H_{33}N_5$ = 703.85) | 8 | m/z = 727.27($C_{52}H_{33}N_5$ = 727.87) |
| 9 | m/z = 703.27($C_{50}H_{33}N_5$ = 703.85) | 10 | m/z = 626.25($C_{45}H_{30}N_4$ = 626.76) |
| 11 | m/z = 702.28($C_{51}H_{34}N_4$ = 702.86) | 12 | m/z = 626.25($C_{45}H_{30}N_4$ = 626.76) |
| 13 | m/z = 702.28($C_{51}H_{34}N_4$ = 702.86) | 14 | m/z = 600.23($C_{43}H_{28}N_3$ = 600.73) |
| 19 | m/z = 523.20($C_{38}H_{25}N_3$ = 523.64) | 20 | m/z = 574.22($C_{41}H_{26}N_4$ = 574.69) |
| 23 | m/z = 664.26($C_{48}H_{32}N_4$ = 664.81) | 24 | m/z = 664.26($C_{48}H_{32}N_4$ = 664.81) |
| 25 | m/z = 588.23($C_{42}H_{28}N_4$ = 588.71) | 26 | m/z = 588.23($C_{42}H_{28}N_4$ = 588.71) |
| 27 | m/z = 616.26($C_{44}H_{32}N_4$ = 616.77) | 28 | m/z = 616.26($C_{44}H_{32}N_4$ = 616.77) |
| 33 | m/z = 627.24($C_{44}H_{29}N_5$ = 627.75) | 34 | m/z = 655.27($C_{46}H_{33}N_5$ = 655.80) |
| 35 | m/z = 703.27($C_{50}H_{33}N_5$ = 703.85) | 36 | m/z = 727.27($C_{52}H_{33}N_5$ = 727.87) |
| 37 | m/z = 703.27($C_{50}H_{33}N_5$ = 703.85) | 38 | m/z = 626.25($C_{45}H_{30}N_4$ = 626.76) |
| 39 | m/z = 702.28($C_{51}H_{34}N_4$ = 702.86) | 40 | m/z = 626.25($C_{45}H_{30}N_4$ = 626.76) |
| 41 | m/z = 702.28($C_{51}H_{34}N_4$ = 702.86) | 42 | m/z = 600.23($C_{43}H_{28}N_3$ = 600.73) |
| 47 | m/z = 523.20($C_{38}H_{25}N_3$ = 523.64) | 48 | m/z = 574.22($C_{41}H_{26}N_4$ = 574.69) |
| 51 | m/z = 664.26($C_{48}H_{32}N_4$ = 664.81) | 52 | m/z = 664.26($C_{48}H_{32}N_4$ = 664.81) |
| 53 | m/z = 588.23($C_{42}H_{28}N_4$ = 588.71) | 54 | m/z = 588.23($C_{42}H_{28}N_4$ = 588.71) |
| 55 | m/z = 616.26($C_{44}H_{32}N_4$ = 616.77) | 56 | m/z = 616.26($C_{44}H_{32}N_4$ = 616.77) |
| 61 | m/z = 627.24($C_{44}H_{29}N_5$ = 627.75) | 62 | m/z = 655.27($C_{46}H_{33}N_5$ = 655.80) |
| 63 | m/z = 703.27($C_{50}H_{33}N_5$ = 703.85) | 64 | m/z = 727.27($C_{52}H_{33}N_5$ = 727.87) |
| 65 | m/z = 703.27($C_{50}H_{33}N_5$ = 703.85) | 66 | m/z = 626.25($C_{45}H_{30}N_4$ = 626.76) |
| 67 | m/z = 702.28($C_{51}H_{34}N_4$ = 702.86) | 68 | m/z = 626.25($C_{45}H_{30}N_4$ = 626.76) |
| 69 | m/z = 702.28($C_{51}H_{34}N_4$ = 702.86) | 70 | m/z = 600.23($C_{43}H_{28}N_3$ = 600.73) |
| 75 | m/z = 523.20($C_{38}H_{25}N_3$ = 523.64) | 76 | m/z = 574.22($C_{41}H_{26}N_4$ = 574.69) |
| 79 | m/z = 664.26($C_{48}H_{32}N_4$ = 664.81) | 80 | m/z = 664.26($C_{48}H_{32}N_4$ = 664.81) |
| 81 | m/z = 588.23($C_{42}H_{28}N_4$ = 588.71) | 82 | m/z = 588.23($C_{42}H_{28}N_4$ = 588.71) |
| 83 | m/z = 616.26($C_{44}H_{32}N_4$ = 616.77) | 84 | m/z = 616.26($C_{44}H_{32}N_4$ = 616.77) |
| 89 | m/z = 627.24($C_{44}H_{29}N_5$ = 627.75) | 90 | m/z = 655.27($C_{46}H_{33}N_5$ = 655.80) |
| 91 | m/z = 703.27($C_{50}H_{33}N_5$ = 703.85) | 92 | m/z = 727.27($C_{52}H_{33}N_5$ = 727.87) |
| 93 | m/z = 703.27($C_{50}H_{33}N_5$ = 703.85) | 94 | m/z = 626.25($C_{45}H_{30}N_4$ = 626.76) |
| 95 | m/z = 702.28($C_{51}H_{34}N_4$ = 702.86) | 96 | m/z = 626.25($C_{45}H_{30}N_4$ = 626.76) |
| 97 | m/z = 702.28($C_{51}H_{34}N_4$ = 702.86) | 98 | m/z = 600.23($C_{43}H_{28}N_3$ = 600.73) |
| 103 | m/z = 523.20($C_{38}H_{25}N_3$ = 523.64) | 104 | m/z = 574.22($C_{41}H_{26}N_4$ = 574.69) |
| 107 | m/z = 664.26($C_{48}H_{32}N_4$ = 664.81) | 108 | m/z = 664.26($C_{48}H_{32}N_4$ = 664.81) |
| 109 | m/z = 588.23($C_{42}H_{28}N_4$ = 588.71) | 110 | m/z = 588.23($C_{42}H_{28}N_4$ = 588.71) |
| 111 | m/z = 616.26($C_{44}H_{32}N_4$ = 616.77) | 112 | m/z = 616.26($C_{44}H_{32}N_4$ = 616.77) |
| 117 | m/z = 565.23($C_{39}H_{27}N_5$ = 565.68) | 118 | m/z = 593.26($C_{41}H_{31}N_5$ = 593.73) |
| 119 | m/z = 641.26($C_{45}H_{31}N_5$ = 641.78) | 120 | m/z = 665.26($C_{47}H_{31}N_5$ = 665.80) |
| 121 | m/z = 641.26($C_{45}H_{31}N_5$ = 641.78) | 122 | m/z = 564.23($C_{40}H_{28}N_4$ = 564.69) |
| 123 | m/z = 640.26($C_{46}H_{32}N_4$ = 640.79) | 124 | m/z = 564.23($C_{40}H_{28}N_4$ = 564.69) |
| 125 | m/z = 640.26($C_{46}H_{32}N_4$ = 640.79) | 126 | m/z = 538.22($C_{38}H_{26}N_4$ = 538.65) |
| 131 | m/z = 461.19($C_{33}H_{23}N_3$ = 461.57) | 132 | m/z = 512.20($C_{36}H_{24}N_4$ = 512.60) |
| 135 | m/z = 602.25($C_{43}H_{30}N_4$ = 602.74) | 136 | m/z = 602.25($C_{43}H_{30}N_4$ = 602.74) |
| 137 | m/z = 526.22($C_{37}H_{26}N_4$ = 526.64) | 138 | m/z = 526.22($C_{37}H_{26}N_4$ = 526.64) |
| 139 | m/z = 554.25($C_{39}H_{30}N_4$ = 554.70) | 140 | m/z = 554.25($C_{39}H_{30}N_4$ = 554.70) |
| 145 | m/z = 565.23($C_{39}H_{27}N_5$ = 565.68) | 146 | m/z = 593.26($C_{41}H_{31}N_5$ = 593.73) |
| 147 | m/z = 641.26($C_{45}H_{31}N_5$ = 641.78) | 148 | m/z = 665.26($C_{47}H_{31}N_5$ = 665.80) |

TABLE 1-continued

| Compound | FD-MS | Compound | FD-MS |
|---|---|---|---|
| 149 | m/z = 641.26($C_{45}H_{31}N_5$ = 641.78) | 150 | m/z = 564.23($C_{40}H_{28}N_4$ = 564.69) |
| 151 | m/z = 640.26($C_{46}H_{32}N_4$ = 640.79) | 152 | m/z = 564.23($C_{40}H_{28}N_4$ = 564.69) |
| 153 | m/z = 640.26($C_{46}H_{32}N_4$ = 640.79) | 154 | m/z = 538.22($C_{38}H_{26}N_4$ = 538.65) |
| 159 | m/z = 461.19($C_{33}H_{23}N_3$ = 461.57) | 160 | m/z = 512.20($C_{36}H_{24}N_4$ = 512.60) |
| 163 | m/z = 602.25($C_{43}H_{30}N_4$ = 602.74) | 164 | m/z = 602.25($C_{43}H_{30}N_4$ = 602.74) |
| 165 | m/z = 526.22($C_{37}H_{26}N_4$ = 526.64) | 166 | m/z = 526.22($C_{37}H_{26}N_4$ = 526.64) |
| 167 | m/z = 554.25($C_{39}H_{30}N_4$ = 554.70) | 168 | m/z = 554.25($C_{39}H_{30}N_4$ = 554.70) |
| 169 | m/z = 703.27($C_{50}H_{33}N_5$ = 703.85) | 170 | m/z = 703.27($C_{50}H_{33}N_5$ = 703.85) |
| 171 | m/z = 641.26($C_{45}H_{31}N_5$ = 641.78) | 172 | m/z = 641.26($C_{45}H_{31}N_5$ = 641.78) |
| 173 | m/z = 703.27($C_{50}H_{33}N_5$ = 703.85) | 174 | m/z = 703.27($C_{50}H_{33}N_5$ = 703.85) |
| 175 | m/z = 703.27($C_{50}H_{33}N_5$ = 703.85) | 176 | m/z = 627.24($C_{44}H_{29}N_5$ = 627.75) |
| 177 | m/z = 655.27($C_{46}H_{33}N_5$ = 655.80) | 178 | m/z = 703.27($C_{50}H_{33}N_5$ = 703.85) |
| 179 | m/z = 727.27($C_{52}H_{33}N_5$ = 727.87) | 180 | m/z = 703.27($C_{50}H_{33}N_5$ = 703.85) |
| 181 | m/z = 626.25($C_{45}H_{30}N_4$ = 626.76) | 182 | m/z = 702.28($C_{51}H_{34}N_4$ = 702.86) |
| 183 | m/z = 626.25($C_{45}H_{30}N_4$ = 626.76) | 184 | m/z = 702.28($C_{51}H_{34}N_4$ = 702.86) |
| 185 | m/z = 600.23($C_{43}H_{28}N_3$ = 600.73) | 186 | m/z = 523.20($C_{38}H_{25}N_3$ = 523.64) |
| 187 | m/z = 574.22($C_{41}H_{26}N_4$ = 574.69) | 188 | m/z = 664.26($C_{48}H_{32}N_4$ = 664.81) |
| 189 | m/z = 664.26($C_{48}H_{32}N_4$ = 664.81) | 190 | m/z = 588.23($C_{42}H_{28}N_4$ = 588.71) |
| 191 | m/z = 588.23($C_{42}H_{28}N_4$ = 588.71) | 192 | m/z = 616.26($C_{44}H_{32}N_4$ = 616.77) |
| 193 | m/z = 616.26($C_{44}H_{32}N_4$ = 616.77) | | |

TABLE 2

| Compound | $^1$H NMR(CDCl$_3$, 300 Mz) |
|---|---|
| 5 | δ = 8.36(4H, m), 8.30(2H, d), 8.05(1H, d), 7.96(2H, d), 7.70~7.62(4H, m), 7.51~7.41(14H, m), 7.08(2H, t) |
| 7 | δ = 8.36(2H, t), 8.30(2H, d), 8.05(1H, t), 7.96(4H, d), 7.75(2H, d), 7.70(2H, d), 7.62(2H, m), 7.50~7.41(14H, m), 7.25(2H, d), 7.08(2H, t) |
| 9 | δ = 8.83~8.30(7H,m), 8.05(1H, t), 7.94(1H, s), 7.85(2H, d), 7.73~7.61(6H, m), 7.51~7.41(14H, m), 7.08(2H, t) |
| 10 | δ = 8.35(2H, m), 8.30(4H, s), 8.23(1H, s), 8.05(1H, t), 7.94(1H, d), 7.70~7.55(7H, m), 7.50~7.41(11H, m), 7.08(2H, t) |
| 11 | δ = 8.35(2H, m), 8.30(6H, t), 8.23(1H, s), 8.05(1H, t), 7.85(2H, d), 7.75(2H, d), 7.70(2H, d), 7.62(2H, m), 7.51~7.41(14H, m), 7.08(2H, t) |
| 12 | δ = 8.30(2H, d), 8.23(1H, s), 8.05(1H, d), 7.96~7.94(6H, m), 7.70~7.55(8H, m), 7.51~7.41(10H, m), 7.08(2H, t) |
| 20 | δ = 8.80(1H, d), 8.71~8.69(3H,t), 8.45(1H, d), 8.30(2H, d), 8.20(1H, d), 8.05(1H, d), 7.90(1H, d) 7.70~7.62(4H, m), 7.56~7.41(9H,m), 7.29(1H, d), 7.08(2H, d) |
| 33 | δ = 8.38~8.36(5H, m), 8.05(1H, t), 7.94(2H, m), 7.73~7.62(5H, m), 7.50~7.41(14H, m), 7.08(2H, t) |
| 34 | δ = 8.60(4H, d), 8.38(1H, d), 8.05(1H, d), 7.94(2H, t), 7.73~7.62(5H,m), 7.47~7.45(12H, m), 2.34(6H, s) |
| 35 | δ = 8.38~8.36(3H, m), 8.05(1H, t), 7.96~7.94(4H, m), 7.75~7.62(7H, m), 7.51~7.41(14H, m), 7.25(2H, d), 7.08(2H, t) |
| 36 | δ = 9.09(2H, s), 8.49(2H, d), 8.38(1H, d), 8.16(2H, d), 8.08(2H, d), 8.05~7.94(5H, m), 7.70~7.62(4H, m), 7.61~7.41(13H, m), 7.08(2H, t) |
| 52 | δ = 8.56(1H, d), 8.28(2H, d), 8.05(1H, d), 7.94(2H, d), 7.81~7.73(6H, m), 7.70~7.62(4H, m), 7.53~7.41(13H, m), 7.28(1H, t), 7.08(2H, t) |
| 61 | δ = 8.36(4H, t), 8.05(1H, d), 7.96(2H, d), 7.84(2H, d), 7.70~7.62(4H, m), 7.53~7.47(12H, m), 7.25(2H, d), 7.08(2H, t) |
| 63 | δ = 8.36(2H, t), 8.05(1H, t), 7.96(4H, d), 7.84(2H, d), 7.75(2H, d), 7.70(1H, t), 7.62(2H, m), 7.53~7.41(13H, m), 7.25(4H, d), 7.08(2H, t) |
| 89 | δ = 8.69(2H, d), 8.36(4H, t), 8.05(1H, d), 7.96(2H, d), 7.84(2H, d), 7.70~7.62(6H, m), 7.53~7.41(12H, m) |
| 91 | δ = 8.69(2H, d), 8.36(2H, t), 8.05(1H, t), 7.96(4H, d), 7.84(2H, d), 7.75~7.62(6H, m), 7.53~7.41(14H, m), 7.25(2H, d) |
| 117 | δ = 8.36(4H, t), 8.30(2H, d), 8.05(1H, t), 7.96(2H, d), 7.70~7.62(4H, m), 7.50~7.47(9H, m), 7.08(2H t), 2.12(3H, s) |
| 119 | δ = 8.36(2H, t), 8.30(2H, d), 8.05(1H, t), 7.96(4H, d), 7.75(2H, d), 7.70~7.62(4H, m), 7.50~7.41(9H, m), 7.25(2H, d), 7.08(2H, t), 2.12(3H, s) |
| 122 | δ = 8.35(2H, t), 8.30(4H, s), 8.23(1H, s), 8.05(1H, d), 7.94(2H, d), 7.70~7.62(4H, m), 7.55~7.49(9H, m), 7.08(2H, t), 2.12(3H, s) |
| 123 | δ = 8.35(2H, t), 8.30(6H, t), 8.23(1H, s), 8.05(1H, d), 7.85(2H, d), 7.75(2H, d), 7.70~7.62(4H, m), 7.50~7.41(9H, m), 7.08(2H, t), 2.12(3H, s) |
| 124 | δ = 8.30(2H, d), 8.23(1H, s), 8.05(1H, s), 7.96~7.94(6H, m), 7.70~7.62(4H, m), 7.55~7.49(9H, m), 7.08(2H, t), 2.12(3H, s) |
| 145 | δ = 8.38~8.36(5H, m), 8.05(1H,d), 7.94(2H, m), 7.73(1H, t), 7.70~7.62(4H, m), 7.50~7.47(9H, m), 7.08(2H, t), 2.12(3H, s) |
| 147 | δ = 8.38~8.36(3H, m), 8.05(1H,d), 7.96~7.64(4H, m), 7.73(1H, t), 7.70~7.62(6H, m), 7.50~7.41(9H, m), 7.25(2H, d), 7.08(2H, t), 2.12(3H, s) |
| 169 | 6 = 8.36(4H, m), 8.30(2H, d), 8.05(1H, d), 7.96(2H, d), 7.85(2H, d), 7.70~7.62(4H, m), 7.50~7.41(14H, m), 7.25(2H, d), 7.08(2H, t) |

TABLE 2-continued

| Compound | $^1$H NMR(CDCl$_3$, 300 Mz) |
|---|---|
| 176 | δ = 8.38~8.36(5H, m), 8.05(1H, d), 7.94(1H, s), 7.84(2H, d), 7.73~7.61(6H, m), 7.53~7.49(12H, m), 7.08(2H, t) |
| 178 | δ = 8.38~8.36(3H, m), 8.05(1H, d), 7.96~7.94(3H, m), 7.84(2H, d), 7.75~7.62(7H, m), 7.50~7.41(13H, m), 7.25(2H, d), 7.08(2H, t) |
| 187 | δ = 8.80(1H, d), 8.71(1H, d), 8.45(1H, d), 8.33(1H, s), 8.20(1H, d), 8.05(1H, d), 7.90~7.84(3H, m), 7.73~7.62(5H, m), 7.56~7.47(8H, m), 7.29(1H, d), 7.08(2H, t) |

Meanwhile, FIGS. 4 to 35 are graphs showing the light emission absorption spectra obtained by measuring photoluminescence (PL) or low temperature photoluminescence (LTPL) of the compounds in a specific UV wavelength region.

PL was measured at normal temperature by using a model name LS55 spectrometer manufactured by Perkin Elmer Inc., and LTPL was measuring by using a model name F7000 spectrometer manufactured by HITACHI, Ltd., and an analysis was made under the low temperature condition of −196° C. (77 K) by using liquid nitrogen.

FIG. 4 illustrates a measurement graph of LTPL of Compound 5.
FIG. 5 illustrates a measurement graph of PL of Compound 5.
FIG. 6 illustrates a measurement graph of LTPL of Compound 7.
FIG. 7 illustrates a measurement graph of PL of Compound 7.
FIG. 8 illustrates a measurement graph of LTPL of Compound 9.
FIG. 9 illustrates a measurement graph of PL of Compound 9.
FIG. 10 illustrates a measurement graph of LTPL of Compound 10.
FIG. 11 illustrates a measurement graph of PL of Compound 10.
FIG. 12 illustrates a measurement graph of LTPL of Compound 11.
FIG. 13 illustrates a measurement graph of PL of Compound 11.
FIG. 14 illustrates a measurement graph of LTPL of Compound 12.
FIG. 15 illustrates a measurement graph of PL of Compound 12.
FIG. 16 illustrates a measurement graph of LTPL of Compound 20.
FIG. 17 illustrates a measurement graph of PL of Compound 20.
FIG. 18 illustrates a measurement graph of LTPL of Compound 33.
FIG. 19 illustrates a measurement graph of PL of Compound 33.
FIG. 20 illustrates a measurement graph of LTPL of Compound 34.
FIG. 21 illustrates a measurement graph of PL of Compound 34.
FIG. 22 illustrates a measurement graph of LTPL of Compound 35.
FIG. 23 illustrates a measurement graph of PL of Compound 35.
FIG. 24 illustrates a measurement graph of LTPL of Compound 52.
FIG. 25 illustrates a measurement graph of PL of Compound 52.
FIG. 26 illustrates a measurement graph of LTPL of Compound 117.
FIG. 27 illustrates a measurement graph of PL of Compound 117.
FIG. 28 illustrates a measurement graph of LTPL of Compound 122.
FIG. 29 illustrates a measurement graph of PL of Compound 122.
FIG. 30 illustrates a measurement graph of LTPL of Compound 123.
FIG. 31 illustrates a measurement graph of PL of Compound 123.
FIG. 32 illustrates a measurement graph of LTPL of Compound 124.
FIG. 33 illustrates a measurement graph of PL of Compound 124.
FIG. 34 illustrates a measurement graph of LTPL of Compound 169.
FIG. 35 illustrates a measurement graph of PL of Compound 169.

Comparative Example 1

Trichloroethylene, acetone, ethanol, and distilled water were each sequentially used to ultrasonically wash a transparent electrode ITO thin film obtained from glass for OLED (manufactured by Samsung-Corning Co., Ltd.) for 5 minutes, and then the ITO thin film was placed in isopropanol, stored, and then used.

Next, the ITO substrate was disposed in a substrate folder of a vacuum deposition equipment, and the following 4,4', 4"-tris(N,N-(2-naphthyl)-phenylamino)triphenyl amine (2-TNATA) was placed in a cell in the vacuum deposition equipment.

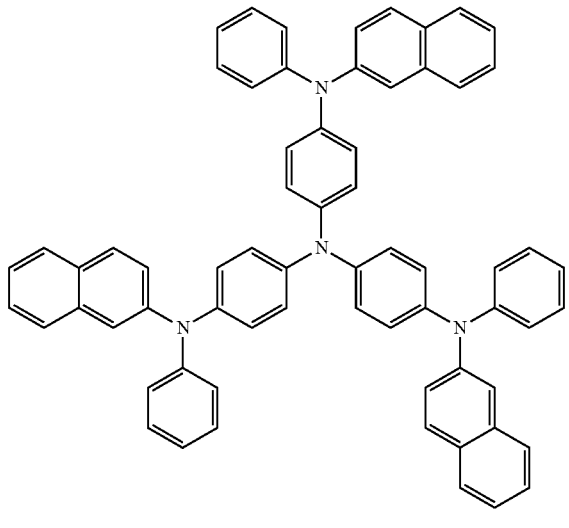

2-TNATA

Subsequently, air in the chamber was evacuated until the degree of vacuum in the chamber reached 10$^{-6}$ torr, and then a hole injection layer having a thickness of 600 Å was deposited on the ITO substrate by applying current to the cell to evaporate 2-TNATA.

A hole transporting layer having a thickness of 300 Å was deposited on the hole injection layer by placing the following N,N'-bis(α-naphthyl)-N,N'-diphenyl-4,4'-diamine (NPB) in another cell in the vacuum deposition equipment and applying current to the cell to evaporate NPB.

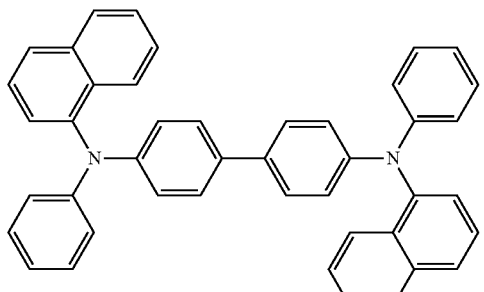

NPB

The hole injection layer and the hole transporting layer were formed as described above, and then a blue light emitting material having the following structure as a light emitting layer was deposited thereon. Specifically, a blue light emitting host material H1 was vacuum deposited to have a thickness of 200 Å on one cell in the vacuum deposition equipment, and a blue light emitting dopant material D1 was vacuum deposited thereon in an amount of 5% based on the host material.

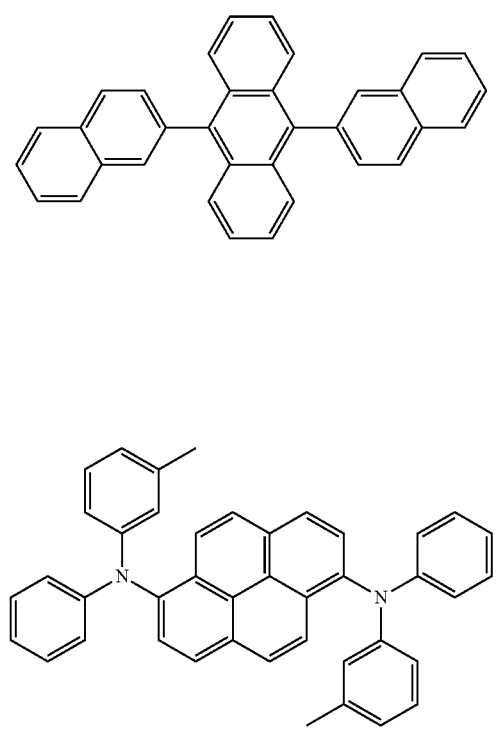

H1

D1

Subsequently, a compound having the following structural formula E 1 (Comparative Compound 1) as an electron transporting layer was deposited to have a thickness of 300 Å.

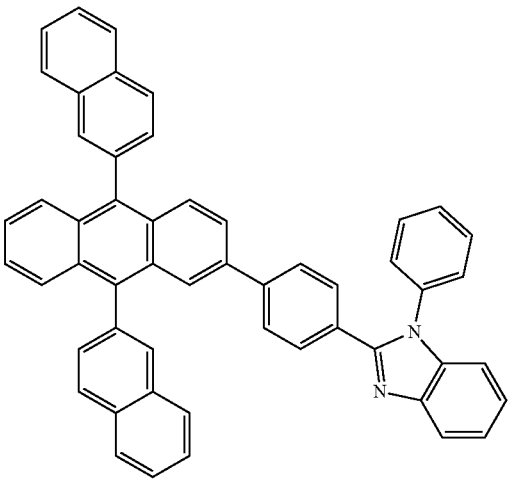

E1

An OLED was manufactured by depositing lithium fluoride (LiF) as an electron injection layer to have a thickness of 10 Å and allowing the Al negative electrode to have a thickness of 1,000 Å.

Meanwhile, all the organic compounds required for manufacturing an OLED were subjected to vacuum sublimed purification under $10^{-6}$ to $10^{-8}$ torr for each material, and used for the manufacture of OLED.

Comparative Examples 2 to 6

Organic electroluminescence devices according to Comparative Examples 2 to 6 were manufactured in the same manner as in Comparative Example 1, except that the following Structural Formulae E2, E3, E4, E5, and E6 were used instead of E1 used when an electron transporting layer was formed in Comparative Example 1.

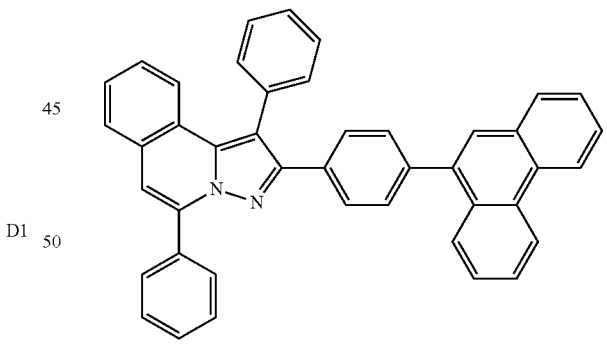

E2

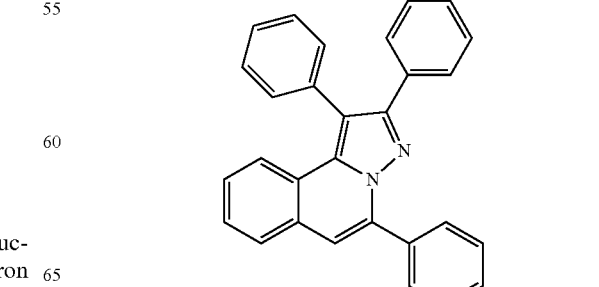

E3

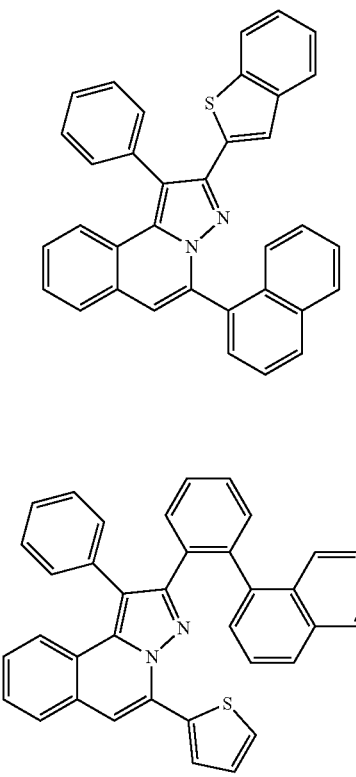

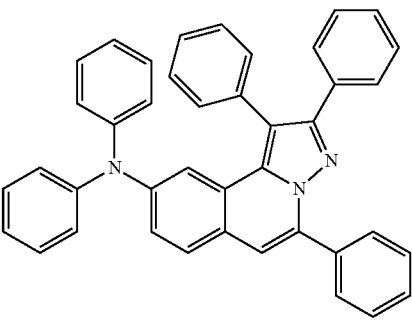

Example 1

An organic electroluminescence device was manufactured in the same manner as in Comparative Example 1, except that the compound synthesized in the present invention was used instead of E1 used when an electron transporting layer was formed in Comparative Example 1.

<Experimental Example> Evaluation of Organic Electroluminescence Device

For each of the organic electroluminescence devices manufactured in Comparative Examples 1 and 6 and Examples 1 to 27, the driving voltage, the efficiency, the color coordinate, and the durability (service life) were measured at a light emitting brightness of 700 cd/m² and evaluated, and the results are as shown in the following Table 3.

TABLE 3

| Experimental Example | Electron transporting layer material | Driving voltage (V) | Efficiency (cd/A) | Color coordinate (x, y) | Service life ($T_{50}$) |
|---|---|---|---|---|---|
| Comparative Example 1 | E1 | 4.7 | 4.5 | (0.15, 0.18) | 330 |
| Comparative Example 2 | E2 | 5.5 | 3.7 | (0.15, 0.19) | 300 |
| Comparative Example 3 | E3 | 6.5 | 2.4 | (0.15, 0.18) | 150 |
| Comparative Example 4 | E4 | 7.2 | 3.1 | (0.15, 0.18) | 22 |
| Comparative Example 5 | E5 | 6.6 | 1.8 | (0.15, 0.17) | 260 |
| Comparative Example 6 | E6 | 5.9 | 4.0 | (0.15, 0.18) | 15 |
| Examples | Compound 5 | 4.7 | 4.8 | (0.15, 0.18) | 450 |
|  | Compound 7 | 4.6 | 4.5 | (0.15, 0.18) | 500 |
|  | Compound 9 | 4.5 | 4.4 | (0.15, 0.17) | 550 |
|  | Compound 10 | 4.6 | 4.9 | (0.15, 0.18) | 440 |
|  | Compound 11 | 4.4 | 5.0 | (0.15, 0.17) | 480 |
|  | Compound 12 | 4.6 | 4.5 | (0.15, 0.18) | 420 |
|  | Compound 20 | 4.5 | 4.4 | (0.15, 0.17) | 410 |
|  | Compound 33 | 4.6 | 4.9 | (0.15, 0.18) | 451 |
|  | Compound 34 | 4.5 | 4.4 | (0.15, 0.17) | 399 |
|  | Compound 35 | 4.6 | 4.9 | (0.15, 0.18) | 380 |
|  | Compound 36 | 4.4 | 5.0 | (0.15, 0.17) | 570 |
|  | Compound 52 | 4.6 | 4.5 | (0.15, 0.18) | 510 |
|  | Compound 61 | 4.5 | 4.4 | (0.15, 0.17) | 523 |
|  | Compound 63 | 4.5 | 4.4 | (0.15, 0.17) | 499 |
|  | Compound 89 | 4.6 | 4.9 | (0.15, 0.18) | 510 |
|  | Compound 91 | 4.4 | 5.0 | (0.15, 0.17) | 480 |
|  | Compound 117 | 4.6 | 4.5 | (0.15, 0.18) | 700 |
|  | Compound 119 | 4.5 | 4.4 | (0.15, 0.17) | 630 |
|  | Compound 122 | 4.4 | 5.0 | (0.15, 0.17) | 550 |
|  | Compound 123 | 4.6 | 4.5 | (0.15, 0.18) | 500 |
|  | Compound 124 | 4.5 | 4.4 | (0.15, 0.17) | 461 |
|  | Compound 145 | 4.5 | 4.4 | (0.15, 0.17) | 500 |
|  | Compound 147 | 4.6 | 4.9 | (0.15, 0.18) | 520 |

TABLE 3-continued

| Experimental Example | Electron transporting layer material | Driving voltage (V) | Efficiency (cd/A) | Color coordinate (x, y) | Service life (T$_{50}$) |
|---|---|---|---|---|---|
| | Compound 169 | 4.4 | 5.0 | (0.15, 0.17) | 530 |
| | Compound 176 | 4.6 | 4.5 | (0.15, 0.18) | 490 |
| | Compound 178 | 4.5 | 4.4 | (0.15, 0.17) | 450 |
| | Compound 187 | 4.5 | 4.4 | (0.15, 0.17) | 471 |
| | Compound 13 | 4.1 | 5.0 | (0.15, 0.17) | 580 |
| | Compound 19 | 4.3 | 5.1 | (0.15, 0.18) | 520 |
| | Compound 23 | 4.3 | 4.9 | (0.15, 0.17) | 430 |
| | Compound 25 | 4.3 | 4.8 | (0.15, 0.17) | 600 |
| | Compound 38 | 4.5 | 4.4 | (0.15, 0.17) | 450 |
| | Compound 39 | 4.5 | 4.4 | (0.15, 0.17) | 471 |
| | Compound 40 | 4.5 | 4.4 | (0.15, 0.17) | 450 |
| | Compound 48 | 4.5 | 4.4 | (0.15, 0.17) | 471 |
| | Compound 53 | 4.5 | 4.4 | (0.15, 0.17) | 450 |
| | Compound 56 | 4.5 | 4.4 | (0.15, 0.17) | 471 |
| | Compound 37 | 4.1 | 5.0 | (0.15, 0.17) | 520 |
| | Compound 70 | 4.3 | 5.1 | (0.15, 0.18) | 530 |
| | Compound 75 | 3.9 | 6.0 | (0.15, 0.17) | 490 |
| | Compound 76 | 4.5 | 4.4 | (0.15, 0.18) | 450 |
| | Compound 80 | 4.1 | 5.0 | (0.15, 0.17) | 471 |
| | Compound 82 | 4.3 | 5.1 | (0.15, 0.18) | 520 |
| | Compound 83 | 3.9 | 6.0 | (0.15, 0.17) | 530 |
| | Compound 93 | 4.5 | 4.4 | (0.15, 0.18) | 490 |
| | Compound 96 | 4.1 | 5.0 | (0.15, 0.17) | 450 |
| | Compound 97 | 4.5 | 4.4 | (0.15, 0.18) | 471 |
| | Compound 104 | 4.5 | 4.4 | (0.15, 0.17) | 520 |
| | Compound 107 | 4.5 | 4.4 | (0.15, 0.17) | 530 |
| | Compound 110 | 4.5 | 4.4 | (0.15, 0.18) | 490 |
| | Compound 132 | 4.1 | 5.0 | (0.15, 0.17) | 450 |
| | Compound 138 | 4.3 | 5.1 | (0.15, 0.17) | 520 |
| | Compound 148 | 3.9 | 6.0 | (0.15, 0.18) | 530 |
| | Compound 149 | 4.5 | 4.4 | (0.15, 0.17) | 490 |
| | Compound 153 | 4.5 | 4.4 | (0.15, 0.18) | 450 |
| | Compound 160 | 4.5 | 4.4 | (0.15, 0.17) | 520 |
| | Compound 166 | 4.5 | 4.4 | (0.15, 0.18) | 530 |
| | Compound 168 | 4.5 | 4.4 | (0.15, 0.17) | 490 |
| | Compound 170 | 4.1 | 5.0 | (0.15, 0.18) | 520 |
| | Compound 175 | 4.3 | 5.1 | (0.15, 0.17) | 520 |
| | Compound 174 | 3.9 | 6.0 | (0.15, 0.17) | 530 |
| | Compound 175 | 4.5 | 4.4 | (0.15, 0.18) | 490 |
| | Compound 179 | 4.1 | 5.0 | (0.15, 0.17) | 450 |
| | Compound 182 | 4.3 | 5.1 | (0.15, 0.18) | 471 |
| | Compound 186 | 3.9 | 6.0 | (0.15, 0.17) | 580 |
| | Compound 189 | 4.1 | 5.0 | (0.15, 0.17) | 520 |
| | Compound 191 | 4.3 | 5.1 | (0.15, 0.18) | 430 |
| | Compound 6 | 4.5 | 4.4 | (0.15, 0.17) | 520 |
| | Compound 8 | 4.5 | 4.4 | (0.15, 0.18) | 530 |
| | Compound 42 | 4.5 | 4.4 | (0.15, 0.17) | 520 |
| | Compound 66 | 4.5 | 4.4 | (0.15, 0.18) | 530 |
| | Compound 118 | 4.1 | 5.0 | (0.15, 0.17) | 490 |
| | Compound 120 | 4.5 | 4.4 | (0.15, 0.18) | 520 |
| | Compound 125 | 4.5 | 4.4 | (0.15, 0.17) | 530 |
| | Compound 126 | 4.5 | 4.4 | (0.15, 0.18) | 490 |
| | Compound 135 | 4.5 | 4.4 | (0.15, 0.18) | 450 |
| | Compound 139 | 4.5 | 4.4 | (0.15, 0.18) | 471 |
| | Compound 150 | 4.5 | 4.4 | (0.15, 0.18) | 580 |
| | Compound 151 | 4.1 | 5.0 | (0.15, 0.17) | 520 |
| | Compound 152 | 4.3 | 5.1 | (0.15, 0.18) | 430 |
| | Compound 164 | 4.3 | 4.9 | (0.15, 0.17) | 670 |

As in Table 3, it can be seen that when a device is manufactured by using the electron transporting layer material used in the Examples of the present invention, the service life is increased, and the driving voltage and efficiency are improved as compared to the comparative compounds which are the electron transporting layer materials used in Comparative Examples 1 to 6.

Due to the characteristics of ET of the substituent of the present invention, the compound of the present invention is more suitable for being used as an electron transporting layer.

The invention claimed is:

1. A hetero-cyclic compound represented by any one of the following Chemical Formulae 8 to 10:

[Chemical Formula 8]

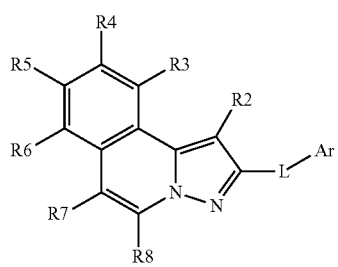

[Chemical Formula 9]

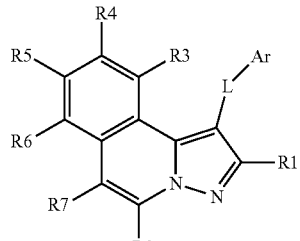

[Chemical Formula 10]

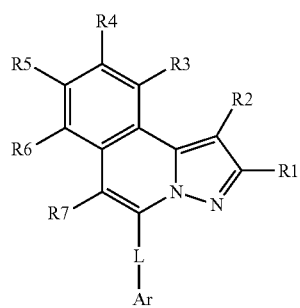

in Chemical Formulae 8 to 10, $R_1$ to $R_8$ are each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a substituted or unsubstituted $C_2$ to $C_{60}$ heteroaryl group, or two or more adjacent groups are bonded to each other to form a substituted or unsubstituted aliphatic or aromatic hydrocarbon ring, L is an unsubstituted phenylene group; or an unsubstituted biphenylene group, Ar is represented by any one of the following Chemical Formulae 2 to 7,

[Chemical Formula 2]

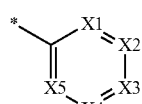

[Chemical Formula 3]

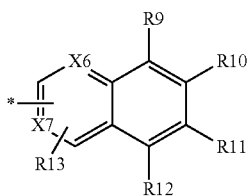

[Chemical Formula 4]

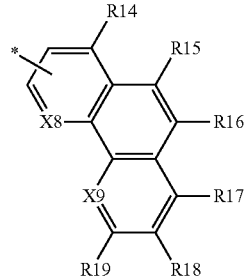

[Chemical Formula 5]

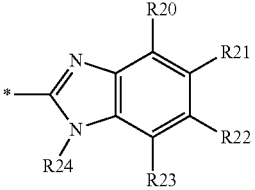

[Chemical Formula 6]

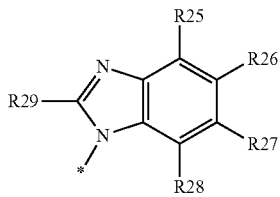

[Chemical Formula 7]

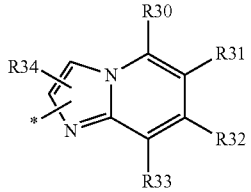

in Chemical Formulae 2 to 7, at least two of X1 to X5 is N, and the others are N or CR,
at least one of X6 and X7 is N, and the other is N or CR,
at least one of X8 and X9 is N, and the other is N or CR,
R9 to R34 are the same as or different from each other, and are each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a substituted or unsubstituted $C_2$ to $C_{60}$ heteroaryl group, or two or more adjacent groups are bonded to each other to form a substituted or unsubstituted aliphatic or aromatic hydrocarbon ring, R, R', and R" are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group, and

* denotes a position bonded to L.

2. The hetero-cyclic compound of claim 1, wherein any one of the following Chemical Formulae 8 to 10 is represented by any one of the following compounds:

5

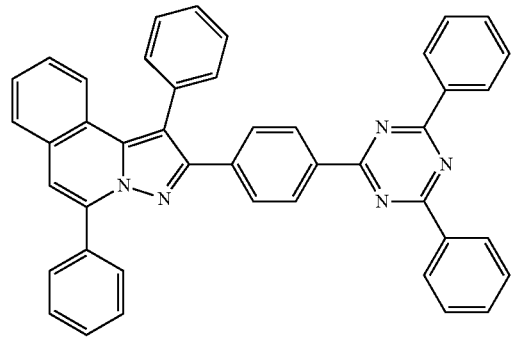

6

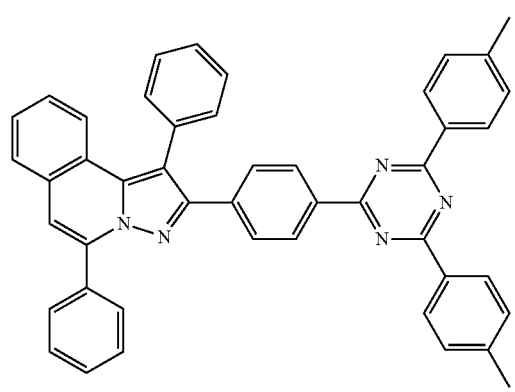

7

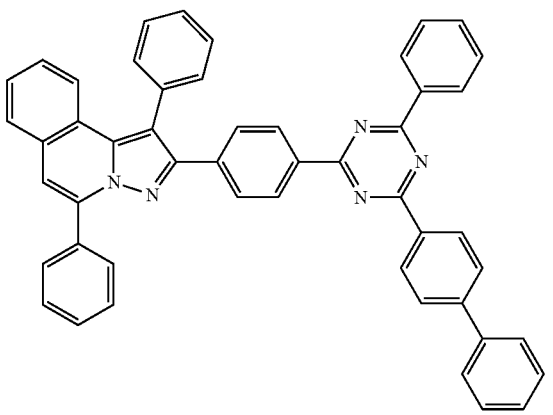

8

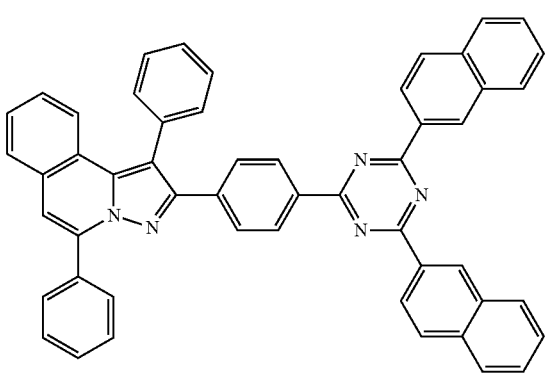

9

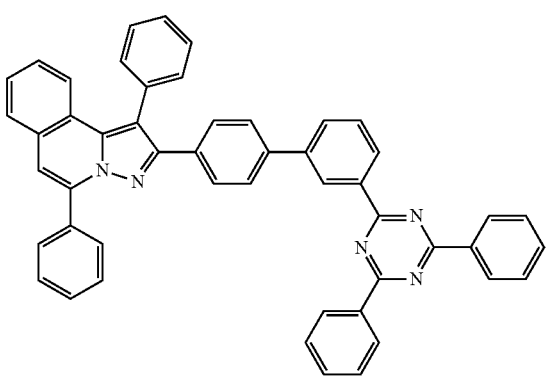

10

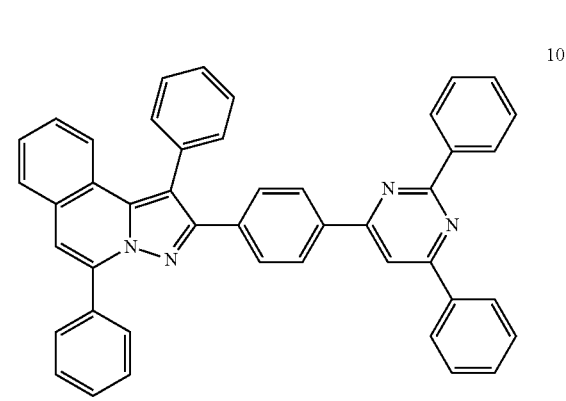

103
-continued
11
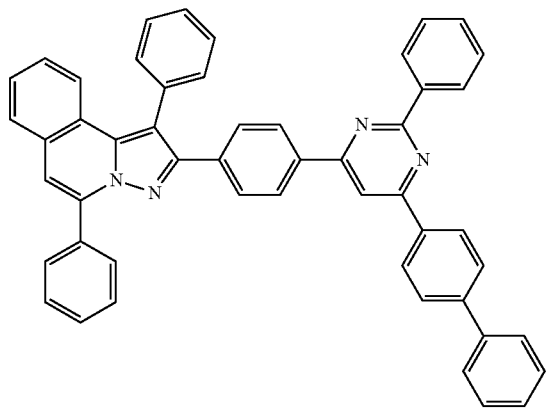
12
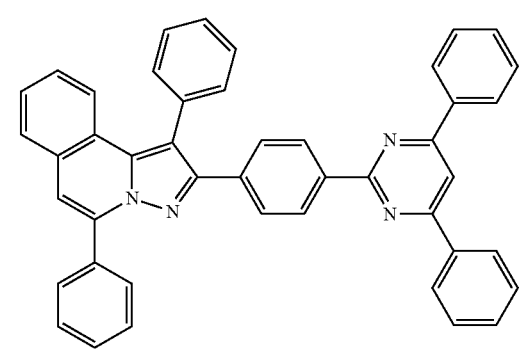
13
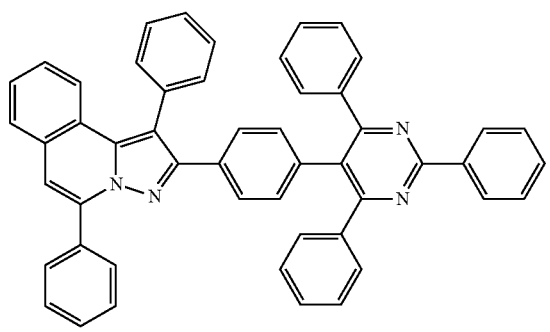
14
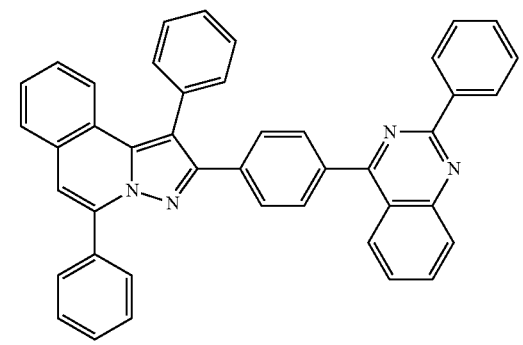
104
-continued
19
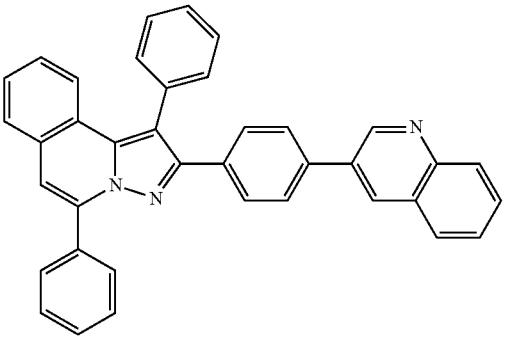
20
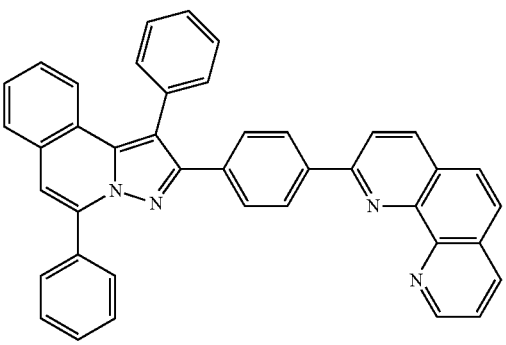
23
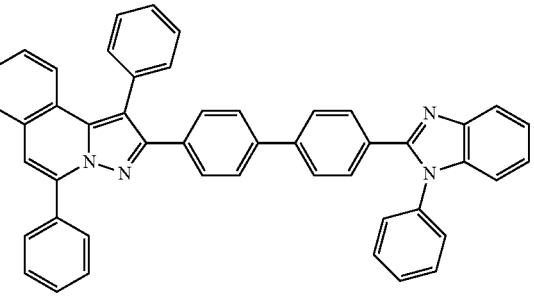
24
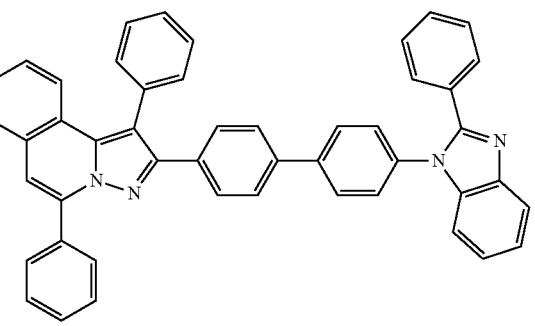

105
-continued
25
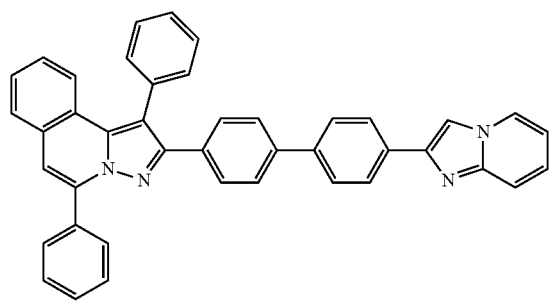
26
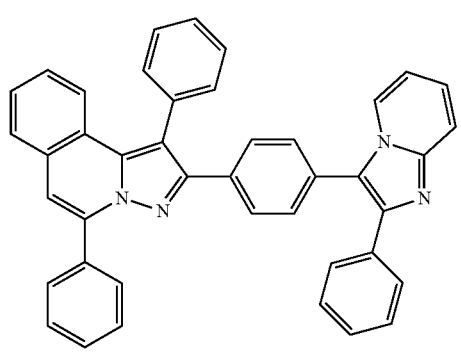
27
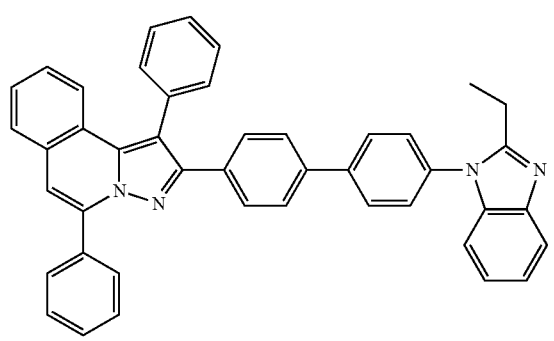
28
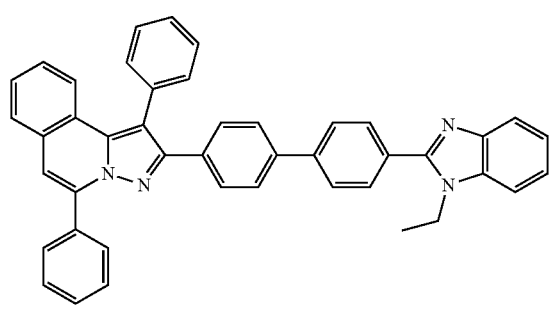
106
-continued
33
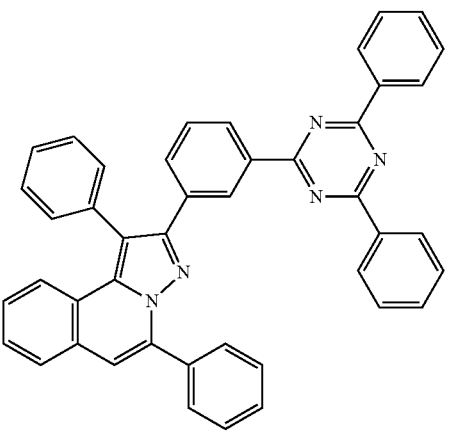
34
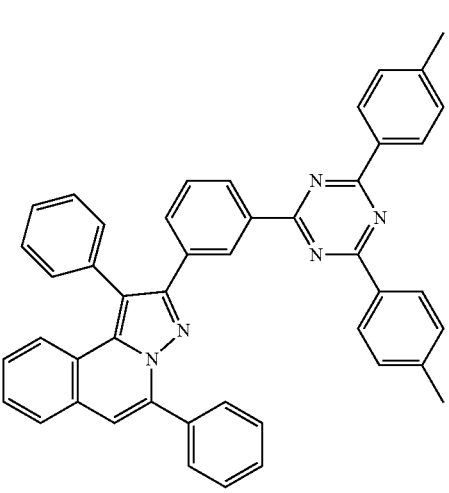
35
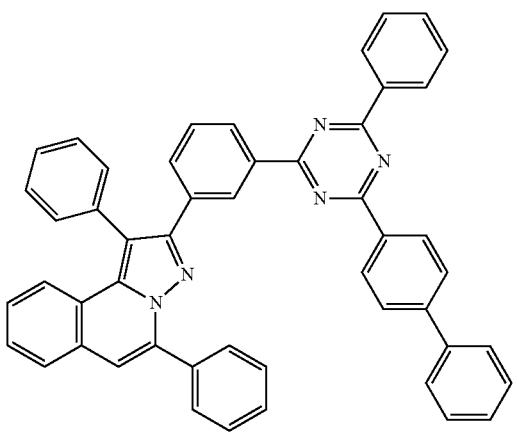

36
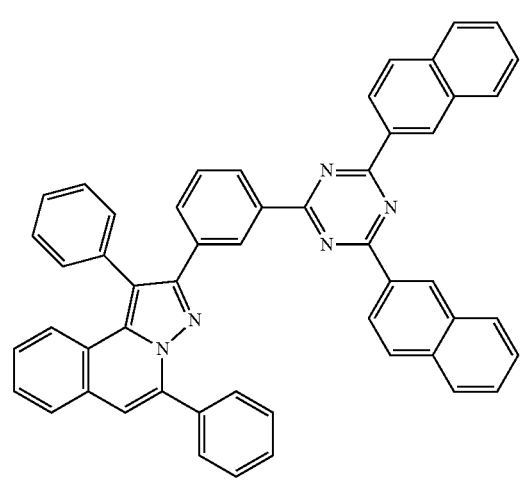
37
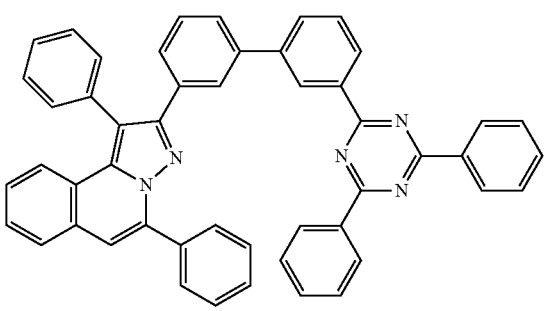
38
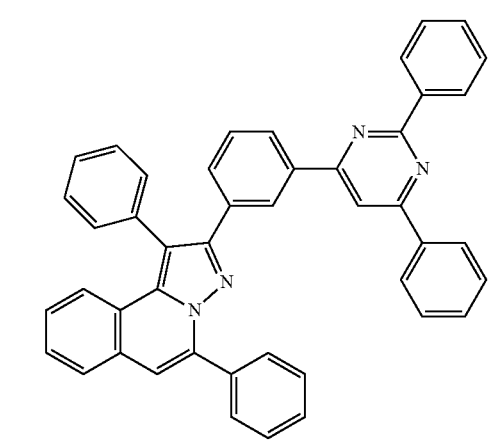
39
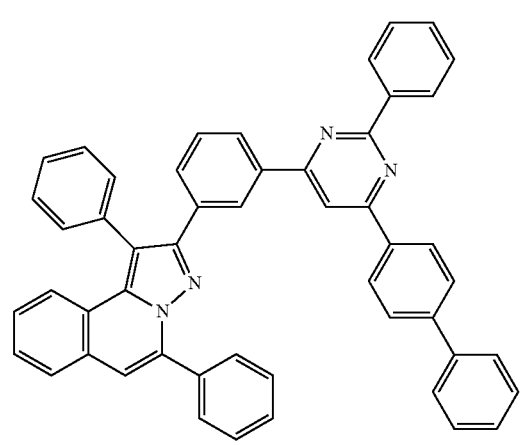
40
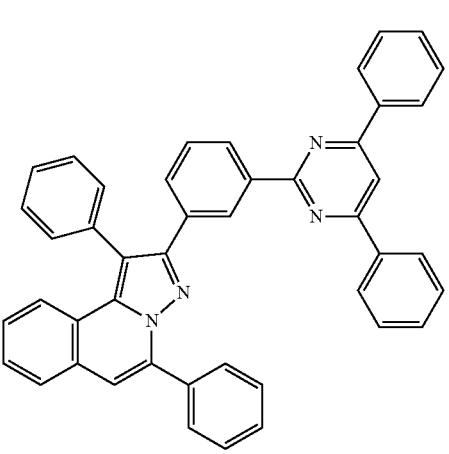
41
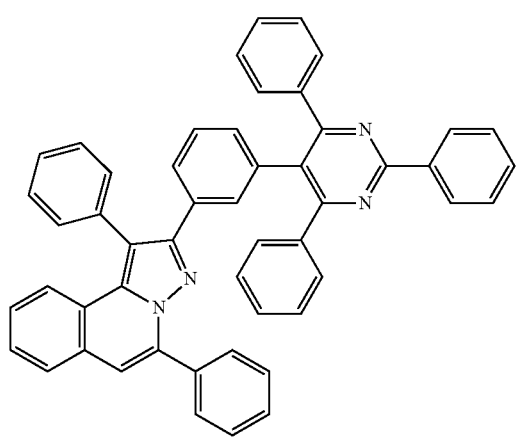
42
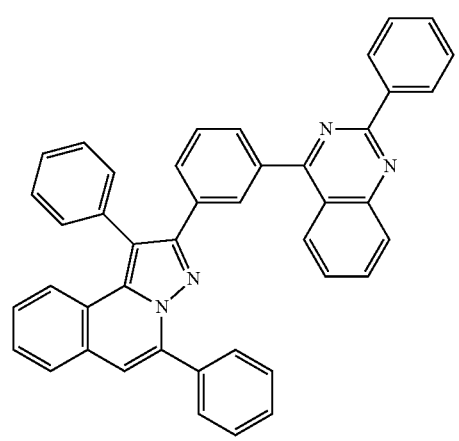
47
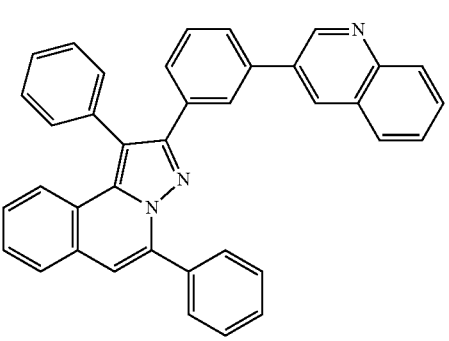

-continued
48
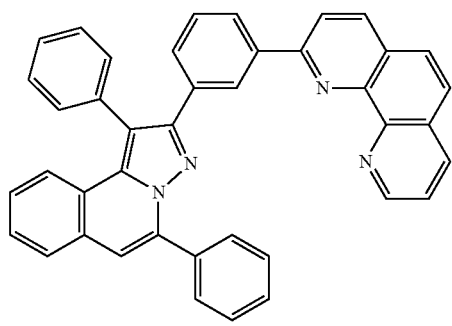
51
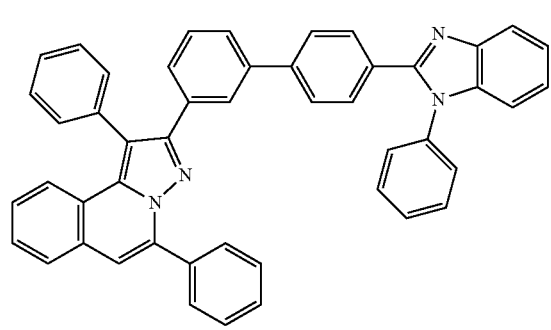
52
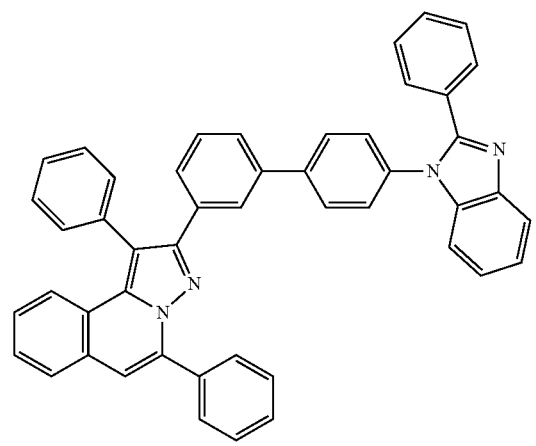
53
-continued
54
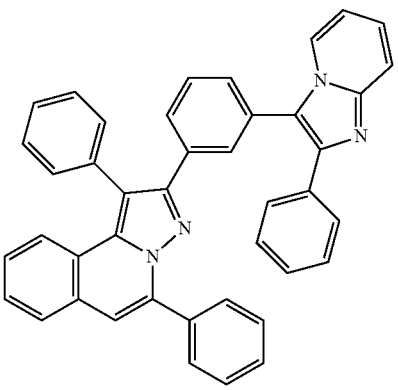
55
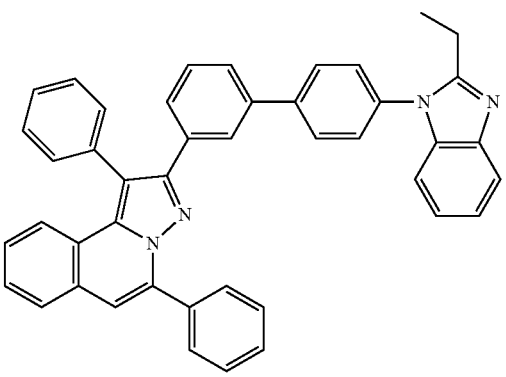
56
61
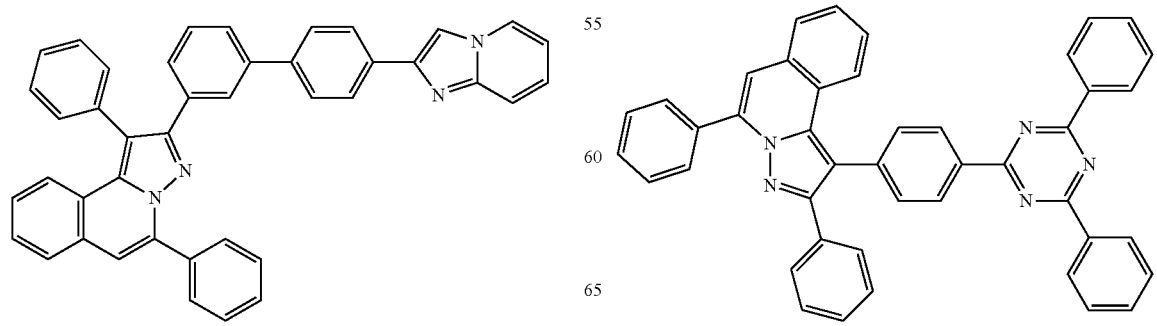

111
-continued
62
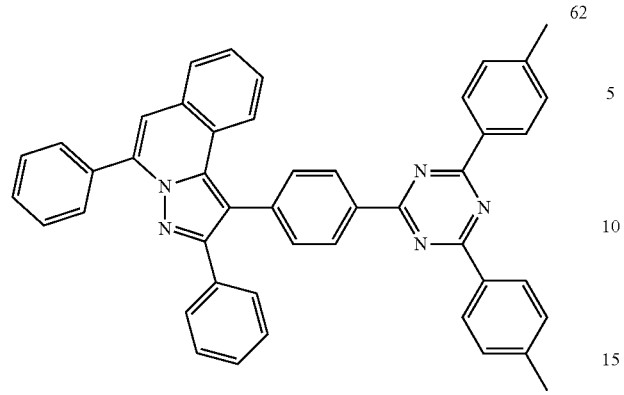
63
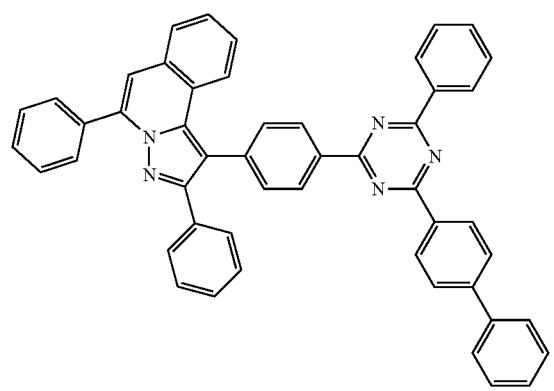
64
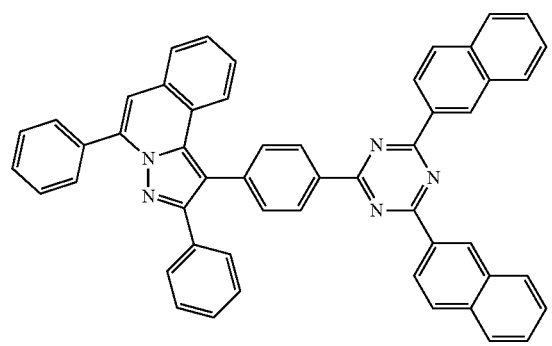
65
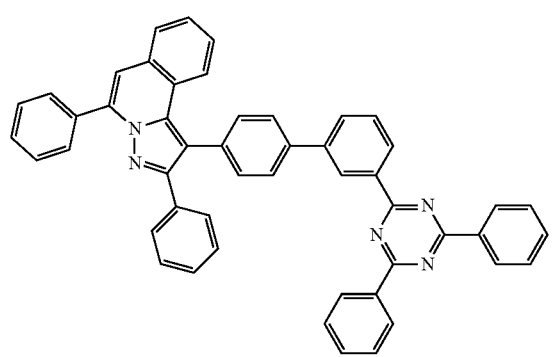
112
-continued
66
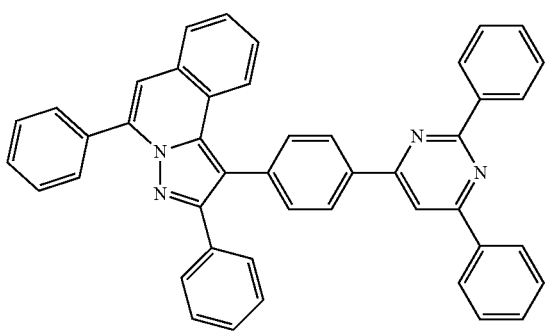
67
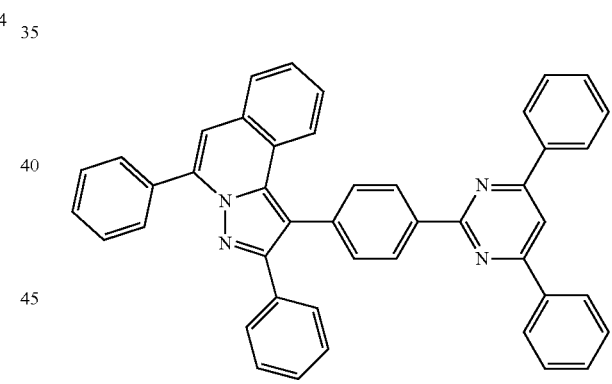
68
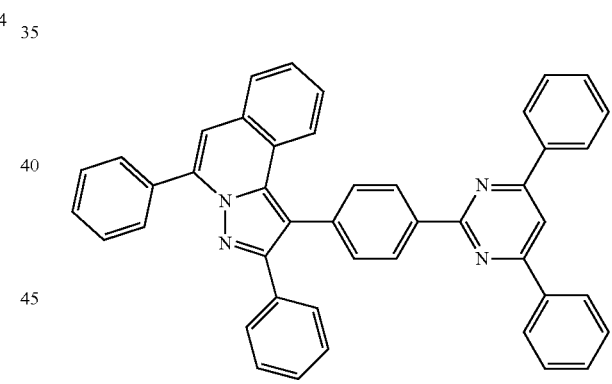
69
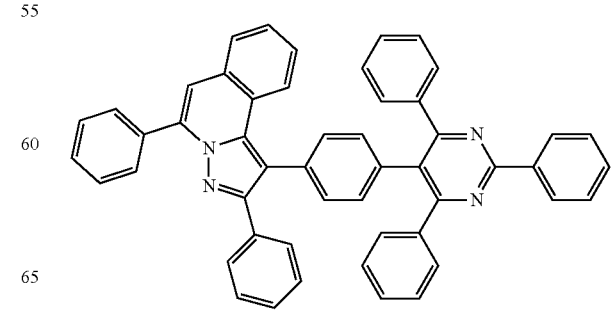

70
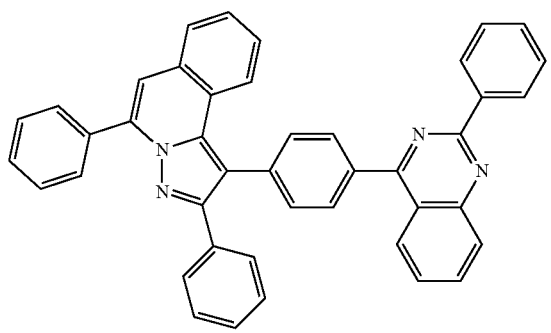
75
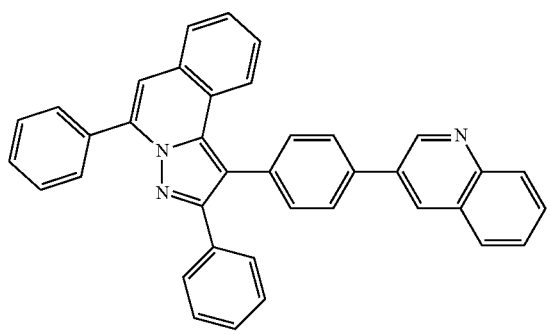
76
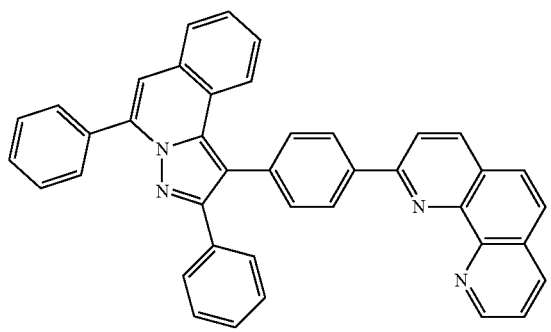
79
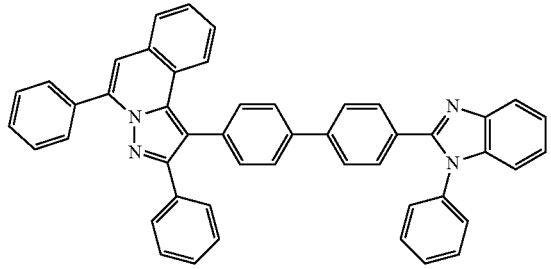
80
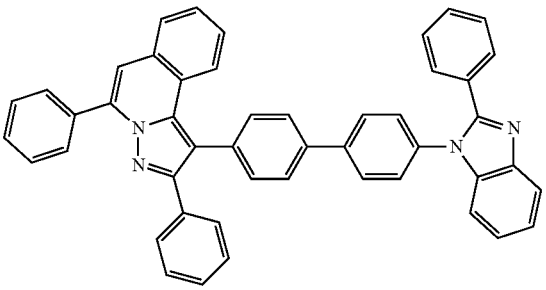
81
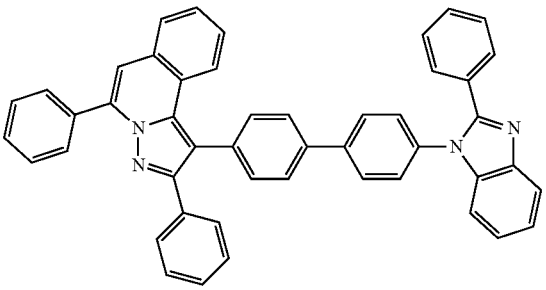
82
83
79
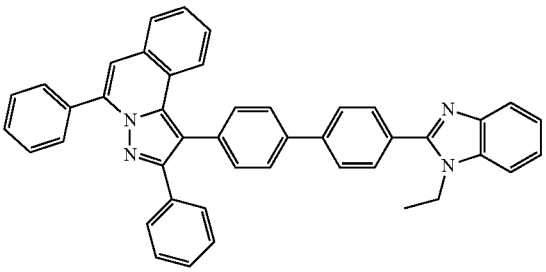
84

115
-continued
89
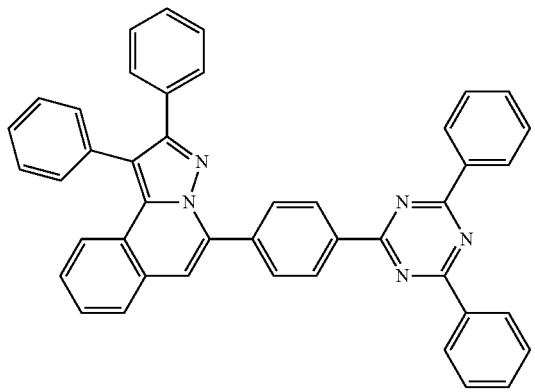
90
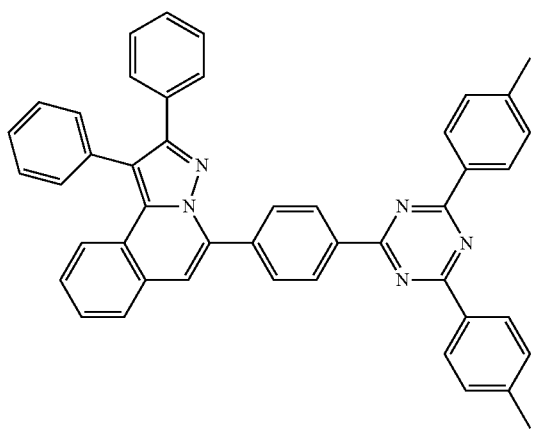
91
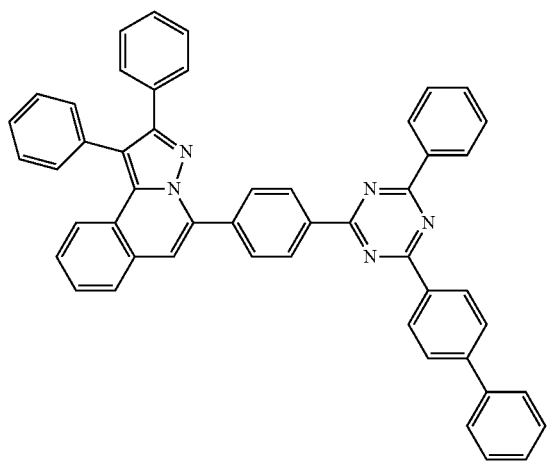
116
-continued
92
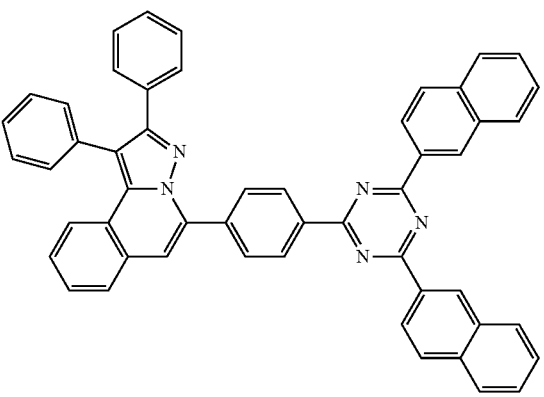
93
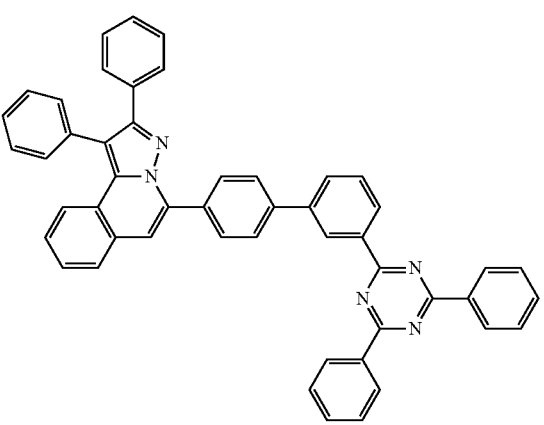
94
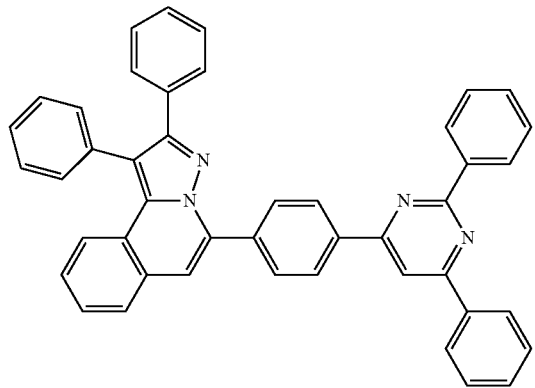

95
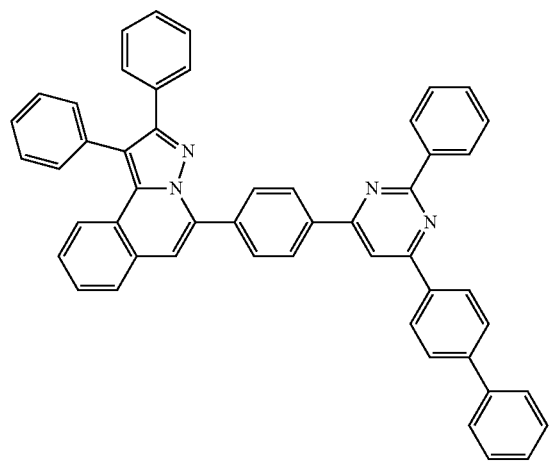
96
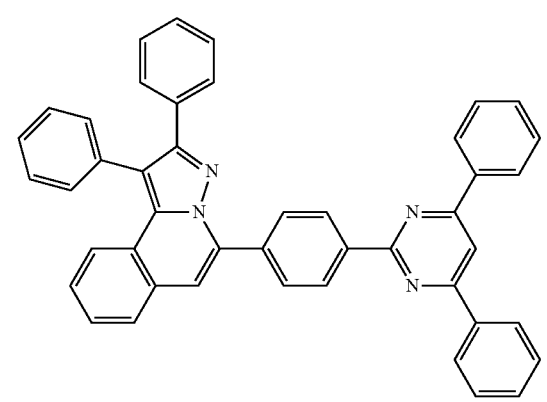
97
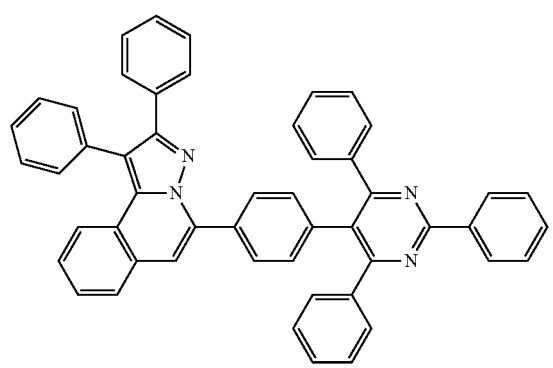
98
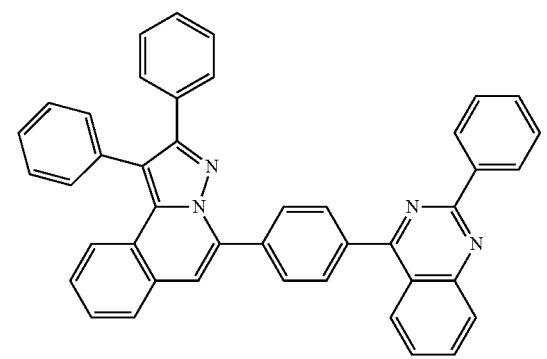
103
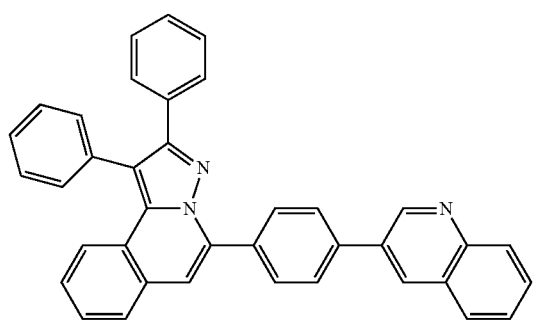
104
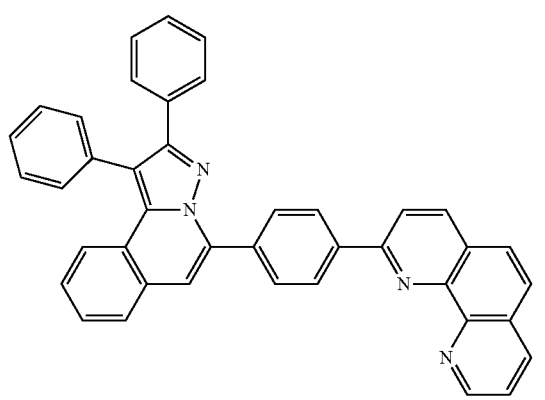
107
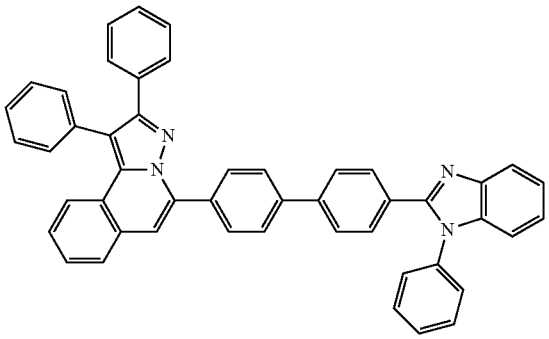
108
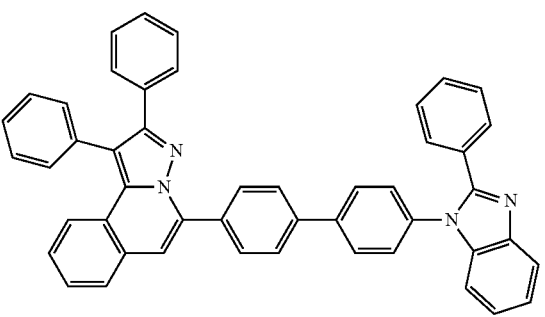

109
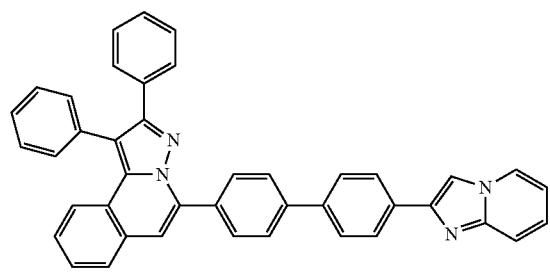
110
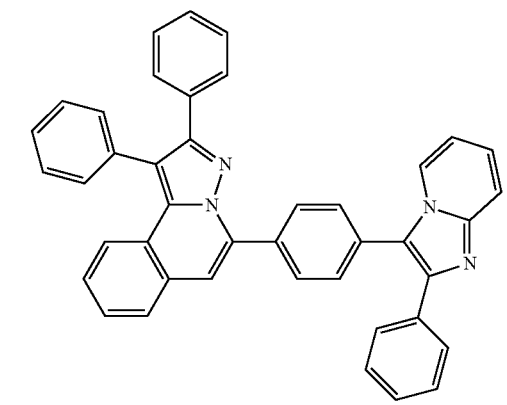
111
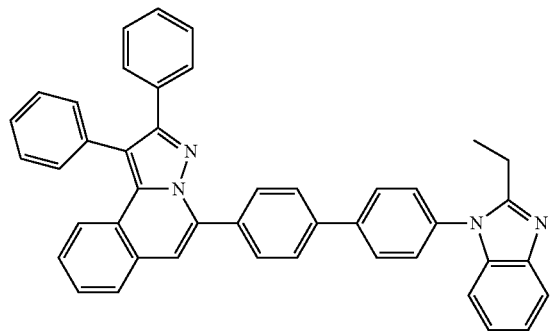
112
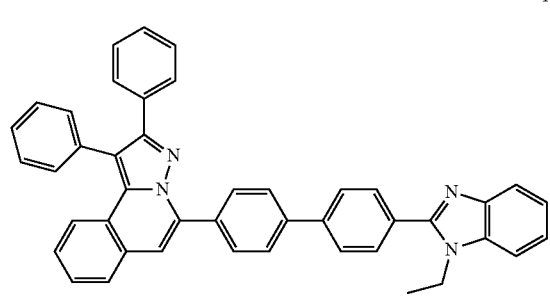
117
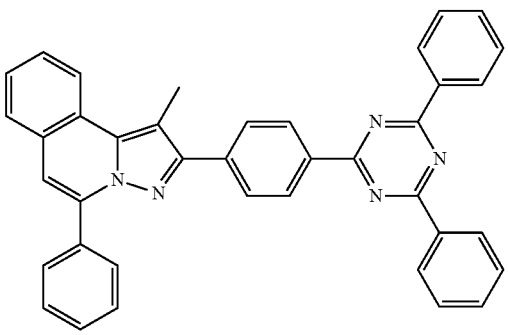
118
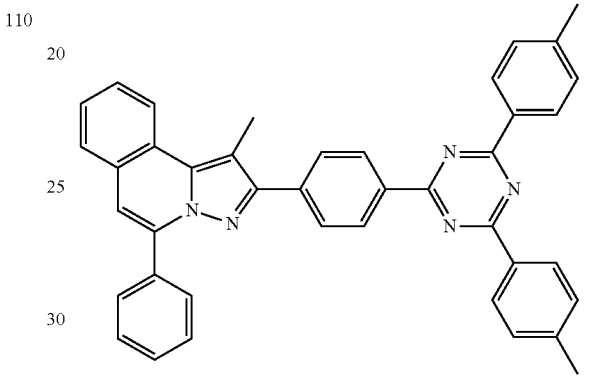
119
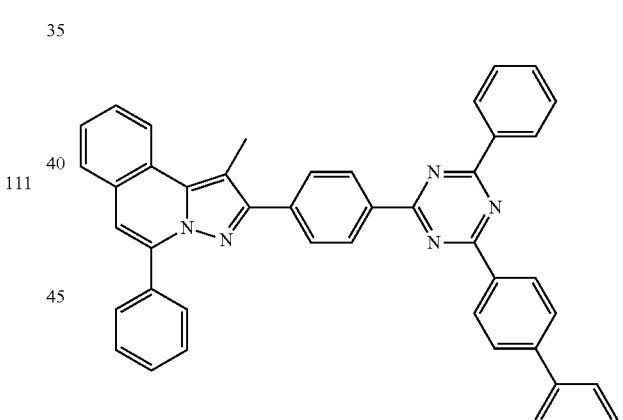
120
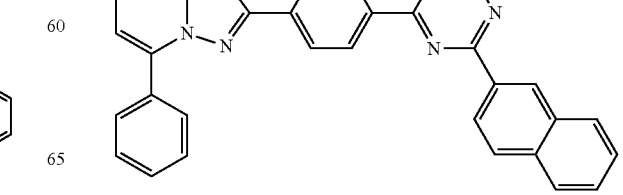

-continued
121
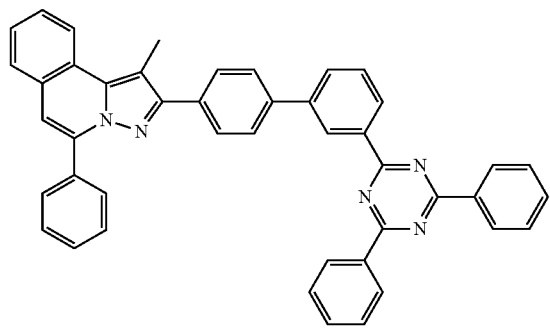
122
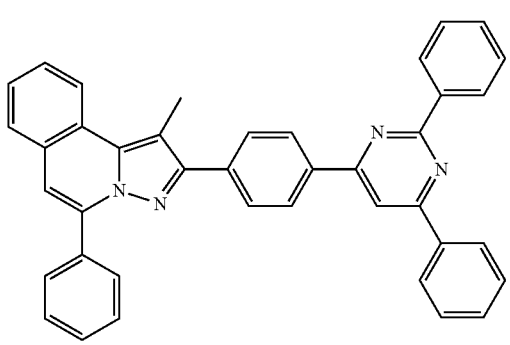
123
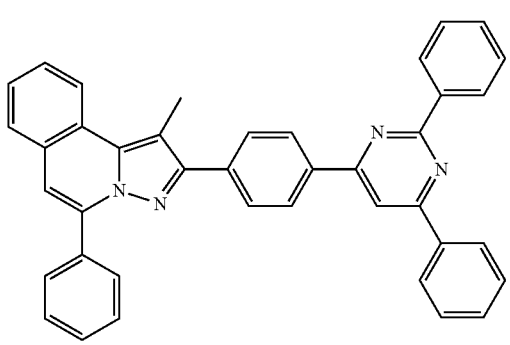
124
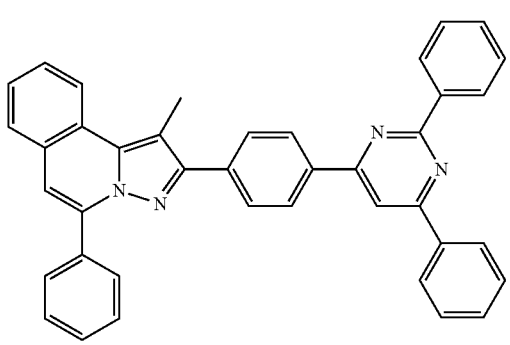
-continued
125
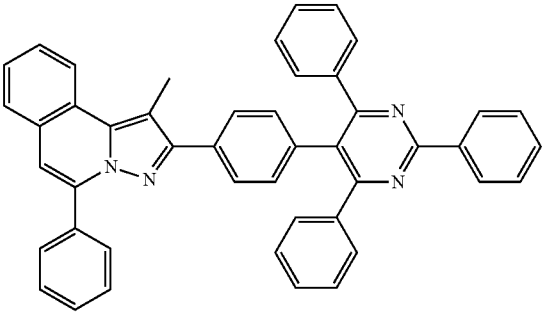
126
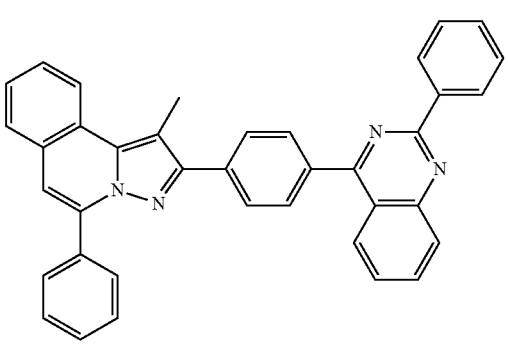
131
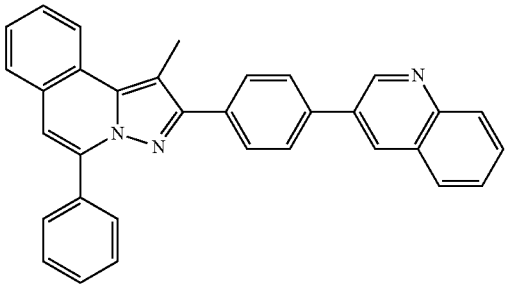
132
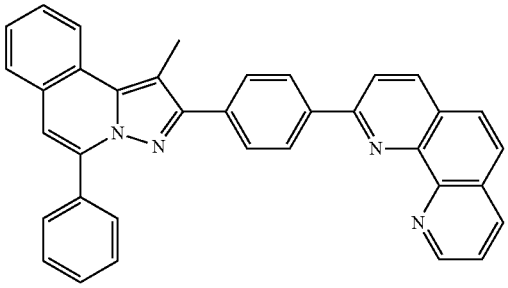
135
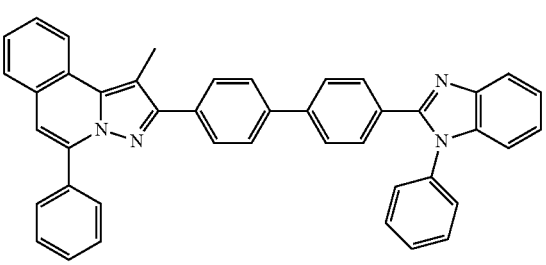

123
-continued
136
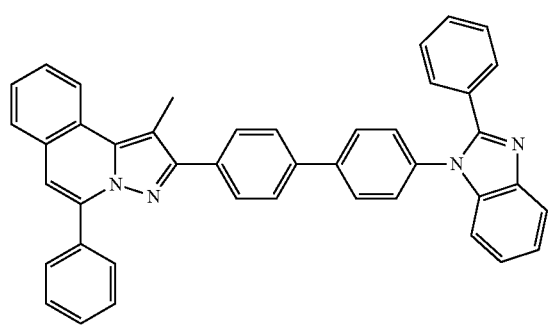
137
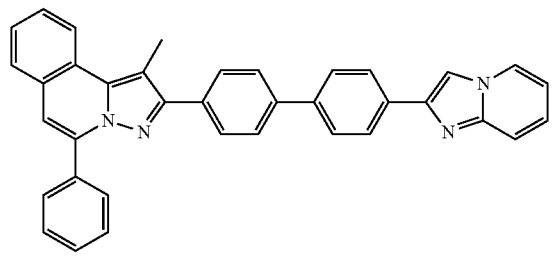
138
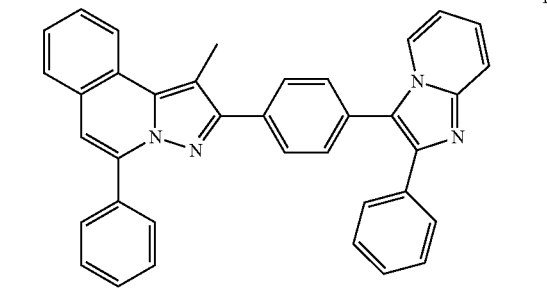
139
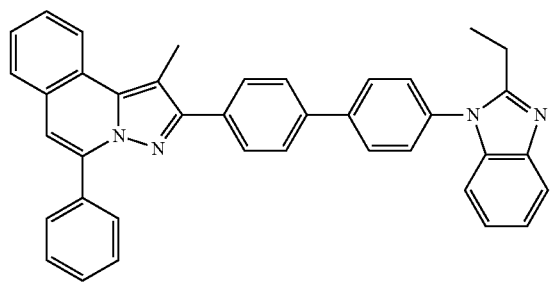
140
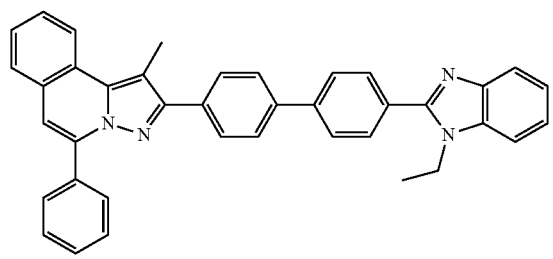
124
-continued
145
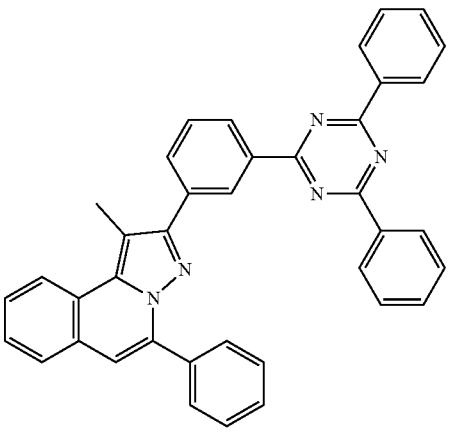
146
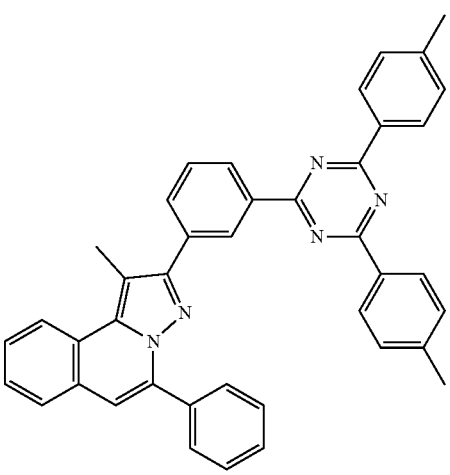
147
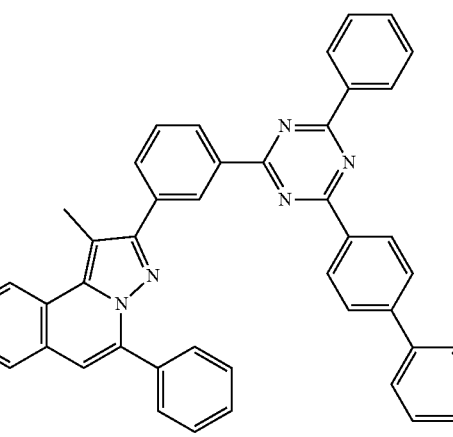

148
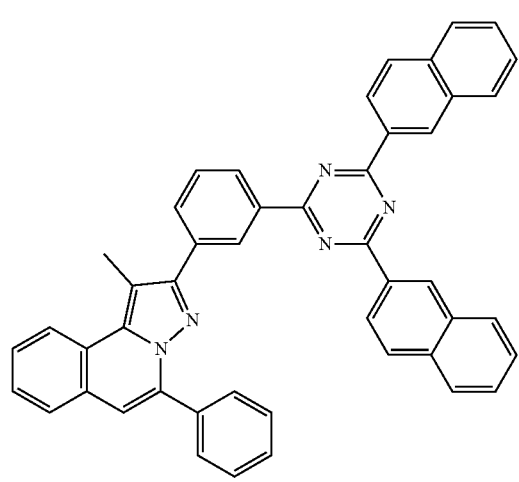
149
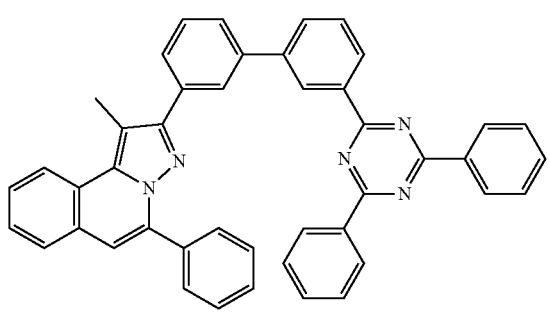
150
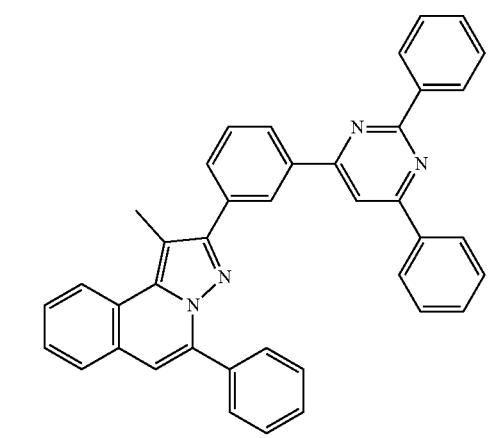
151
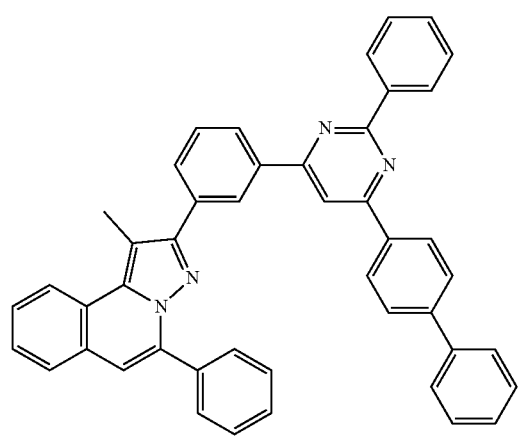
152
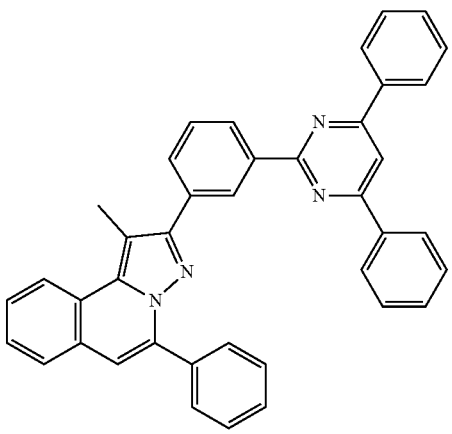
153
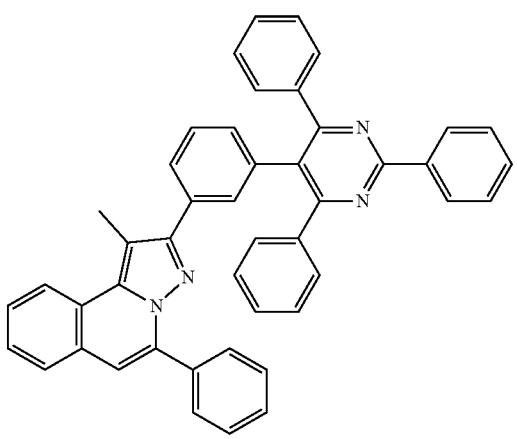
154
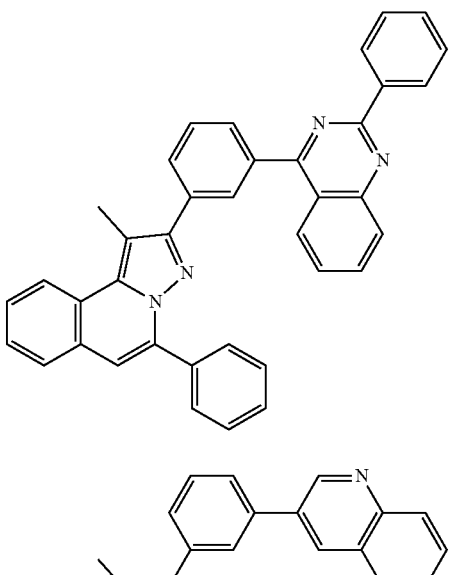
159
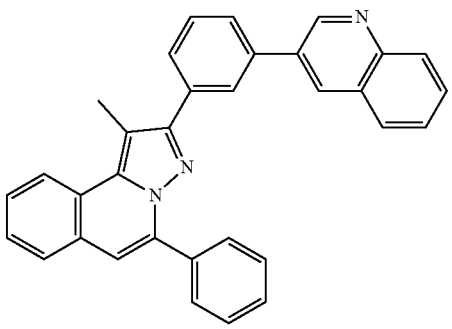

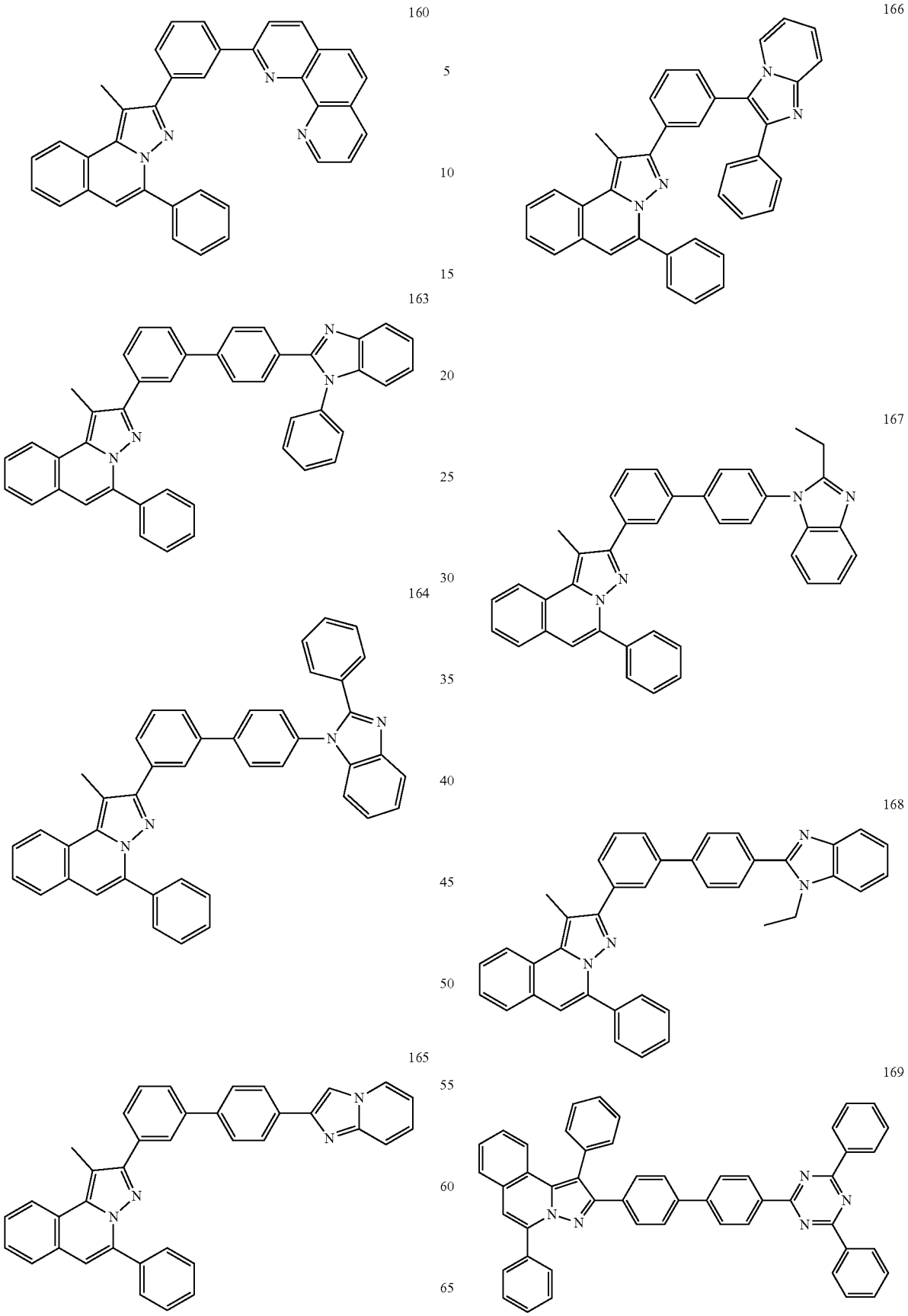

-continued
170
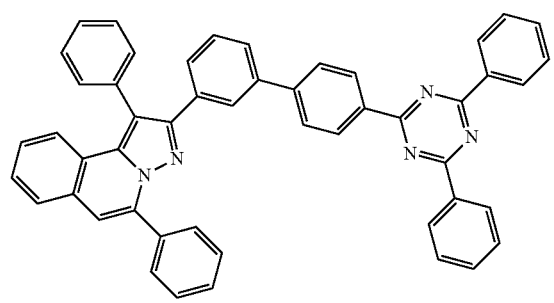
171
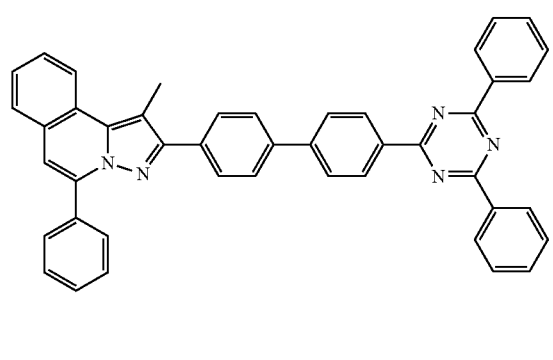
172
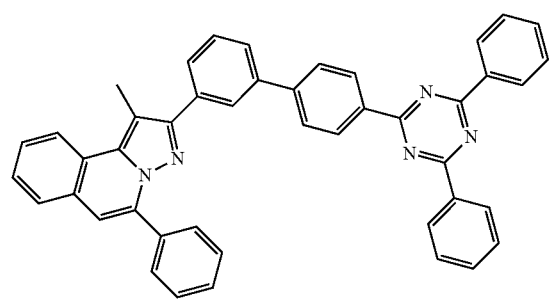
173
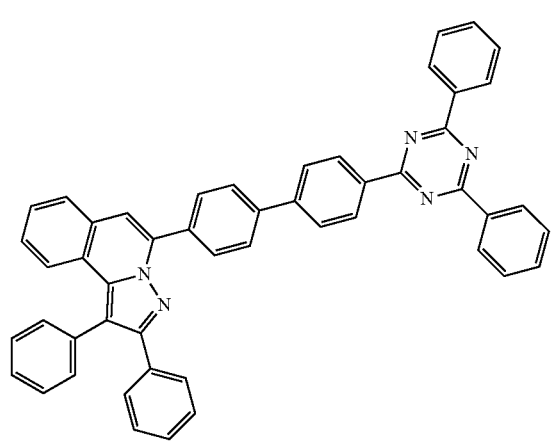
-continued
174
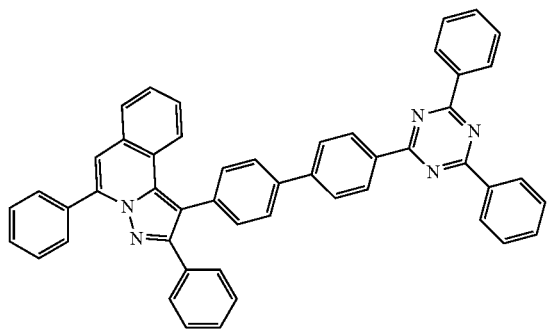
175
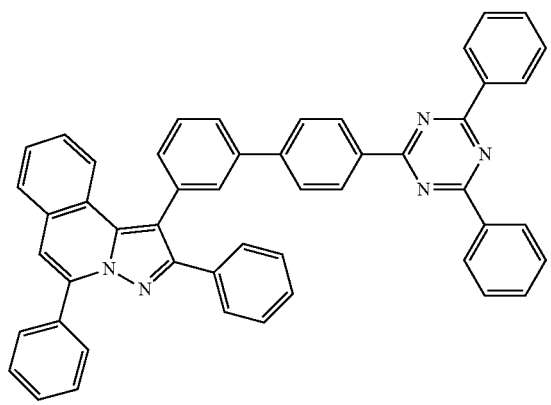
176
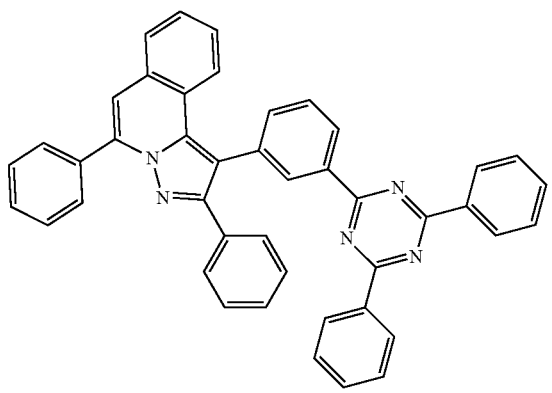
177
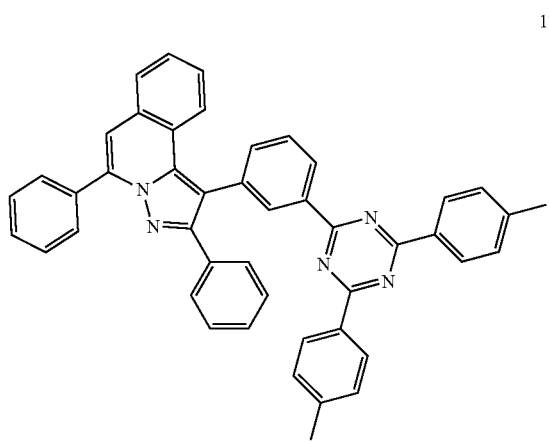

178
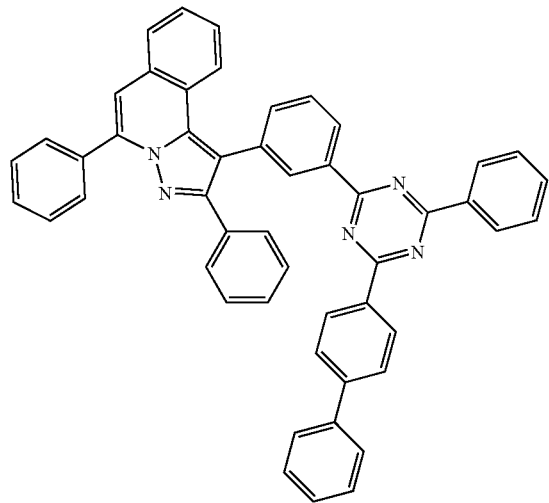
179
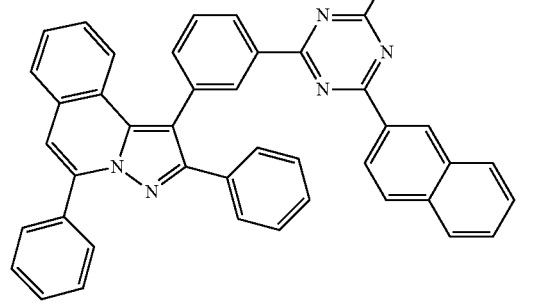
180
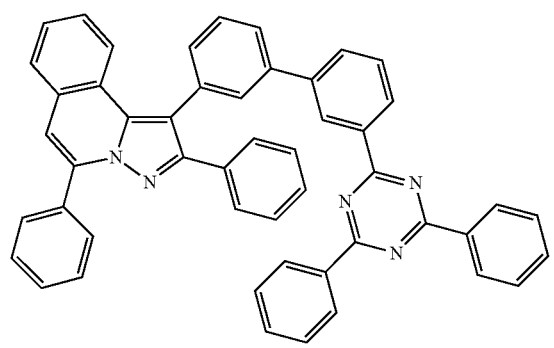
181
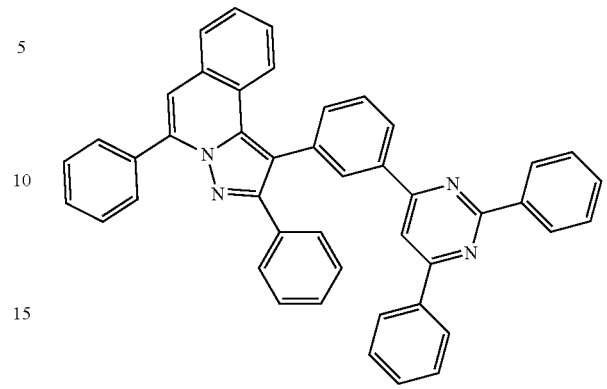
182
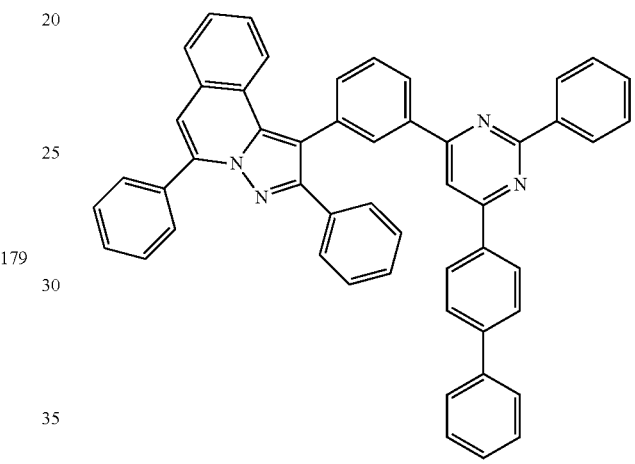
183
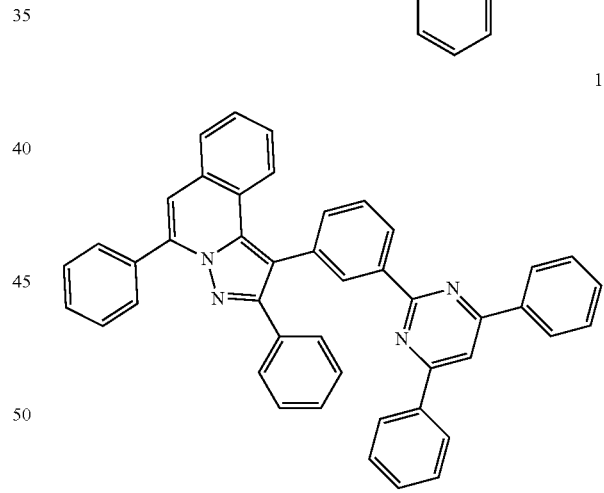
184
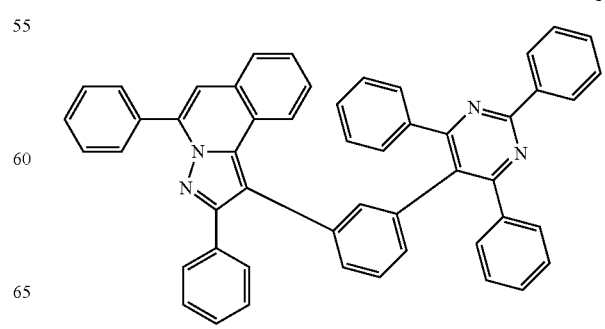

185

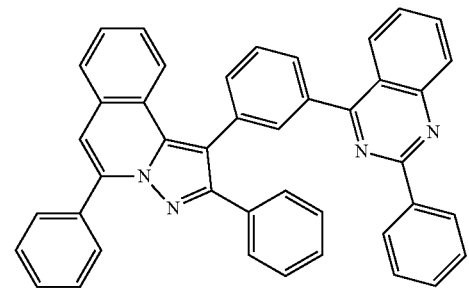

186

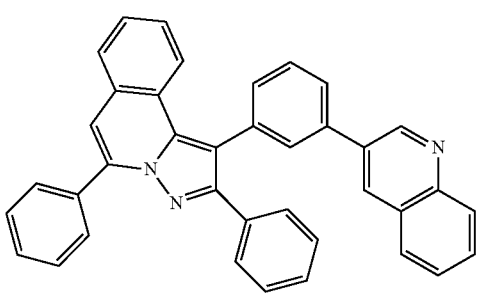

187

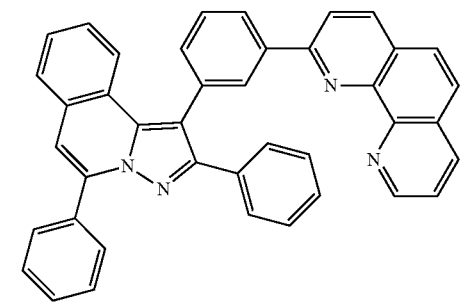

188

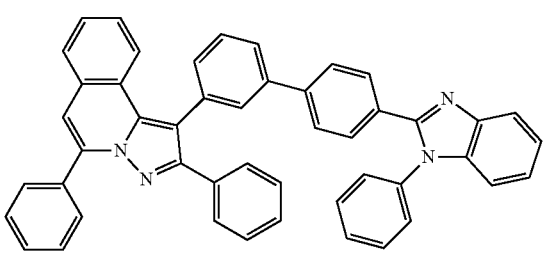

189

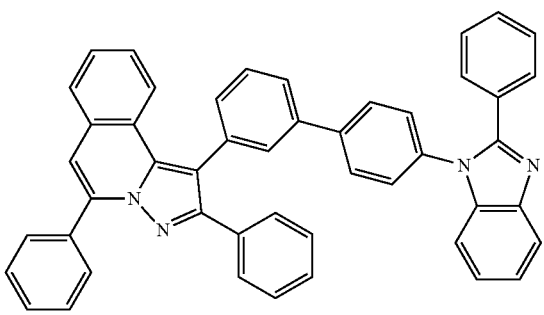

190

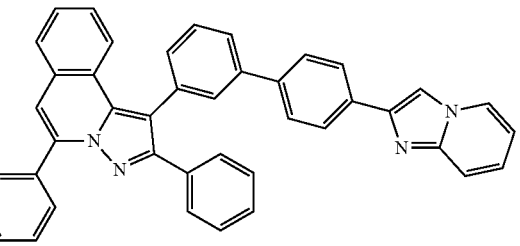

191

192

193

3. An organic light emitting device comprising:
a positive electrode;
a negative electrode; and
an organic material layer having one or more layers disposed between the positive electrode and the negative electrode,
wherein one or more layers of the organic material layer comprise the hetero-cyclic compound of claim 1.

4. The organic light emitting device of claim 3, wherein the organic material layer comprises at least one layer of a hole blocking layer, an electron injection layer, and an electron transporting layer, and at least one layer of the hole blocking layer, the electron injection layer, and the electron transporting layer comprises the hetero-cyclic compound.

5. The organic light emitting device of claim 3, wherein the organic material layer comprises a light emitting layer, and the light emitting layer comprises the hetero-cyclic compound.

6. The organic light emitting device of claim 3, wherein the organic material layer comprises one or more layers of a hole injection layer, a hole transporting layer, and a layer which injects and transports holes simultaneously, and one layer of the layers comprises the hetero-cyclic compound.

* * * * *